United States Patent
Lu et al.

(10) Patent No.: US 11,834,454 B2
(45) Date of Patent: Dec. 5, 2023

(54) ALKYNYLPHENYLBENZAMIDE COMPOUNDS AND APPLICATIONS THEREOF

(71) Applicant: SHENZHEN NEWDEL BIOTECH CO., LTD., Guangdong (CN)

(72) Inventors: Xiaoyun Lu, Guangdong (CN); Zhang Zhang, Guangdong (CN); Ke Ding, Guangdong (CN); Shuang Xiang, Guangdong (CN); Jie Wang, Guangdong (CN); Zhengchao Tu, Guangdong (CN); Zhimin Zhang, Guangdong (CN); Xia Tang, Guangdong (CN); Zuqin Wang, Guangdong (CN); Xun He, Guangdong (CN); Feng Jin, Guangdong (CN); Shuihua Zhang, Guangdong (CN); Zhenwei Li, Guangdong (CN)

(73) Assignee: SHENZHEN NEWDEL BIOTECH CO., LTD., Guangdong (CN)

( * ) Notice: Subject to any disclaimer, the term of this patent is extended or adjusted under 35 U.S.C. 154(b) by 0 days.

(21) Appl. No.: 17/948,236

(22) Filed: Sep. 20, 2022

(65) Prior Publication Data
US 2023/0046126 A1 Feb. 16, 2023

Related U.S. Application Data

(63) Continuation of application No. PCT/CN2021/117495, filed on Sep. 9, 2021.

(30) Foreign Application Priority Data

Apr. 13, 2021 (CN) .......................... 202110395086.2

(51) Int. Cl.
*A61K 9/00* (2006.01)
*C07D 487/04* (2006.01)
*A61P 35/00* (2006.01)

(52) U.S. Cl.
CPC .......... *C07D 487/04* (2013.01); *A61K 9/0053* (2013.01); *A61P 35/00* (2018.01)

(58) Field of Classification Search
CPC ...... C07D 487/04; A61P 35/00; A61K 9/0053
See application file for complete search history.

(56) References Cited

FOREIGN PATENT DOCUMENTS

| CN | 103044432 | | 4/2013 | |
|---|---|---|---|---|
| WO | 2013101281 | | 7/2013 | |
| WO | 2014019338 | | 2/2014 | |
| WO | WO2014/019338 | * | 2/2014 | ........... C07D 519/00 |
| WO | 2015085972 | | 6/2015 | |
| WO | 2015108490 | | 7/2015 | |
| WO | 2018089736 | | 5/2018 | |

OTHER PUBLICATIONS

Jia JV Yang, "Design, Synthesis and Biological Evaluation of TRK inhibitors," Thesis of Master Degree, Jiangnan University, Jun. 2019, pp. 1-127.

* cited by examiner

*Primary Examiner* — Erich A Leeser
(74) *Attorney, Agent, or Firm* — JCIPRNET

(57) ABSTRACT

The present disclosure relates to Alkynylphenylbenzamide compounds and the applications thereof. The said Alkynylphenylbenzamide compounds have the structure shown in Formula (I). The compounds can be used as protein kinase inhibitors, which can effectively inhibit the activity of TRK protein kinase and the proliferation, migration and invasion of various tumor cells. At the same time, it has the characteristics of good pharmacokinetics and low toxicity.

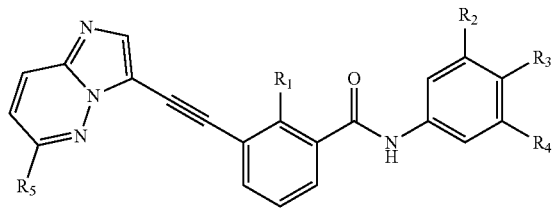

15 Claims, 2 Drawing Sheets

ALKYNYLPHENYLBENZAMIDE COMPOUNDS AND APPLICATIONS THEREOF

CROSS-REFERENCE TO RELATED APPLICATION

This application is a continuation of international application of PCT application serial no. PCT/CN2021/117495 filed on Sep. 9, 2021, which claims the priority benefit of China application no. 202110395086.2 filed on Apr. 13, 2021. The entirety of each of the above mentioned patent applications is hereby incorporated by reference herein and made a part of this specification.

BACKGROUND OF THE INVENTION

1. Technical Field

The present disclosure relates to the chemical and pharmaceutical technology, in particular to a kind of Alkynylphenylbenzamide compounds and the applications thereof.

2. Background Art

TRK (tropomyosin receptor kinase) belongs to the receptor tyrosine kinase (RTK) family, and has three subtypes: TRKA, TRKB, and TRKC, which are encoded respectively by NTRK1, NTRK2, and NTRK3 genes. TRK is a kind of transmembrane protein, which is composed of extracellular ligand binding domain, transmembrane domain (TM) and intracellular domain. TRK plays its role mainly by binding neurotrophic factors (NTs), which are a class of protein molecules that are produced by nerve-innervated tissues (such as muscles) and astrocytes and are necessary for neuronal growth and survival. At present, four main neurotrophic factors have been found, including NGF (nerve growth factor), brain-derived neurotrophic factor (BDNF), neurotrophic factor 3 (NT-3) and neurotrophic factor 4 (NT-4), among which NGF binds to TRKA, BDNF and NT-4 bind to TRKB, and NT-3 can bind to the three TRK proteins, but its binding ability to TRKC is stronger. When activated by signal induction, TRK activates downstream signaling pathways in turn through self-dimerization and phosphorylation to achieve various cellular physiological functions. The downstream signaling pathways of TRK include MAPK, PI3K/AKT, PLCγ/PKC pathways, which regulate physiological processes such as cell proliferation, differentiation, migration, and apoptosis, as well as various physiological activities related to neurons such as the elasticity of neural synapses, the growth and repair of neural dendrites, the prevention and repair of neuronal degradation, and the maintenance of sensory neurons.

Numerous studies have shown that TRK overexpression, gene fusion and single nucleotide changes are closely related to the occurrence and development of various types of tumors, such as non-small cell lung cancer, breast cancer, colon cancer, prostate cancer, thyroid cancer, malignant melanoma, neuroblastoma and breast-like secretory carcinoma, etc. Among the mechanisms of abnormal activation of TRK, the most prevalent mechanism is the gene fusion of TRK. The earliest NTRK fusion gene discovered in medical research was the TPM3-NTRK1 fusion gene found in colon cancer samples. With further in-depth research, researchers have successively discovered various types of fusion genes such as CD74-NTRK1, ETV6-NTRK2, QKI-NTRK2, and ETV6-NTRK3. The TRK fusion protein expressed by the NTRK fusion gene can continuously activate downstream signaling pathways independent of ligand binding, thereby inducing abnormal cell proliferation and promotes the occurrence and development of tumors. Therefore, TRK is regarded as an effective anticancer therapeutic target.

At present, a TRK selective inhibitor, Larotrectinib, developed by LOXO in the United States, was approved by the FDA in 2018; and Entrectinib, a TRK inhibitor developed by Roche Pharmaceuticals, was launched in Japan in June 2019; and Belizatinib, developed by TESARO, is undergoing clinical studies. In addition, multi-target inhibitors such as Cabozanitinib, Sitravatinib, and Altiratinib also have good TRK inhibitory activities.

The point mutation of NTRK gene caused by continuous use of TRK inhibitors is the key reason for the development of drug resistance in tumors. Clinical studies have successively discovered the mutations in G595R, G667C, F589L, G667S of NTRK1, and G623R and G696A of NTRK3. However, there are currently no inhibitors targeting these mutations on the market, and the second-generation of TRK inhibitors LOXO-195, TPX-0005 and ONO-5390556 are in clinical studies.

SUMMARY OF THE INVENTION

Based on the above, the present disclosure provides a new class of Alkynylphenylbenzamide compounds or their pharmaceutically acceptable salts or stereoisomers, which can be used as protein kinase inhibitors, and can effectively inhibit the activity of TRK protein kinase as well as the proliferation, migration and invasion of various tumor cells, especially with good pharmacokinetic properties and anti-drug resistance.

The detailed technical solutions are as follows:

The Alkynylphenylbenzamide compounds with the structure shown in Formula (I) or their pharmaceutically acceptable salts or stereoisomers or prodrug molecules:

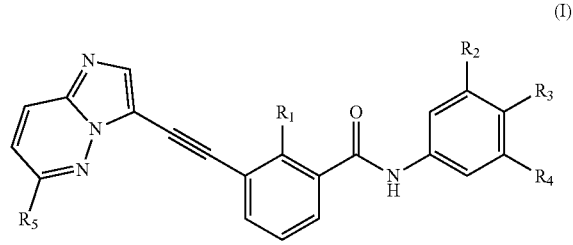

wherein, $R_1$ is selected from: $C_1\text{--}C_{20}$ alkyl;

$R_2$ is selected from: H, halogen, $C_1\text{--}C_{20}$ alkyl, $C_1\text{--}C_{20}$ alkoxy and halogen-substituted $C_1\text{--}C_{20}$ alkyl;

$R_3$ is selected from: H, fluorine-substituted $C_1\text{--}C_4$ alkyl, and substituted or unsubstituted 5-6 membered heterocyclic group containing 1-3 N ring atoms;

$R_4$ is selected from: H, halogen, nitro, substituted or unsubstituted $C_1\text{--}C_{20}$ alkyl, substituted or unsubstituted $C_1\text{--}C_{20}$ alkoxy, substituted or unsubstituted 5-10 membered heterocyclyl containing 1-3 N ring atoms, and substituted or unsubstituted 5-10 membered heteroaryl containing 1-3 N ring atoms;

$R_5$ is —$NR_6R_7$;

wherein, $R_6$ and $R_7$ are independently selected from: —$(CH_2)_m NR_8 R_9$, —$(CH_2)_n CR_{10}R_{11}R_{12}$, and —$(CH_2)_p OR_{12}$; or $R_6$ and $R_7$ together with the attached nitrogen atom form a substituted or unsubstituted monocyclic ring, fused ring, spiro ring or bridged ring containing heteroatom;

$R_8$ and $R_9$ are independently selected from: H, and $C_1$~$C_{20}$ alkyl; or $R_8$ and $R_9$ together with the attached nitrogen atom form a substituted or unsubstituted monocyclic ring, fused ring, spiro ring or bridged ring containing 1-3 heteroatoms;

$R_{10}$ and $R_{11}$ together with the attached carbon atom form a substituted or unsubstituted monocyclic ring, fused ring, spiro ring or bridged ring containing 1-3 heteroatoms;

$R_{12}$ is selected from: H, and $C_1$~$C_{20}$ alkyl;

m, n, and p are each independently selected from: an integer from 0 to 10.

In some embodiments, $R_4$ is selected from: H, halogen, nitro, $C_1$~$C_{10}$ alkyl, halogen-substituted $C_1$~$C_{10}$ alkyl, $C_1$~$C_{10}$ alkoxy, halogen-substituted $C_1$~$C_{10}$ alkoxy, —$(CH_2)_xNR_{17}R_{18}$, 5-10 membered heterocyclyl group containing 1-3 N ring atoms and substituted or unsubstituted by 1-5 $R_{19}$, and 5-10 membered heteroaryl containing 1-3 N ring atoms and substituted or unsubstituted by 1-5 $R_{19}$; herein, x is an integer from 1 to 5;

$R_{17}$ and $R_{18}$ together with the attached nitrogen atom form a 1-5 $R_{19}$ substituted or unsubstituted morpholinyl, pyrrolidinyl, piperidinyl or piperazinyl;

each $R_{19}$ is independently selected from: $C_1$-$C_5$ alkyl.

In some embodiments, $R_4$ is selected from: H, halogen, nitro, $C_1$~$C_8$ alkyl, halogen-substituted $C_1$~$C_8$ alkyl, $C_1$~$C_8$ alkoxy, halogen-substituted $C_1$~$C_8$ alkoxy, —$(CH_2)_x NR_{17}R_{18}$, 5-6 membered heterocyclyl group containing 1-3 N ring atoms and substituted or unsubstituted by 1-5 $R_{19}$, and 5-6 membered heteroaryl containing 1-3 N ring atoms and substituted or unsubstituted by 1-5 $R_{19}$; wherein, x is an integer from 1 to 5.

In some embodiments, $R_4$ is selected from: H, halogen, nitro, $C_1$~$C_4$ alkyl, halogen-substituted $C_1$~$C_4$ alkyl, $C_1$~$C_4$ alkoxy, halogen-substituted $C_1$~$C_4$ alkoxy, —$(CH_2)_x NR_{17}R_{18}$, 5-6 membered heterocyclyl group containing 1-3 N ring atoms and substituted or unsubstituted by 1-3 $R_{19}$, and 5-6-membered heteroaryl containing 1-3 N ring atoms and substituted or unsubstituted by 1-3 $R_{19}$; wherein, x is an integer from 1 to 5.

In some embodiments, $R_4$ is selected from: H, halogen, nitro, $C_1$~$C_4$ alkyl, halogen-substituted $C_1$~$C_4$ alkyl, $C_1$~$C_4$ alkoxy, halogen-substituted $C_1$~$C_4$ alkoxy, —$(CH_2)_x NR_{17}R_{18}$, and 1-3 $R_{19}$ substituted or unsubstituted imidazolyl; wherein, x is 1, 2 or 3;

$R_{17}$ and $R_{18}$ together with the attached nitrogen atom form a piperazinyl substituted or unsubstituted by 1-3 $R_{19}$;

each $R_{19}$ is independently selected from: $C_1$-$C_5$ alkyl.

In some embodiments, $R_4$ is selected from: H, halogen, nitro, methyl, ethyl, propyl, methoxy, ethoxy, propoxy, trifluoromethyl, trifluoroethyl.

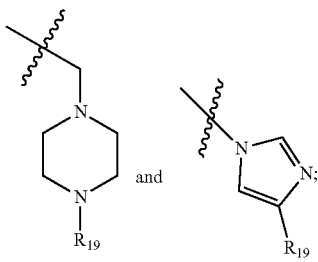

each $R_{19}$ is independently selected from: methyl, ethyl, and propyl.

In some embodiments, $R_6$ and $R_7$ are independently selected from: —$(CH_2)_m NR_8R_9$, —$(CH_2)_n CR_{10}R_{11}R_{12}$, and —$(CH_2)_p OR_{12}$; or $R_6$ and $R_7$ together with the attached nitrogen atom form a 3-15 membered monocyclic ring, fused ring, spiro ring or bridged ring containing 1-3 heteroatoms and substituted or unsubstituted by 1-5 $R_{13}$, wherein, the heteroatoms are selected from: O, N, S;

$R_8$ and $R_9$ are independently selected from: H, and $C_1$-$C_5$ alkyl; or $R_8$ and $R_9$ together with the attached nitrogen atom form a 3-10 membered monocyclic ring, fused ring, spiro ring or bridged ring containing 1-3 heteroatoms and substituted or unsubstituted by 1-5 $R_{13}$, wherein, the heteroatoms are selected from: O, and N;

$R_{10}$ and $R_{11}$ together with the attached carbon atoms form a 3-10 membered monocyclic ring, fused ring, spiro ring or bridged ring containing 1-3 heteroatoms and substituted or unsubstituted by 1-5 $R_{13}$, wherein the heteroatoms are selected from: O, and N;

$R_{12}$ is selected from: H, and $C_1$-$C_5$ alkyl;

each $R_{13}$ is independently selected from: H, $C_1$-$C_5$ alkyl, $C_1$-$C_5$ alkanoyl, hydroxy, hydroxy-substituted $C_1$-$C_5$ alkyl, amino-substituted $C_1$-$C_5$ alkyl, amino-substituted $C_1$-$C_5$ alkoxy, $C_3$-$C_7$ cycloalkyl-substituted $C_1$-$C_3$ alkyl, —$NR_{15}R_{16}$, and 3-10 membered monocyclic ring, fused ring, spiro ring or bridged ring substituted or unsubstituted by 1-5 $R_{14}$ and containing 1-3 heteroatoms, wherein, the heteroatoms are selected from: O, and N;

$R_{14}$, $R_{15}$ and $R_{16}$ are independently selected from: H, and $C_1$-$C_5$ alkyl;

m, n and p are each independently selected from: an integer from 0 to 5.

In some embodiments, $R_6$ and $R_7$ are independently selected from: —$(CH_2)_m NR_8R_9$, and —$(CH_2)_p OR_{12}$; or $R_6$ and $R_7$ together with the attached nitrogen atom form a 1-3 $R_{13}$ substituted or unsubstituted morpholinyl, pyrrolidinyl, piperidinyl or piperazinyl;

$R_8$ and $R_9$ are independently selected from: H, and $C_1$-$C_5$ alkyl; or $R_8$ and $R_9$ together with the attached nitrogen atom form a 1-5 $R_{13}$ substituted or unsubstituted morpholinyl, pyrrolidinyl, piperidinyl or piperazinyl;

$R_{12}$ is selected from: H, and $C_1$-$C_5$ alkyl;

each $R_{13}$ is independently selected from: H, $C_1$-$C_5$ alkyl, $C_1$-$C_5$ alkanoyl, hydroxy, —$NR_{15}R_{16}$, oxetanyl substituted or unsubstituted by 1-2 $R_{14}$, and morpholinyl substituted or unsubstituted by 1-4 $R_{14}$;

$R_{14}$, $R_{15}$ and $R_{16}$ are independently selected from: H, and $C_1$-$C_3$ alkyl;

m and p are independently selected from: 1, 2, 3, 4 and 5.

In some embodiments, $R_5$ is selected from any of the following groups:

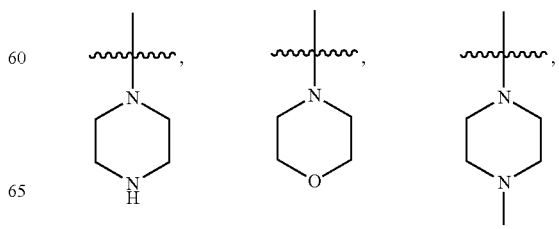

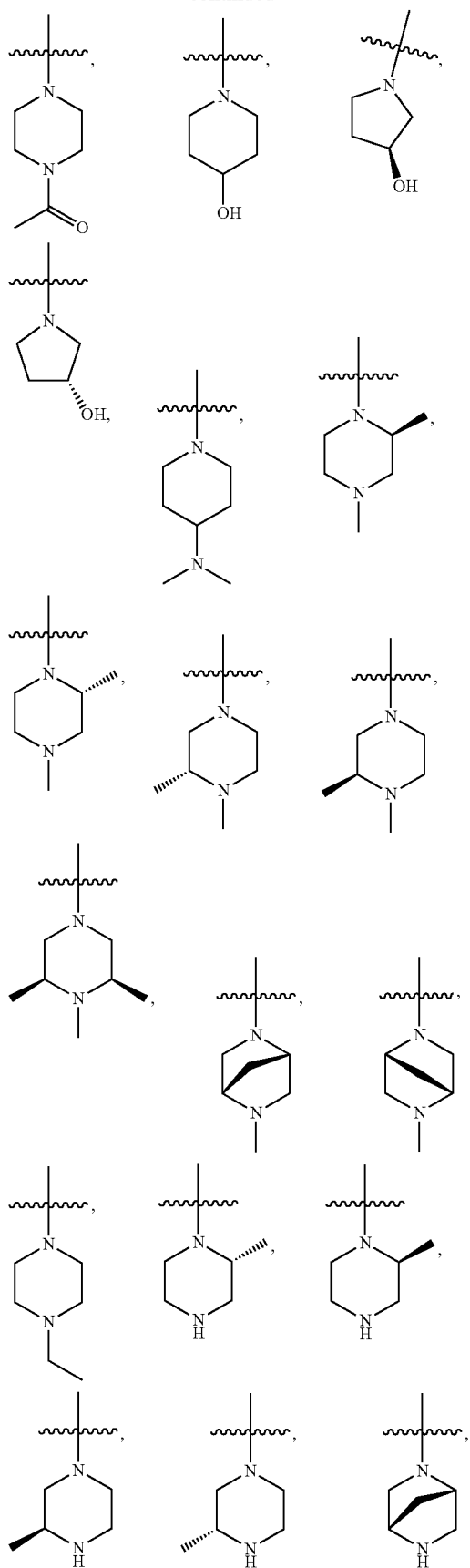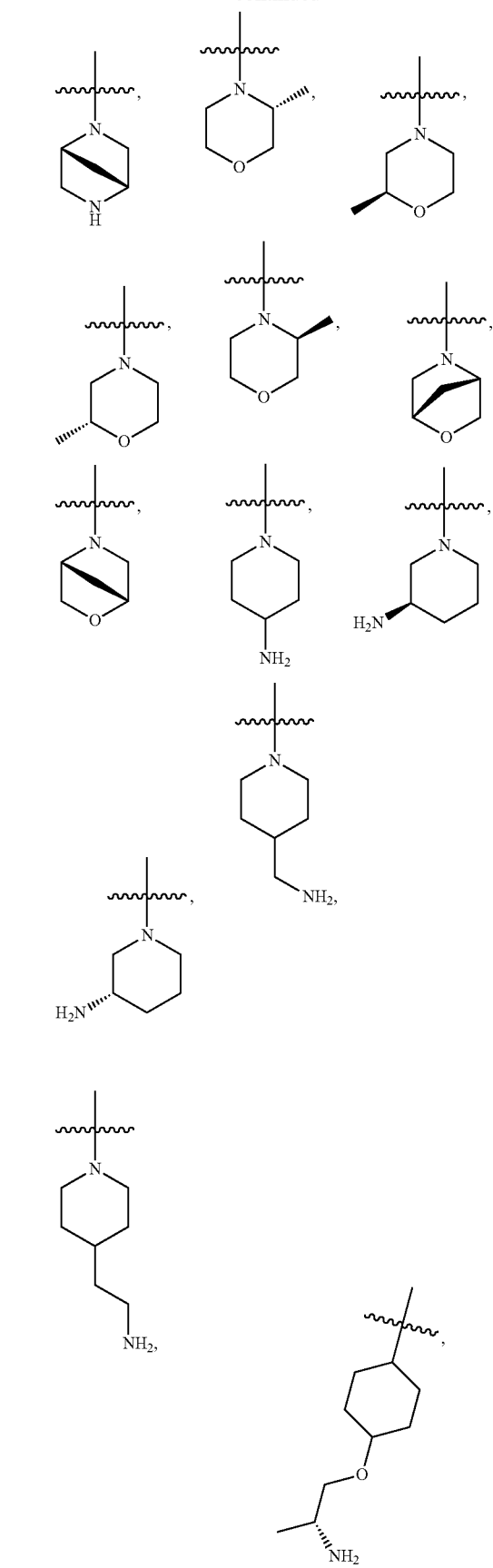

-continued

-continued

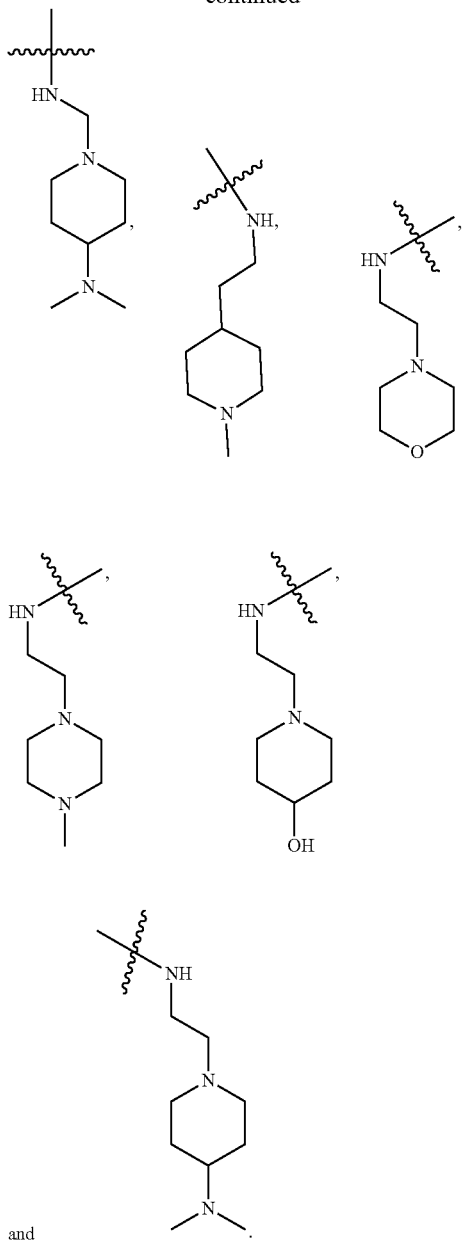

and

In some embodiments, $R_4$ is halogen; $R_5$ is $-NR_6R_7$;

$R_6$ and $R_7$ are independently selected from: $-(CH_2)_mNR_8R_9$, and $-(CH_2)_pOR_{12}$; or $R_6$ and $R_7$ together with the attached nitrogen atom form a 1-3 $R_{13}$ substituted or unsubstituted morpholinyl, pyrrolidinyl, piperidinyl or piperazinyl;

$R_8$ and $R_9$ are independently selected from: H, and $C_1$-$C_3$ alkyl; or $R_8$ and $R_9$ together with the attached nitrogen atom form a 1-2 $R_{13}$ substituted or unsubstituted morpholinyl, pyrrolidinyl, piperidinyl or piperazinyl;

$R_{12}$ is selected from: H, and $C_1$-$C_3$ alkyl;

each $R_{13}$ is independently selected from: H, $C_1$-$C_3$ alkyl, acetyl, hydroxyl, $-NR_{15}R_{16}$, oxetanyl, and morpholinyl;

$R_{15}$ and $R_{16}$ are independently selected from: H, and $C_1$-$C_3$ alkyl;

m and p are independently selected from: 2, 3 and 4.

In some embodiments, $R_4$ is Cl, $R_5$ is selected from:

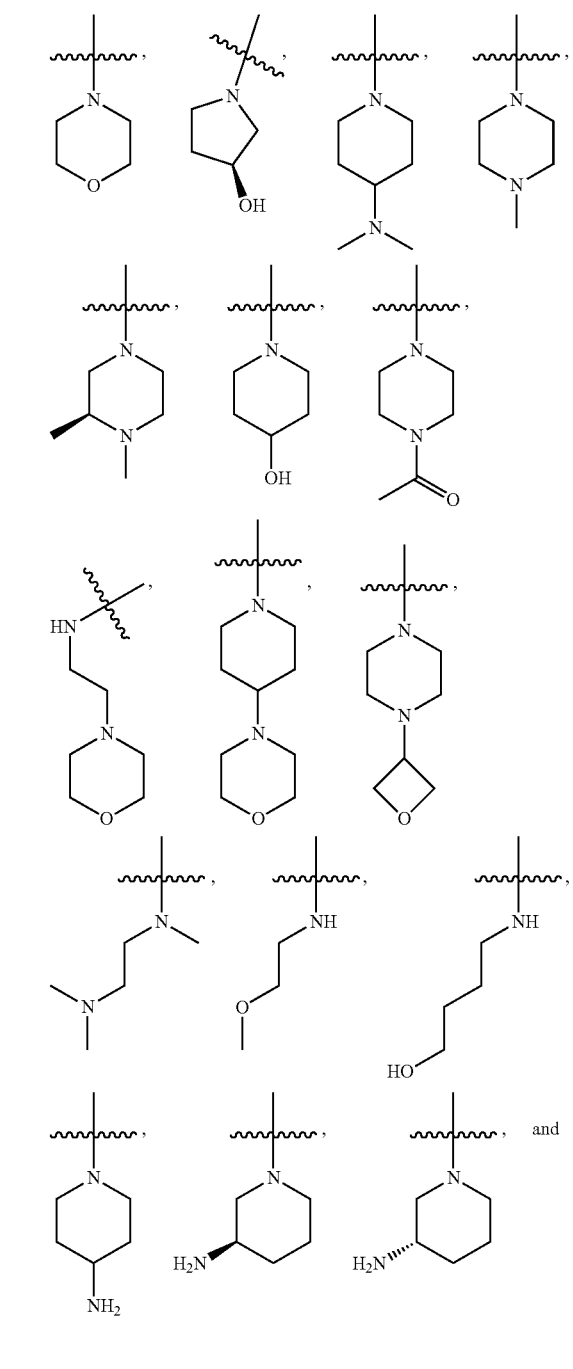

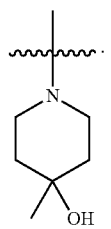

In some embodiments, $R_4$ is selected from: H, halogen, methyl, methoxy, trifluoromethyl, nitro, and

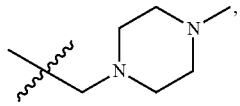 [SMILES: *CN1CCN(C)CC1]

and $R_5$ is

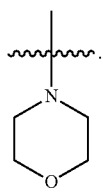

In some embodiments, $R_4$ is selected from H, and

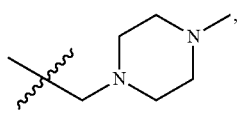 [SMILES: *CN1CCN(C)CC1]

and $R_5$ is selected from

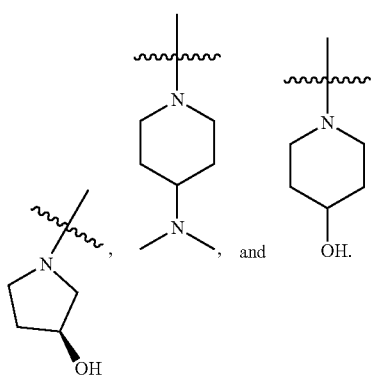

In some embodiments, R4 is

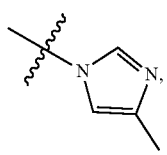

and $R_5$ is selected from

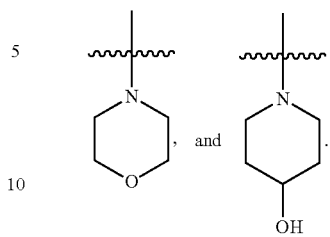

In some embodiments, $R_1$ is selected from: $C_1$~$C_{10}$ alkyl.
In some embodiments, $R_1$ is selected from: $C_1$~$C_4$ alkyl.
In some embodiments, $R_1$ is selected from: methyl, ethyl, isopropyl, and tert-butyl.
In some embodiments, $R_2$ is selected from: H, halogen, $C_1$-$C_{10}$ alkyl, and halogen-substituted $C_1$-$C_{10}$ alkyl.
In some embodiments, $R_2$ is selected from: H, halogen, $C_1$-$C_4$ alkyl, halogen-substituted $C_1$-$C_4$ alkyl, and $C_1$-$C_4$ alkoxy.
In some embodiments, $R_2$ is selected from: hydrogen, fluorine, methyl, ethyl, isopropyl, tert-butyl, difluoromethyl, difluoroethyl, trifluoromethyl and trifluoroethyl.
In some embodiments, $R_3$ is selected from: H, difluoromethyl, difluoroethyl, trifluoromethyl and trifluoroethyl.
In some embodiments, the Alkynylphenylbenzamide compounds have the structure shown in Formula (II):

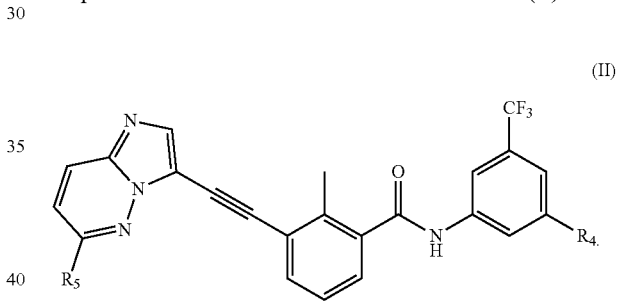

Another object of the present disclosure is to provide an application of the above-mentioned Alkynylphenylbenzamide compounds or their pharmaceutically acceptable salts or stereoisomers or prodrug molecules in the preparation of TRK inhibitors.

Another object of the present disclosure is to provide an application of the above-mentioned Alkynylphenylbenzamide compounds or their pharmaceutically acceptable salts or stereoisomers or prodrug molecules in the preparation of medicaments for preventing and/or treating the diseases mediated by TRK tyrosine kinases.

In some embodiments, the disease mediated by TRK tyrosine kinase is tumor, preferably non-small cell lung cancer, breast cancer, colon cancer, prostate cancer, thyroid cancer, malignant melanoma, nerve blastoma and breast-like secretory carcinoma.

Another object of the present disclosure is to provide a pharmaceutical composition for preventing and/or treating tumors, comprising an active ingredient and a pharmaceutically acceptable adjuvant, wherein the active ingredient comprises the above-mentioned Alkynylphenylbenzamide compounds or their pharmaceutically acceptable salts or stereoisomers or prodrug molecules.

The Alkynylphenylbenzamide compounds provided by the present disclosure have strong inhibitory activity on TRKs kinase, and have strong inhibitory activity on the proliferation of wild-type and drug-resistant cells of Ba/F3-TRKs stable strain. It can be used for preparation of medicaments for preventing or treating diseases mediated by TRK tyrosine kinase, such as non-small cell lung cancer, breast cancer, colon cancer, prostate cancer, thyroid cancer, malignant melanoma, nerve Blastoma and breast-like secretory carcinoma. It also has good pharmacokinetic properties and low toxicity.

DETAILED DESCRIPTION OF THE INVENTION

Figure 1:
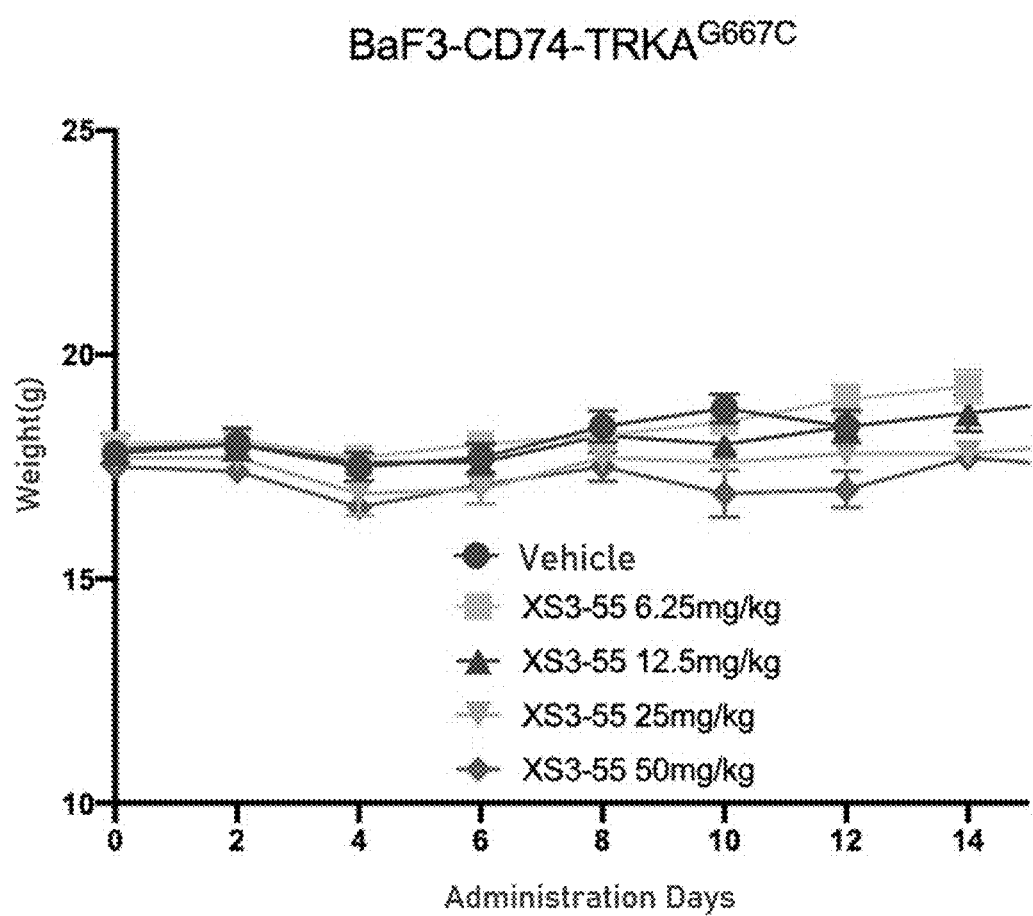
FIG. 1 shows the in vivo antitumor activity of compound XS3-55.

The experimental methods without indicating specific conditions in the following examples of the present disclosure are usually in accordance with conventional conditions, or in accordance with the conditions suggested by the manufacturer. Various common chemical reagents used in the examples are all commercially available products.

Unless otherwise defined, all technical and scientific terms as used herein have the same meanings as those commonly understood by one skilled in the art of the present disclosure. The terms used in the description of the present disclosure are for description of the specific embodiments only and are not intended to limit the present disclosure.

The terms "comprising" and "having" and any variations thereof of the present disclosure are intended to cover a non-exclusive inclusion. For example, a process, method, apparatus, product or device comprising a series of steps is not limited to the steps or modules listed, but optionally also includes steps not listed, or optionally includes other steps inherent to the process, method, product, or apparatus.

The "plurality" mentioned in the present disclosure means two or more. "And/or", which describes the association relationship of the associated objects, means that there can be three kinds of relationships, for example, A and/or B, which can mean that A exists alone, A and B exist at the same time, and B exists alone. The character "/" generally indicates that the associated objects are an "or" relationship.

In the compounds of the present disclosure, when any variable (eg, $R_{10}$, $R_{11}$, etc.) occurs more than once in any component, its definition at each occurrence is independent of the definition at each other occurrences. Likewise, combinations of substituents and variables are permissible as long as such combinations stabilize the compound. The line drawn into a ring system from a substituent indicates that the indicated bond may be attached to any substitutable ring atom. If the ring system is polycyclic, it means that such bonds are only attached to any suitable carbon atoms adjacent to the ring. It should be appreciated that an ordinary skilled in the art can select substituents and substitution patterns for the compounds of the present disclosure to provide compounds that are chemically stable and readily synthesized from the available starting materials by the methods described below. If a substituent itself is substituted by more than one group, it should be understood that these groups may be on the same carbon atom or on different carbon atoms, so long as the structure is stabilized.

The term "alkyl" in the present disclosure is meant to include branched and straight chain saturated aliphatic hydrocarbon groups having the specified number of carbon atoms. For example, the definition of "$C_1$-$C_{20}$" in "$C_1$-$C_{20}$ alkyl" includes groups having 1, 2, 3, 4, 5 . . . or 20 carbon atoms arranged in a straight or branched chain. The term "cycloalkyl" refers to a monocyclic saturated aliphatic hydrocarbon group having the specified number of carbon atoms. For example, "$C_3$~$C_7$ cycloalkyl" includes cyclopropyl, cyclobutyl, cyclopentyl, cyclohexyl or cycloheptyl and the like.

The term "alkoxy" as used herein refers to a group in which an alkyl group is directly attached to oxygen, i.e. a group with an —O-alkyl structure, such as —$OCH_3$, —$OCH_2CH_3$, —$OCH_2CH_2CH_3$, —$O$—$CH_2CH(CH_3)_2$, —$OCH_2CH_2CH_2CH_3$, —$O$—$CH(CH_3)_2$, etc.

The term "heterocyclyl" as used herein refers to a non-aromatic heterocyclic group containing one or more heteroatoms selected from O, N and S, for example: piperidinyl, tetrahydropyrrolyl (pyrrolidinyl), morpholino, piperazinyl, etc. The attachment of heterocyclic substituents can be achieved by carbon atoms or heteroatoms.

The term "heteroaryl" as used herein refers to an aromatic ring containing one or more heteroatoms selected from O, N or S. Heteroaryl groups within the scope of the present disclosure include, but not limited to: quinolinyl, pyrazolyl, pyrrolyl, thienyl, furanyl, pyridyl, pyrimidinyl, pyrazinyl, triazolyl, imidazolyl, oxazolyl, isoxazolyl, pyridazinyl, benzoyl Furanyl, benzothienyl, benzoxazole, indolyl, etc.; "heteroaryl" can also be understood to include the N-oxide derivatives of any nitrogen-containing heteroaryl groups. The attachment of heteroaryl substituents can be through carbon atoms or through heteroatoms.

The term "substituted" as used herein refers to the replacement of a hydrogen group in a particular structure with a group of the designated substituent.

As understood by the skilled in the art, "halogen" as used herein means chlorine, fluorine, bromine and iodine.

The present disclosure comprises free forms of compounds of Formula (I) or Formula (II), as well as their pharmaceutically acceptable salts and stereoisomers and prodrug molecules. The term "free form" refers to compound in non-salt form. The pharmaceutically acceptable salts" include not only exemplary salts of the particular compounds described herein, but also typical pharmaceutically acceptable salts of all compounds of Formula (I) or Formula (II) in free form. The free forms of specific salts of the compounds can be isolated using the techniques known in the art. For example, the free form can be regenerated by treating the salt with an appropriate dilute aqueous base such as dilute aqueous NaOH, dilute aqueous potassium carbonate, dilute aqueous ammonia, and dilute aqueous sodium bicarbonate. The free forms differ somewhat from their respective salt forms in certain physical properties such as solubility in polar solvents, but for the purposes of the invention, such salts of acid or base are otherwise pharmaceutically equivalent to their respective free forms.

The pharmaceutically acceptable salts of the present disclosure can be synthesized from the compounds containing a basic or acidic moiety in the present disclosure by conventional chemical methods. Generally, salts of basic compounds can be prepared by ion exchanged chromatography or by reacting the free base with a stoichiometric or excess amount of inorganic or organic acid in the desired salt form in a suitable solvent or combination of solvents. Similarly, salts of acidic compounds can be formed by reaction with a suitable inorganic or organic base.

Accordingly, pharmaceutically acceptable salts of the compounds of the present disclosure include conventional non-toxic salts of the compounds of the present disclosure formed by reacting a basic compound of the present disclosure with inorganic or organic acid. For example, conventional non-toxic salts include those derived from inorganic acids such as hydrochloric acid, hydrobromic acid, sulfuric acid, sulfamic acid, phosphoric acid, and nitric acid, etc. They also include those derived from organic acids such as acetic acid, propionic acid, succinic acid, glycolic acid, hard Fatty acid, lactic acid, malic acid, tartaric acid, citric acid, ascorbic acid, pamoic acid, maleic acid, hydroxymaleic acid, phenylacetic acid, glutamic acid, benzoic acid, salicylic acid, p-aminobenzenesulfonic acid, 2-acetoxy-benzoic acid, fumaric acid, benzenesulfonic acid, toluenesulfonic acid, methanesulfonic acid, ethanedisulfonic acid, oxalic acid, isethionic acid, and trifluoroacetic acid, etc.

If the compounds of the present disclosure are acidic, the appropriate "pharmaceutically acceptable salts" refers to the salts prepared with pharmaceutically acceptable non-toxic bases including inorganic and organic bases. The salts derived from inorganic bases include aluminum, ammonium, calcium, copper, iron, ferrous, lithium, magnesium, manganese, manganous, potassium, sodium, zinc, etc. Ammonium salts, calcium salts, magnesium salts, potassium salts, and sodium salts are particularly preferred. The salts derived from pharmaceutically acceptable organic non-toxic bases include salts of primary, secondary and tertiary amines. Substituted amines include naturally occurring substituted amines, cyclic amines and basic ion exchange resins such as Amino acid, betaine, caffeine, choline, N,N'-dibenzylethylenediamine, diethylamine, 2-diethylaminoethanol, 2-dimethylaminoethanol, aminoethanol, ethanolamine, ethyl Diamine, N-ethylmorpholine, N-ethylpiperidine, Glucosamine, Glucosamine, Histidine, Hydroxocobalamin, Isopropylamine, Lysine, Methylglucamine, Morpholine, Piperazine, Piperidine, quack, polyamine resin, procaine, purine, theobromine, triethylamine, trimethylamine, tripropylamine, tromethamine, etc.

The preparation of the pharmaceutically acceptable salts described above and other typical pharmaceutically acceptable salts was described in more detail by Berg et al., in "Pharmaceutical Salts," J. Pharm. Sci. 1977:66:1-19.

The following are specific examples to further describe the present disclosure in detail.

EXAMPLE 1: PREPARATION OF 3-(IMIDAZO [1,2-B]PYRIDAZIN-3-YLETHYNYL)-2-METHYL-N-(3-((4-METHYLPIPERAZIN-1-YL) METHYL)-5-(TRIFLUOROMETHYL)PHENYL) BENZAMIDE (DESIGNATED AS XS116)

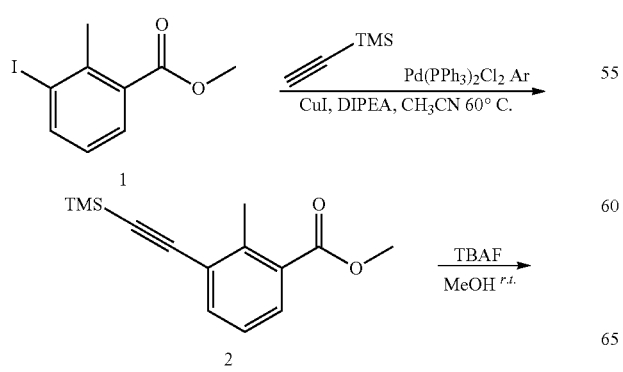

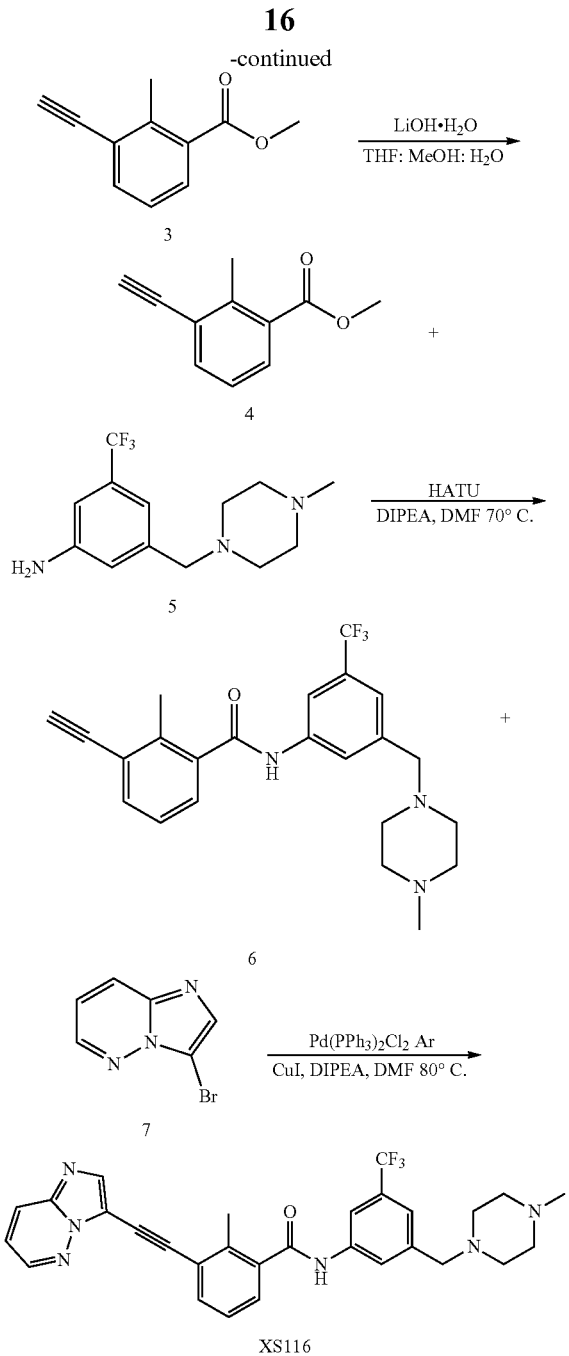

Step 1: Preparation of methyl 2-methyl-3-((trimethylsilyl)ethynyl)benzoate (Compound 2)

In a 500 mL three-necked flask, 10 g (36 mmol) of Compound 1, 689 mg (3.6 mmol) of cuprous iodide, 1.27 g (1.8 mmol) of bis(triphenylphosphine)palladium dichloride, 150 mL anhydrous acetonitrile and 9.3 g (72 mmol) of N,N-diisopropylethylamine were added to react under Ar in a closed system. Then 10.6 g (108 mmol) of trimethylsilylacetylene was injected with a syringe, and the mixture was stirred at 60° C. for 6 hours. The reaction solution was filtered through celite, and the solvent was spin-dried to obtain a black mixture, which was directly used in the next reaction.

Step 2: Preparation of methyl 2-ethynyl-2-methylbenzoate (Compound 3)

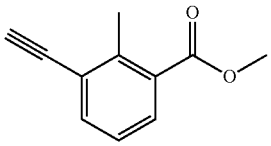

The crude product in the previous step was dissolved in methanol, and added with about 20 mL of 1 mol/L tetrabutylammonium fluoride solution in tetrahydrofuran, and the mixture was stirred at room temperature for 2 hours. The reaction system was spin-dried, and 4 g of yellow-brown oil was obtained by column chromatography (total yield of the two steps was 63%).

¹H NMR (400 MHz, DMSO-d₆) δ 7.80 (s, 1H), 7.78 (s, 1H), 7.58 (s, 1H), 4.27 (s, 1H), 3.85 (s, 3H), 2.37 (s, 3H). LC-MS (ESI) m/z 175.5 [M+H]⁺.

Step 3: Preparation of 3-ethynyl-2-methylbenzoic acid (Compound 4)

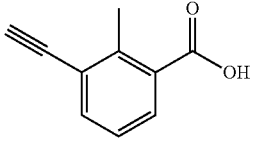

1.5 g (9 mmol) of Compound 3 was dissolved in a mixed solvent of tetrahydrofuran, methanol and water with a volume ratio of 10:1:5, then 1.8 g (40 mmol) of lithium hydroxide hydrate was added, and the mixture was stirred at 60° C. for 1 hour. The reaction system was filtered and spin-dried, and then was added with 4M hydrochloric acid solution until the system became acidic. At this time a white solid is precipitated, which was collected by filtration, and dried to obtain 900 mg of white solid (yield: 65%).

¹H NMR (400 MHz, DMSO-d₆) δ 13.09 (s, 1H), 7.77 (dd, J=7.8, 0.9 Hz, 1H), 7.62 (d, J=7.6 Hz, 1H), 7.29 (t, J=7.7 Hz, 1H), 4.47 (s, 1H), 2.61 (s, 3H). LC-MS (ESI) m/z 158.9 [M−H]⁻.

Step 4: Preparation of 3-Ethynyl-2-methyl-N-(3-((4-methylpiperazin-1-yl)methyl)-5-(trifluoromethyl)phenyl)benzamide (Compound 6)

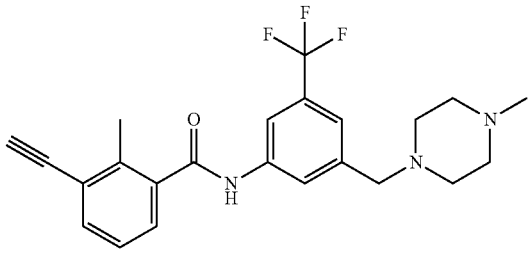 [SMILES: C#Cc1cccc(C(=O)Nc2cc(CN3CCN(C)CC3)cc(C(F)(F)F)c2)c1C]

2.3 g of Compound 4 and 3.4 g of Compound 5 were dissolved in 40 mL of N,N-dimethylformamide (DMF), added with 9.12 g (24 mmol) of 2-(7-Azabenzotriazole)-N,N,N',N'-tetramethylurea hexafluorophosphate (HATU) and 2.3 g (18 mmol) of N,N-diisopropylethyl acetate amine; and the mixture was heated and stirred at 70° C. for 2 hours. The reaction system was spin-dried, and added with water, extracted with ethyl acetate, rinsed with water, dried with anhydrous sodium sulfate. The solvent was spin-dried, and 3.4 g of yellow oil was obtained by column chromatography (yield: 70%).

¹H NMR (400 MHz, DMSO-d₆) δ 10.52 (s, 1H), 8.17 (s, 1H), 8.10 (s, 1H), 8.00 (d, J=8.0 Hz, 1H), 7.91 (m, 1H), 7.47 (d, J=8.0 Hz, 1H), 7.34 (s, 1H), 4.51 (s, 1H), 3.53 (s, 2H), 2.46 (s, 3H), 2.39 (s, 4H), 2.33 (s, 4H), 2.15 (s, 3H). LC-MS (ESI) m/z 416.3 [M+H]⁺.

Step 5: Preparation of 3-(imidazo[1,2-b]pyridazin-3-ylethynyl)-2-methyl-N-(3-((4-methylpiperazin-1-yl)methyl))-5-(trifluoromethyl)phenyl)benzamide (XS116)

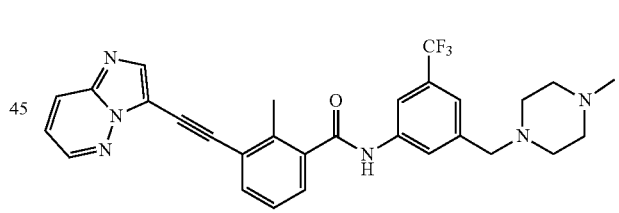

210 mg (0.51 mmol) of Compound 6 and 120 mg (0.61 mmol) Compound 7 were dissolved in 10 mL of anhydrous N,N-dimethylformamide (DMF), then added with 19 mg (0.1 mmol) of cuprous iodide, 35 mg (0.05 mmol) of bis(triphenylphosphine)palladium dichloride and 131 mg (1.02 mmol) of N,N-diisopropylethylamine, reacted under Ar in a closed system. The mixture was heated and stirred at 80° C. and reacted overnight. The reaction solution was filtered through celite, the solvent was spin-dried, and 70 mg of yellow-white solid was obtained by column chromatography (yield: 26%).

¹H NMR (400 MHz, Chloroform-d) δ 8.50 (dd, J=4.4, 1.6 Hz, 1H), 8.07 (s, 1H), 8.02 (dd, J=9.2, 1.7 Hz, 1H), 7.94 (s, 1H), 7.81 (d, J=4.5 Hz, 2H), 7.73 (dd, J=7.7, 1.4 Hz, 1H), 7.50 (d, J=7.8 Hz, 1H), 7.41 (s, 1H), 7.32 (t, J=7.7 Hz, 1H), 7.16 (dd, J=9.2, 4.4 Hz, 1H), 3.62 (s, 2H), 2.76 (s, 3H), 2.64 (s, 8H), 2.41 (s, 3H). LC-MS (ESI) m/z 533.3 [M+H]⁺.

EXAMPLE 2: PREPARATION OF 3-(IMIDAZO[1,2-A]PYRIMIDIN-3-YLETHYNYL)-2-METHYL-N-(3-((4-METHYLPIPERAZIN-1-YL)METHYL)-5-(TRIFLUOROMETHYL)PHENYL)BENZAMIDE (DESIGNATED AS XS2-161)

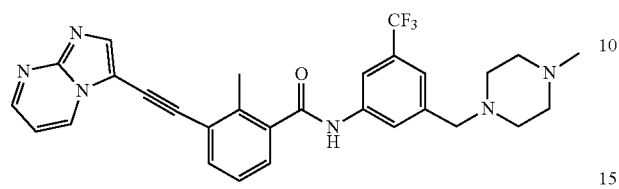

The synthetic method is according to Example 1.

$^1$H NMR (400 MHz, Chloroform-d) δ 9.06 (s, 1H), 8.64 (dd, J=4.1, 2.0 Hz, 1H), 8.60 (dd, J=6.8, 2.0 Hz, 1H), 8.12 (s, 1H), 8.03 (s, 1H), 7.90 (s, 1H), 7.58 (dd, J=7.8, 1.3 Hz, 1H), 7.50 (dd, J=7.8, 1.3 Hz, 1H), 7.40 (s, 1H), 7.25 (t, J=7.7 Hz, 1H), 7.09 (dd, J=6.8, 4.1 Hz, 1H), 3.70 (s, 2H), 3.11 (q, J=7.3 Hz, 4H), 2.91 (d, J=5.0 Hz, 4H), 2.73 (s, 3H), 2.61 (s, 3H). LC-MS (ESI) m/z 533.2 [M+H]$^+$.

EXAMPLE 3: PREPARATION OF 3-(IMIDAZO[1,2-B]PYRIDAZIN-3-YLETHYNYL)-2-METHYL-N-(3-(TRIFLUOROMETHYL)PHENYL)BENZAMIDE (DESIGNATED AS XS2-106)

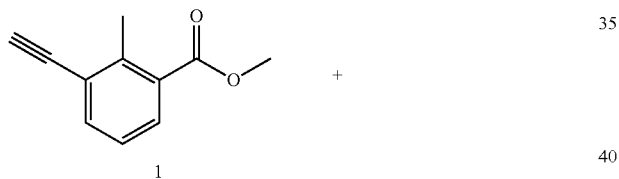

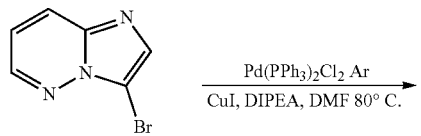

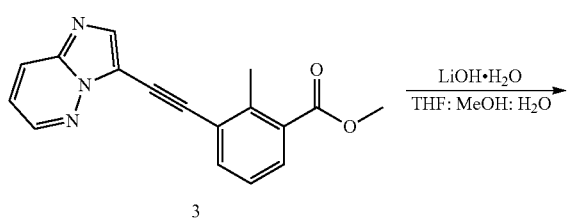

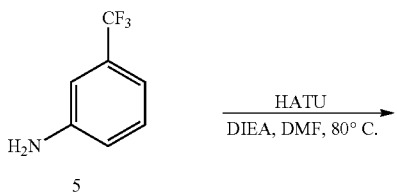
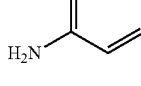

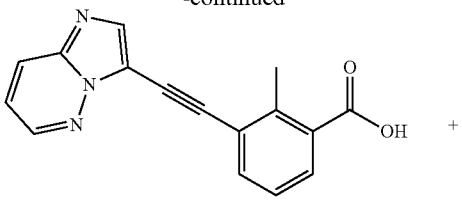

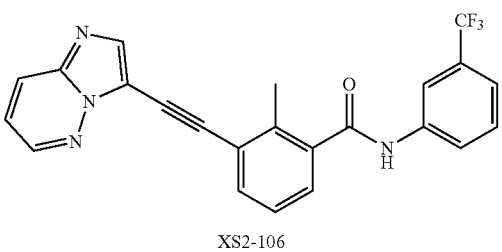

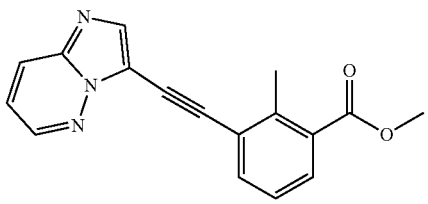 [SMILES: COC(=O)c1cccc(C#Cc2cnc3cccnn23)c1C]

Step 1: Preparation of methyl 3-(imidazo[1,2-b]pyridazin-3-ylethynyl)-2-methylbenzoate (Compound 3)

2.5 g (14 mmol) of Compound 1 and 3.4 g (17 mmol) of Compound 2 were dissolved in 40 mL of anhydrous N,N-dimethylformamide (DMF), and then added with 533 mg (2.8 mmol) of cuprous iodide, 982 mg (1.4 mmol) of bis(triphenylphosphine)palladium and 3.6 g (28 mmol) of N,N-diisopropylethylamine, and then reacted under Ar in a closed system. The mixture was heated and stirred at 80° C. and reacted overnight. The reaction solution was filtered through celite, the solvent was spin-dried, and 1.38 g of yellow powdery solid was obtained by column chromatography (yield: 34%).

$^1$H NMR (400 MHz, DMSO-d$_6$) δ 8.74 (d, J=4.3 Hz, 1H), 8.27 (d, J=8.9 Hz, 2H), 7.83 (d, J=7.7 Hz, 1H), 7.75 (d, J=7.5 Hz, 1H), 7.44-7.41 (m, 1H), 7.39 (d, J=7.6 Hz, 1H), 3.85 (s, 3H), 2.76 (s, 3H). LC-MS (ESI) m/z 292.3 [M+H]$^+$.

Step 2: Preparation of 3-(imidazo[1,2-b]pyridazin-3-ylethynyl)-2-methylbenzoic acid (Compound 4)

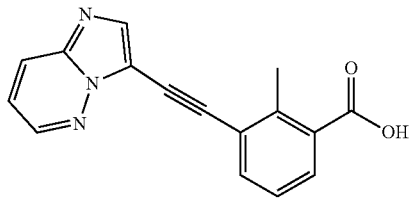 [SMILES: Cc1c(C#Cc2cnc3cccnn23)cccc1C(=O)O]

1.38 g (4.7 mmol) of Compound 3 was dissolved in a mixed solvent of tetrahydrofuran, methanol and water with a volume ratio of 10:1:5, then 995 mg (24 mmol) of lithium hydroxide hydrate was added, and the mixture was stirred at 60° C. for 1 hour. The reaction system was filtered and spin-dried, and then added with 4M of hydrochloric acid solution until the system became acidic. At this time a solid is precipitated, which was collected by filtration, and dried to obtain 1.05 g of yellow solid (yield: 81%).

$^1$H NMR (400 MHz, DMSO-$d_6$) δ 13.14 (s, 1H), 8.72 (d, J=3.9 Hz, 1H), 8.32-8.19 (m, 2H), 7.83 (d, J=7.6 Hz, 1H), 7.75 (d, J=7.3 Hz, 1H), 7.44-7.34 (m, 2H), 2.76 (s, 3H). LC-MS (ESI) m/z 276.8 [M−H]$^-$.

Step 3: Preparation of 3-(imidazo[1,2-b]pyridazin-3-ylethynyl)-2-methyl-N-(3-(trifluoromethyl)phenyl)benzamide (XS2-106)

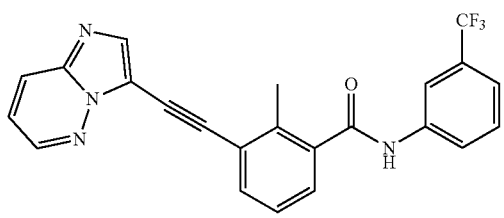 [SMILES: Cc1c(C#Cc2cnc3cccnn23)cccc1C(=O)Nc1cccc(C(F)(F)F)c1]

100 mg (0.36 mmol) of Compound 4 and 48 mg (0.3 mmol) of Compound 5 were dissolved in 10 mL of N,N-dimethylformamide (DMF), then added with 137 mg (0.36 mmol) of 2-(7-Azabenzotriazole)-N,N,N',N'-tetramethyl-urea hexafluorophosphate (HATU) and 77 mg (0.6 mmol) of N,N-diisopropylethyl acetate amine; and the mixture was heated and stirred at 80° C. and reacted overnight. The reaction system was spin-dried, and 51 mg of yellow-white solid was obtained by column chromatography (yield 40%).

$^1$H NMR (400 MHz, Chloroform-d) δ 8.51 (d, J=4.1 Hz, 1H), 8.03 (dd, J=23.3, 14.3 Hz, 3H), 7.89 (d, J=7.4 Hz, 1H), 7.73 (d, J=6.6 Hz, 2H), 7.50 (ddd, J=24.8, 16.6, 7.8 Hz, 3H), 7.32 (t, J=7.7 Hz, 1H), 7.17 (dd, J=9.1, 4.4 Hz, 1H), 2.76 (s, 3H). LC-MS (ESI) m/z 419.2 [M−H]$^-$.

EXAMPLE 4: PREPARATION OF N-(3-FLUORO-5-(TRIFLUOROMETHYL)PHENYL)-3-(IMIDAZO[1,2-B]PYRIDAZIN-3-YLETHYNYL)-2-METHYLBENZENE FORMAMIDE (DESIGNATED AS XS2-109)

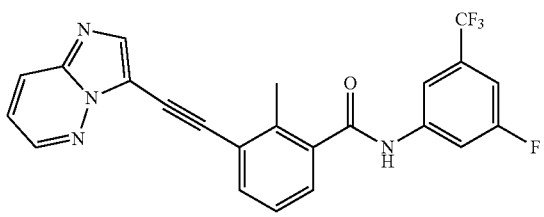 [SMILES: Cc1c(C#Cc2cnc3cccnn23)cccc1C(=O)Nc1cc(F)cc(C(F)(F)F)c1]

The synthetic method is according to Example 3.

$^1$H NMR (400 MHz, Chloroform-d) δ 8.53 (d, J=4.2 Hz, 1H), 8.08 (s, 2H), 7.91 (d, J=10.1 Hz, 1H), 7.81 (s, 1H), 7.74 (d, J=7.8 Hz, 1H), 7.59 (s, 1H), 7.50 (d, J=7.5 Hz, 1H), 7.33 (t, J=7.7 Hz, 1H), 7.19 (s, 1H), 7.16 (d, J=8.2 Hz, 1H), 2.75 (s, 3H). LC-MS (ESI) m/z 437.6 [M−H]$^-$.

EXAMPLE 5: PREPARATION OF N-(3-CHLORO-5-(TRIFLUOROMETHYL)PHENYL)-3-(IMIDAZO[1,2-B]PYRIDAZIN-3-YLETHYNYL)-2-METHYLBENZENE FORMAMIDE (DESIGNATED AS XS2-112)

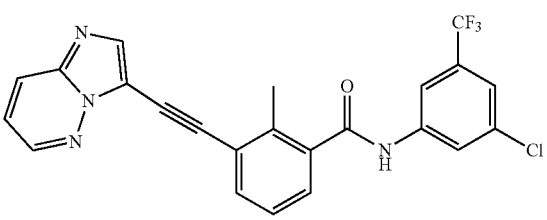 [SMILES: Cc1c(C#Cc2cnc3cccnn23)cccc1C(=O)Nc1cc(Cl)cc(C(F)(F)F)c1]

The synthetic method is according to Example 3.

$^1$H NMR (400 MHz, Chloroform-d) δ 8.50 (dd, J=4.4, 1.5 Hz, 1H), 8.06 (d, J=4.2 Hz, 2H), 8.01 (dd, J=9.2, 1.6 Hz, 1H), 7.85 (s, 1H), 7.80 (s, 1H), 7.74 (d, J=6.7 Hz, 1H), 7.48 (d, J=6.9 Hz, 1H), 7.44 (s, 1H), 7.32 (t, J=7.7 Hz, 1H), 7.16 (dd, J=9.2, 4.4 Hz, 1H), 2.75 (s, 3H). LC-MS (ESI) m/z 455.5 [M+H]$^+$.

EXAMPLE 6: PREPARATION OF 2-METHYL-3-((6-MORPHOLINIMIDAZO[1,2-B]PYRIDAZIN-3-YL)ETHYNYL)-N-(3-(TRIFLUOROMETHYL) BENZENE BASE) BENZAMIDE (DESIGNATED AS XS3-23)

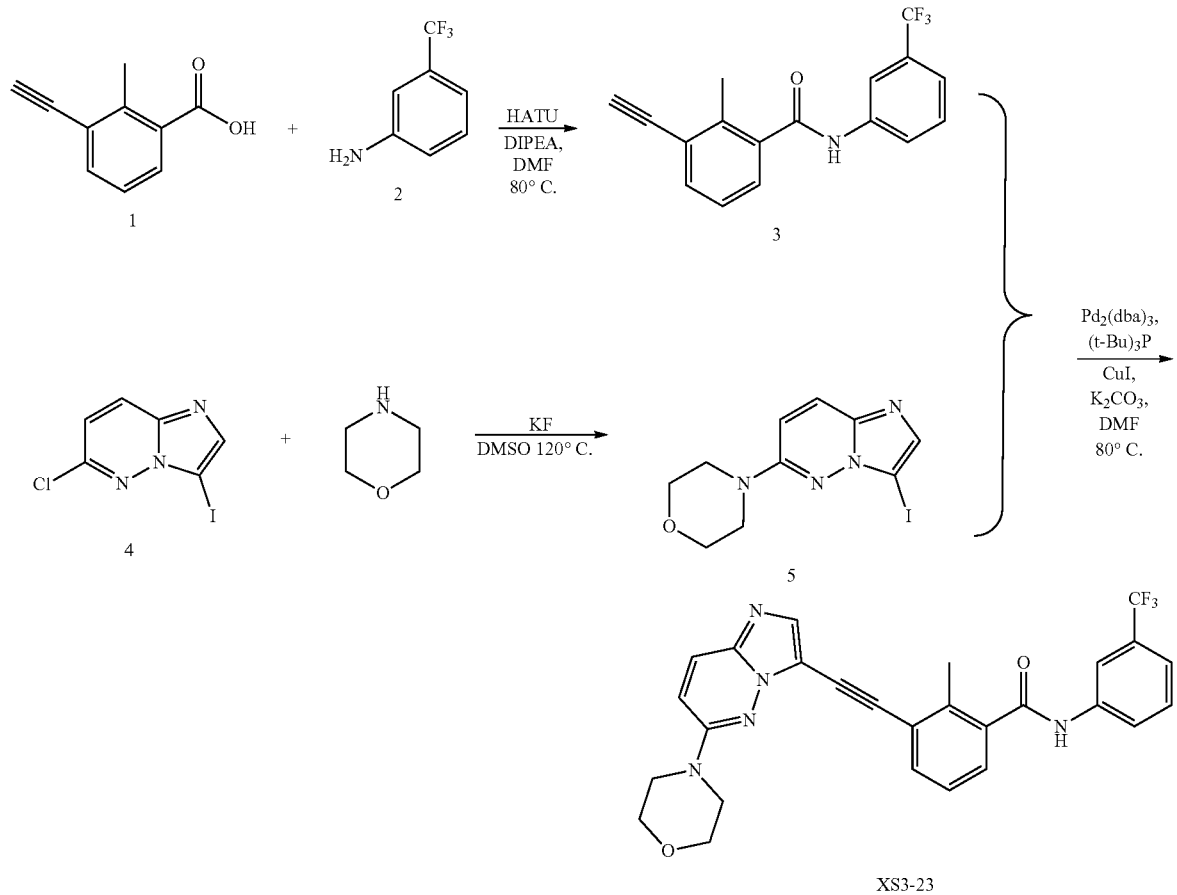

Step 1: Preparation of 3-Ethynyl-2-methyl-N-(3-(trifluoromethyl)-phenyl) benzamide (Compound 3)

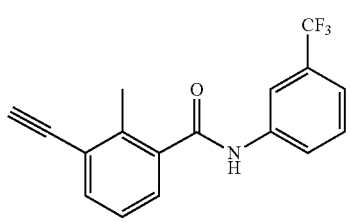 [SMILES: C#Cc1cccc(C(=O)Nc2cccc(C(F)(F)F)c2)c1C]

120 mg (0.74 mmol) of Compound 1 and 101 mg (0.62 mmol) of Compound 2 were dissolved in 15 mL of N,N-dimethylformamide (DMF), and then added with 353 mg (0.93 mmol) of 2-(7-Azabenzotriazole)-N,N,N',N'-tetramethylurea hexafluorophosphate (HATU) and 160 mg (1.24 mmol) of N,N-diisopropylethyl acetate amine; and then the mixture was heated and stirred at 80° C. for 2 hours. The reaction system was spin-dried, and added with water, and then extracted with ethyl acetate, rinsed with water, dried with anhydrous sodium sulfate. The solvent was spin-dried, and 150 mg of yellow oil was obtained by column chromatography (yield: 80%).

$^1$H NMR (400 MHz, DMSO-d$_6$) δ 10.75 (s, 1H), 8.26 (d, J=2.0 Hz, 1H), 7.95-7.90 (m, 1H), 7.63-7.58 (m, 2H), 7.53 (dd, J=7.7, 1.4 Hz, 1H), 7.49-7.45 (m, 1H), 7.35 (t, J=7.7 Hz, 1H), 4.52 (s, 1H), 2.47 (s, 3H). LC-MS (ESI) m/z 304.1 [M+H]$^+$.

Step 2: Preparation of 4-(3-iodoimidazo[1,2-b]pyridazin-6-yl)morpholine (Compound 5)

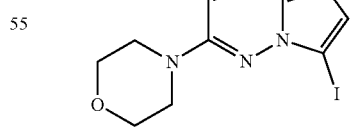

300 mg (1.07 mmol) of Compound 4 was dissolved in 15 mL of dimethyl sulfoxide (DMSO), and then added with 280 mg (3.22 mmol) of morpholine and 744 mg (12.84 mg) of potassium fluoride. The mixture was heated and stirred at 120° C. for 3 hours. The reaction system was filtrated and spin-dried, and 260 mg of yellow powdery solid was obtained by column chromatography (yield: 74%).

$^1$H NMR (400 MHz, Chloroform-d) δ 7.70 (d, J=9.8 Hz, 1H), 7.64 (s, 1H), 6.82 (d, J=9.9 Hz, 1H), 3.89 (t, J=4.8 Hz, 4H), 3.57 (t, J=4.9 Hz, 4H). LC-MS (ESI) m/z 331.0 [M+H]$^+$.

Step 3: Preparation of 2-Methyl-3-(6-morpholino-imidazo[1,2-b]pyridazin-3-yl)ethynyl)-N-(3-(trifluoromethyl)phenyl)) benzamide (XS3-23)

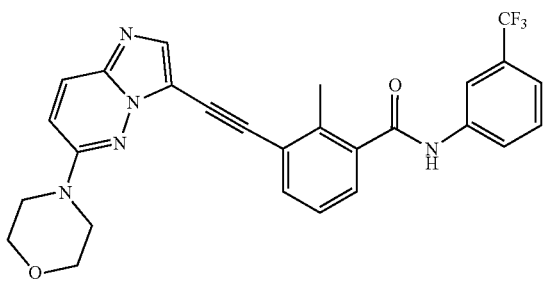 [SMILES: Cc1c(C#Cc2cnc3ccc(N4CCOCC4)nn23)cccc1C(=O)Nc1cccc(C(F)(F)F)c1]

138 mg (0.45 mmol) of Compound 3 and 300 mg (0.91 mmol) of Compound 5 were dissolved in 10 mL of anhydrous N,N-dimethylformamide (DMF), and then added with 7 mg (0.036 mmol) of cuprous iodide, 21 mg (0.023 mmol) of Benzylacetone dipalladium, 9 mg (0.045 mmol) of tri-tert-butylphosphorus and 124 mg (0.9 mmol) of potassium carbonate, and then react under Ar in a closed system. The mixture was heated and stirred at 80° C. and reacted overnight. The reaction solution was filtered through celite, and the solvent was spin-dried, and 120 mg of yellow-white solid was obtained by column chromatography (yield: 52%).

$^1$H NMR (400 MHz, Chloroform-d) δ 8.06-7.98 (m, 2H), 7.91 (d, J=8.1 Hz, 1H), 7.87-7.74 (m, 2H), 7.64 (d, J=7.7 Hz, 1H), 7.54 (t, J=8.0 Hz, 1H), 7.47 (d, J=6.5 Hz, 1H), 7.30 (d, J=7.6 Hz, 1H), 6.90 (d, J=9.5 Hz, 1H), 3.87 (t, J=4.7 Hz, 4H), 3.57 (t, J=4.8 Hz, 4H), 2.73 (s, 3H). LC-MS (ESI) m/z 504.2 [M−H]$^−$.

EXAMPLE 7: PREPARATION OF N-(3-CHLORO-5-(TRIFLUOROMETHYL)PHENYL)-2-METHYL-3-((6-MORPHOLINIMIDAZO[1,2-B]PYRIDAZINE-3-YL)ETHYNYL)BENZAMIDE (DESIGNATED AS XS3-61)

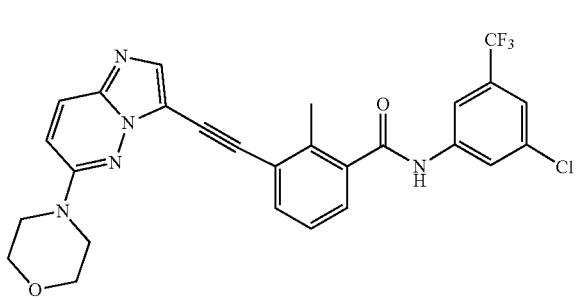 [SMILES: Cc1c(C#Cc2cnc3ccc(N4CCOCC4)nn23)cccc1C(=O)Nc1cc(Cl)cc(C(F)(F)F)c1]

The synthetic method is according to Example 6.

$^1$H NMR (400 MHz, DMSO-d$_6$) δ 10.92 (s, 1H), 8.13 (d, J=2.5 Hz, 2H), 7.98 (d, J=10.0 Hz, 2H), 7.70 (dd, J=7.7, 1.4 Hz, 1H), 7.61 (s, 1H), 7.56 (dd, J=7.7, 1.4 Hz, 1H), 7.42 (t, J=7.7 Hz, 1H), 7.32 (d, J=9.8 Hz, 1H), 3.74 (t, J=4.8 Hz, 4H), 3.53 (t, J=4.8 Hz, 4H), 2.63 (s, 3H). LC-MS (ESI) m/z 539.8 [M+H]$^+$.

EXAMPLE 8: PREPARATION OF N-(3-FLUORO-5-(TRIFLUOROMETHYL)PHENYL)-2-METHYL-3-((6-METHYLIMIDAZOPYRAZIN-3-YL-3-YL)BENZYL AMIDES (DESIGNATED AS XS4-80)

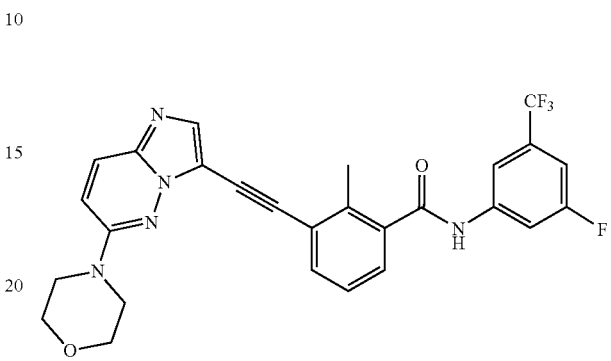

The synthetic method is according to Example 6.

$^1$H NMR (400 MHz, DMSO-d$_6$) δ 10.94 (s, 1H), 8.02-7.96 (m, 2H), 7.96-7.89 (m, 2H), 7.70 (dd, J=7.8, 1.4 Hz, 1H), 7.55 (dd, J=7.8, 1.4 Hz, 1H), 7.42 (dd, J=8.9, 6.3 Hz, 2H), 7.31 (d, J=10.0 Hz, 1H), 3.74 (t, J=4.8 Hz, 4H), 3.53 (t, J=4.8 Hz, 4H), 2.63 (s, 3H). HRMS (ESI) for C$_{27}$H$_{21}$F$_4$N$_5$O$_2$ [M+H]$^+$: calcd 524.1704, found 524.1686.

EXAMPLE 9: PREPARATION OF 2-METHYL-N-(3-METHYL-5-(TRIFLUOROMETHYL)PHENYL)-3-((6-METHYL-1,2-B]PYRIDAZIN-3-YL) BENZAMIDE (DESIGNATED AS XS4-81)

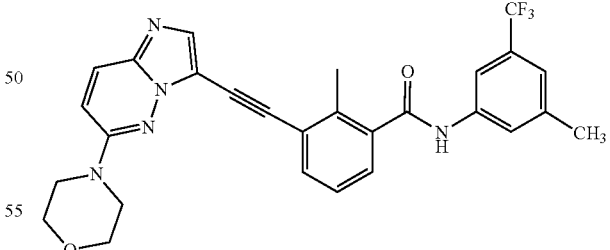

The synthetic method is according to Example 6.

$^1$H NMR (400 MHz, DMSO-d$_6$) δ 10.68 (s, 1H), 8.05-7.90 (m, 3H), 7.80 (s, 1H), 7.68 (dd, J=7.7, 1.4 Hz, 1H), 7.52 (dd, J=7.7, 1.4 Hz, 1H), 7.40 (t, J=7.7 Hz, 1H), 7.34-7.28 (m, 2H), 3.74 (dd, J=5.8, 3.9 Hz, 4H), 3.53 (t, J=4.8 Hz, 4H), 2.62 (s, 3H), 2.40 (s, 3H). HRMS (ESI) for C$_{28}$H$_{24}$F$_3$N$_5$O$_5$ [M+H]$^+$: calcd 520.1955, found 520.1939.

EXAMPLE 10: PREPARATION OF N-(3-METHOXY-5-(TRIFLUOROMETHYL)PHENYL)-2-METHYL-3-((6-METHYLIMIDAZOPYRAZIN-3-YL-3-YL) BENZAMIDE (DESIGNATED AS XS4-72)

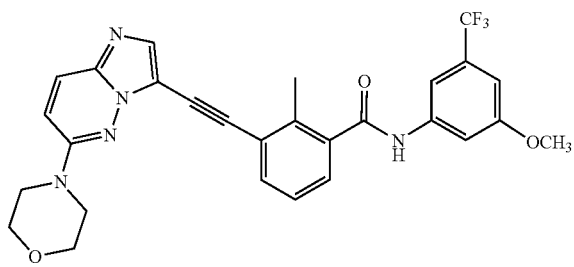 [SMILES: COc1cc(NC(=O)c2cccc(C#Cc3cnc4ccc(N5CCOCC5)nn34)c2C)cc(C(F)(F)F)c1]

The synthetic method is according to Example 6.

$^1$H NMR (400 MHz, DMSO-$d_6$) δ 10.72 (s, 1H), 7.97 (d, J=9.9 Hz, 1H), 7.93 (s, 1H), 7.81 (s, 1H), 7.68 (dd, J=7.8, 1.4 Hz, 1H), 7.62 (t, J=2.2 Hz, 1H), 7.53 (dd, J=7.8, 1.4 Hz, 1H), 7.41 (t, J=7.7 Hz, 1H), 7.31 (d, J=9.9 Hz, 1H), 7.01 (t, J=2.0 Hz, 1H), 3.84 (s, 3H), 3.74 (dd, J=5.8, 3.8 Hz, 4H), 3.53 (t, J=4.8 Hz, 4H), 2.62 (s, 3H). HRMS (ESI) for $C_{27}H_{21}ClF_3N_5O_2$ [M+H]$^+$: calcd 536.1904, found 536.1919.

EXAMPLE 11: PREPARATION OF N-(3,5-BIS(TRIFLUOROMETHYL)PHENYL)-2-METHYL-3-((6-METHYLIMIDAZOPYRAZIN-3-YL-3-YL) BENZAMIDE (DESIGNATED AS XS4-76)

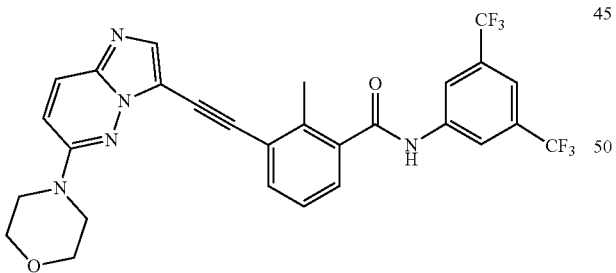

The synthetic method is according to Example 6.

$^1$H NMR (400 MHz, DMSO-$d_6$) δ 11.07 (s, 1H), 8.44 (s, 2H), 7.98 (d, J=10.0 Hz, 2H), 7.85 (s, 1H), 7.71 (dd, J=7.8, 1.4 Hz, 1H), 7.59 (dd, J=7.8, 1.4 Hz, 1H), 7.43 (t, J=7.7 Hz, 1H), 7.32 (d, J=9.5 Hz, 1H), 3.74 (t, J=4.8 Hz, 4H), 3.53 (t, J=4.8 Hz, 4H), 2.64 (s, 3H). HRMS (ESI) for $C_{28}H_{21}F_6N_5O_2$ [M+H]$^+$: calcd 574.1672, found 574.1676.

EXAMPLE 12: PREPARATION OF 2-METHYL-3-((6-METHYLIMIDAZOPYRAZIN-3-YL)ETHYNYL)-N-(3-NITRO-5-(TRIFLUOROMETHYL)PHENYL)BENZYL AMIDE (DESIGNATED AS XS4-77)

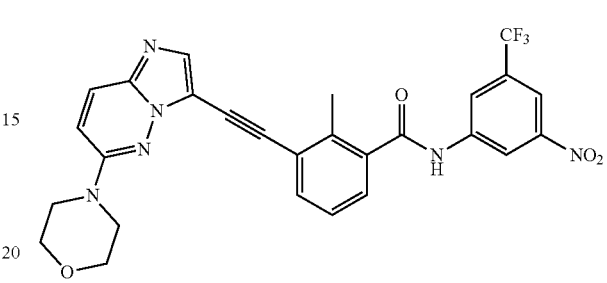

The synthetic method is according to Example 6.

$^1$H NMR (400 MHz, DMSO-$d_6$) δ 11.20 (s, 1H), 8.95 (t, J=2.1 Hz, 1H), 8.53 (s, 1H), 8.23 (d, J=2.1 Hz, 1H), 7.97 (d, J=9.9 Hz, 1H), 7.93 (s, 1H), 7.72 (dd, J=7.8, 1.4 Hz, 1H), 7.60 (dd, J=7.7, 1.4 Hz, 1H), 7.44 (t, J=7.7 Hz, 1H), 7.31 (dd, J=10.1, 1.6 Hz, 1H), 3.74 (t, J=4.8 Hz, 4H), 3.53 (t, J=4.9 Hz, 4H), 2.65 (s, 3H). HRMS (ESI) for $C_{27}H_{21}F_3N_6O_4$ [M+H]$^+$: calcd 551.1649, found 551.1667.

EXAMPLE 13: PREPARATION OF 2-METHYL-N-(3-((4-METHYLPIPERAZIN-1-YL)METHYL)-5-(TRIFLUOROMETHYL)PHENYL)-3-((6-METHYLENE) LINOIMIDAZO[1,2-B]PYRIDAZIN-3-YL)ETHYNYL)BENZAMIDE (DESIGNATED AS XS3-68)

The synthetic method is according to Example 6.

$^1$H NMR (400 MHz, Chloroform-d) δ 8.22 (s, 1H), 7.98 (s, 1H), 7.82 (s, 1H), 7.77 (s, 1H), 7.70 (d, J=9.8 Hz, 1H), 7.62 (dd, J=7.7, 1.4 Hz, 1H), 7.45-7.40 (m, 2H), 7.26 (d, J=7.7 Hz, 1H), 6.86 (d, J=9.9 Hz, 1H), 3.88-3.84 (m, 4H), 3.59 (s, 2H), 3.57-3.53 (m, 4H), 2.71 (s, 3H), 2.52 (s, 8H), 2.32 (s, 3H). LC-MS (ESI) m/z 618.3 [M+H]$^+$.

EXAMPLE 14: PREPARATION OF (S)-3-((6-(3-HYDROXYPYRROLIDIN-1-YL)IMIDAZO[1,2-B]PYRIDAZIN-3-YL)ETHYNYL)-2-METHYL-N-(3-(TRIFLUOROMETHYL)PHENYL)BENZAMIDE (DESIGNATED AS XS3-35)

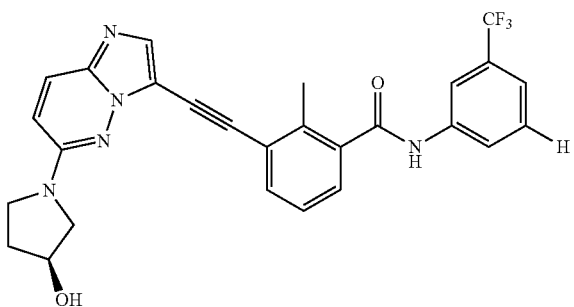 [SMILES: Cc1c(C#Cc2cnc3ccc(N4CC[C@H](O)C4)nn23)cccc1C(=O)Nc1cccc(C(F)(F)F)c1]

The synthetic method is according to Example 6.

¹H NMR (400 MHz, Chloroform-d) δ 8.16 (s, 1H), 8.05 (s, 1H), 7.91 (d, J=8.1 Hz, 1H), 7.74 (s, 1H), 7.65-7.57 (m, 2H), 7.54 (t, J=7.9 Hz, 1H), 7.46 (d, J=7.8 Hz, 1H), 7.41 (d, J=7.9 Hz, 1H), 7.24 (t, J=7.6 Hz, 1H), 6.58 (d, J=8.8 Hz, 1H), 5.03 (d, J=3.7 Hz, 1H), 4.42 (s, 1H), 3.62-3.50 (m, 3H), 3.40 (d, J=11.3 Hz, 1H), 2.67 (s, 3H), 2.10-1.98 (m, 1H), 1.92 (d, J=12.9 Hz, 1H).

LC-MS (ESI) m/z 504.2 [M−H]⁻.

EXAMPLE 15: PREPARATION OF (S)—N-(3-CHLORO-5-(TRIFLUOROMETHYL)PHENYL)-3-((6-(3-HYDROXYPYRROLIDIN-1-YL)IMIDAZO[1,2-B]PYRIDAZIN-3-YL)ETHYNYL)-2-METHYLBENZAMIDE (DESIGNATED AS XS3-58)

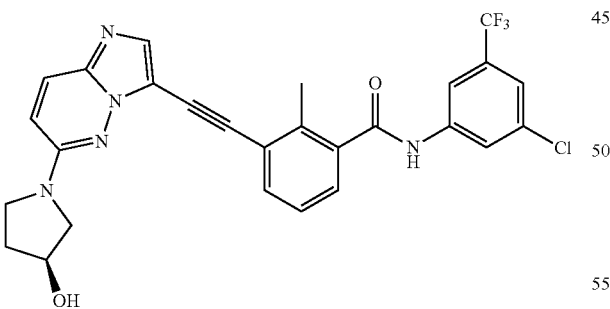

The synthetic method is according to Example 6.

¹H NMR (400 MHz, Chloroform-d) δ 8.27 (s, 1H), 8.08 (s, 1H), 7.86 (s, 1H), 7.72 (s, 1H), 7.64-7.59 (m, 2H), 7.44 (d, J=1.8 Hz, 1H), 7.39 (dd, J=7.7, 1.4 Hz, 1H), 7.25 (t, J=7.7 Hz, 1H), 6.60 (d, J=9.6 Hz, 1H), 4.66 (s, 1H), 3.70-3.54 (m, 5H), 2.71 (s, 3H), 2.16 (dd, J=7.9, 3.9 Hz, 2H). LC-MS (ESI) m/z 540.0 [M+H]⁺.

EXAMPLE 16: PREPARATION OF (S)-3-((6-(3-HYDROXYPYRROLIDIN-1-YL)IMIDAZO[1,2-B]PYRIDAZIN-3-YL)ETHYNYL)-2-METHYL-N-(3-((4-METHYLPIPERAZIN-1-YL)METHYL)-5-(TRIFLUOROMETHYL)PHENYL)BENZAMIDE (DESIGNATED AS XS3-36)

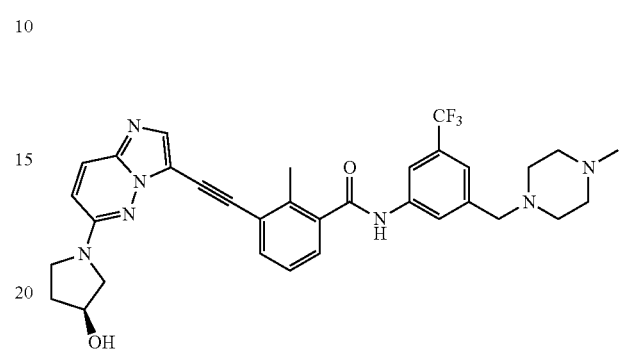

The synthetic method is according to Example 6.

¹H NMR (400 MHz, Chloroform-d) δ 8.18 (s, 1H), 8.02 (s, 1H), 7.79 (s, 1H), 7.72 (s, 1H), 7.63-7.58 (m, 2H), 7.41 (d, J=5.1 Hz, 2H), 7.25 (t, J=7.7 Hz, 1H), 6.58 (d, J=9.7 Hz, 1H), 4.64 (dd, J=4.3, 2.2 Hz, 1H), 3.68-3.56 (m, 7H), 2.74 (s, 3H), 2.51 (s, 8H), 2.31 (s, 3H), 2.17-2.09 (m, 2H).
LC-MS (ESI) m/z 618.3 [M+H]⁺.

EXAMPLE 17: PREPARATION OF 3-((6-(4-(DI-METHYLAMINO)PIPERIDIN-1-YL)IMIDAZO[1,2-B]PYRIDAZIN-3-YL)ETHYNYL)-2-METHYL-N-(3-(TRIFLUOROMETHYL)PHENYL)BENZAMIDE (DESIGNATED AS XS3-57)

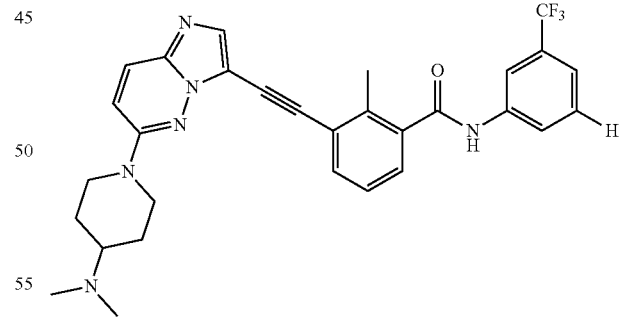

The synthetic method is according to Example 6.

¹H NMR (400 MHz, DMSO-d₆) δ 10.78 (s, 1H), 8.27 (d, J=2.3 Hz, 1H), 7.95 (d, J=2.6 Hz, 1H), 7.93 (d, J=3.2 Hz, 1H), 7.90 (s, 1H), 7.68 (dd, J=7.7, 1.4 Hz, 1H), 7.61 (t, J=8.1 Hz, 1H), 7.55 (dd, J=7.7, 1.4 Hz, 1H), 7.48 (d, J=7.8 Hz, 1H), 7.42 (t, J=7.7 Hz, 1H), 7.34 (d, J=10.0 Hz, 1H), 4.30 (d, J=13.4 Hz, 2H), 2.97 (t, J=12.0 Hz, 2H), 2.65 (s, 3H), 2.34 (s, 6H), 1.90 (d, J=12.1 Hz, 2H), 1.57-1.41 (m, 3H).
LC-MS (ESI) m/z 547.2 [M+H]⁺.

EXAMPLE 18: PREPARATION OF N-(3-CHLORO-5-(TRIFLUOROMETHYL)PHENYL)-3-((6-(4-(DIMETHYLAMINO)PIPERIDIN-1-YL)IMIDAZO[1,2-B]PYRIDAZIN-3-YL)ETHYNYL)-2-METHYLBENZAMIDE (DESIGNATED AS XS3-56)

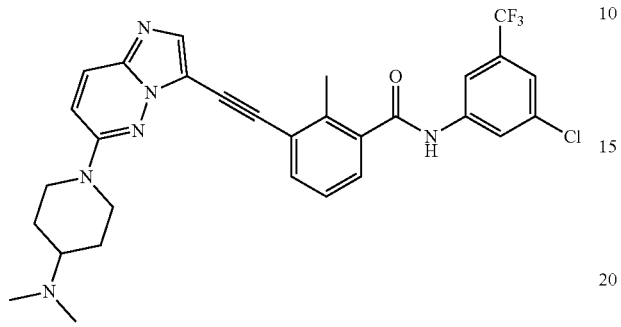

The synthetic method is according to Example 6.

¹H NMR (400 MHz, Chloroform-d) δ 8.30 (s, 1H), 8.09 (d, J=2.3 Hz, 1H), 7.86 (s, 1H), 7.74 (s, 1H), 7.66-7.60 (m, 2H), 7.44 (s, 1H), 7.40 (dd, J=7.7, 1.4 Hz, 1H), 7.28-7.23 (m, 1H), 6.90 (d, J=9.9 Hz, 1H), 4.26 (d, J=12.9 Hz, 2H), 2.98 (t, J=12.8 Hz, 2H), 2.72 (s, 3H), 2.41 (t, J=11.2 Hz, 1H), 2.33 (s, 6H), 2.01-1.93 (m, 2H), 1.66-1.54 (m, 2H). LC-MS (ESI) m/z 579.3 [M−H]⁻.

EXAMPLE 19: PREPARATION OF 3-((6-(4-(DIMETHYLAMINO)PIPERIDIN-1-YL)IMIDAZO[1,2-B]PYRIDAZIN-3-YL)ETHYNYL)-2-METHYL-N-(3-((4-METHYLPIPERAZIN-1-YL)METHYL)-5-(TRIFLUOROMETHYL)PHENYL)BENZAMIDE (DESIGNATED AS XS3-67)

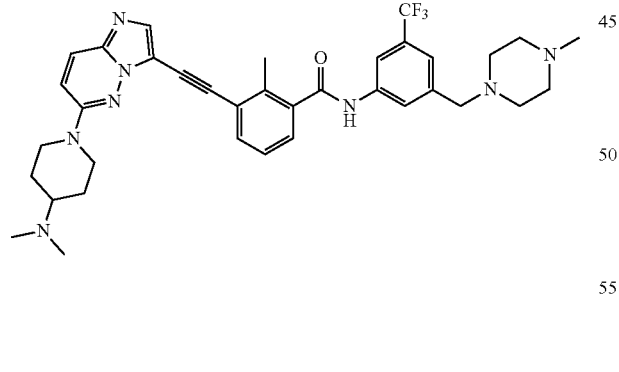

The synthetic method is according to Example 6.

¹H NMR (400 MHz, DMSO-d₆) δ 10.75 (s, 1H), 8.15 (s, 1H), 7.92 (d, J=9.8 Hz, 2H), 7.89 (s, 1H), 7.67 (d, J=6.4 Hz, 1H), 7.54 (d, J=6.9 Hz, 1H), 7.40 (t, J=7.7 Hz, 1H), 7.37 (s, 1H), 7.32 (d, J=10.0 Hz, 1H), 4.26 (d, J=13.0 Hz, 2H), 3.54 (s, 2H), 2.96 (t, J=12.1 Hz, 2H), 2.64 (s, 3H), 2.45-2.29 (m, 8H), 2.18 (s, 6H), 2.16 (s, 3H), 2.00 (q, J=7.5 Hz, 1H), 1.83 (d, J=11.5 Hz, 2H), 1.44 (q, J=10.5, 9.3 Hz, 2H). LC-MS (ESI) m/z 658.3 [M+H]⁺.

EXAMPLE 20: PREPARATION OF N-(3-CHLORO-5-(TRIFLUOROMETHYL)PHENYL)-2-METHYL-3-((6-(4-METHYLPIPERAZIN-1-YL)IMIDAZO[1,2-B]PYRIDAZIN-3-YL)ETHYNYL)BENZAMIDE (DESIGNATED AS XS3-51)

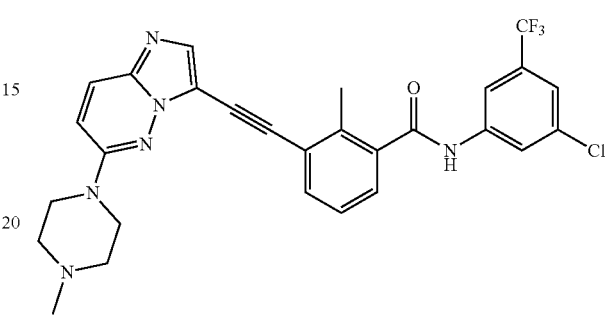

The synthetic method is according to Example 6.

¹H NMR (400 MHz, Chloroform-d) δ 8.08 (s, 2H), 7.86 (s, 1H), 7.83 (d, J=3.4 Hz, 1H), 7.78-7.72 (m, 1H), 7.66 (d, J=7.6 Hz, 1H), 7.46 (d, J=7.7 Hz, 1H), 7.43 (s, 1H), 7.32 (d, J=7.7 Hz, 1H), 6.89 (d, J=9.9 Hz, 1H), 3.80 (s, 4H), 3.13 (s, 3H), 2.74 (s, 3H), 2.53 (d, J=21.6 Hz, 4H). LC-MS (ESI) m/z 553.2 [M+H]⁺.

EXAMPLE 21: PREPARATION OF (R)—N-(3-CHLORO-5-(TRIFLUOROMETHYL)PHENYL)-3-((6-(3,4-DIMETHYLPIPERAZIN-1-YL)IMIDAZO[1,2-B]PYRIDAZIN-3-YL)ETHYNYL)-2-METHYLBENZAMIDE (DESIGNATED AS XS3-52)

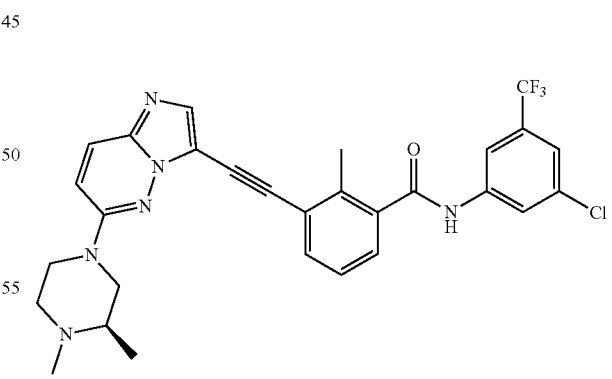

The synthetic method is according to Example 6.

¹H NMR (400 MHz, DMSO-d₆) δ 10.93 (s, 1H), 8.13 (s, 2H), 8.06 (s, 1H), 7.97 (s, 1H), 7.71 (d, J=7.2 Hz, 1H), 7.62 (s, 1H), 7.58 (d, J=7.3 Hz, 1H), 7.44 (t, J=7.6 Hz, 1H), 7.39 (d, J=9.5 Hz, 1H), 3.13-3.06 (m, 4H), 2.91 (s, 2H), 2.75 (m, 1H), 2.65 (s, 3H), 2.46 (s, 3H), 1.24 (s, 3H). LC-MS (ESI) m/z 567.2 [M+H]⁺.

EXAMPLE 22: PREPARATION OF N-(3-CHLORO-5-(TRIFLUOROMETHYL)PHENYL)-3-((6-(4-HYDROXYPIPERIDIN-1-YL)IMIDAZO[1,2-B]PYRIDAZINE-3-YL)ETHYNYL)-2-METHYLBENZAMIDE (DESIGNATED AS XS3-55)

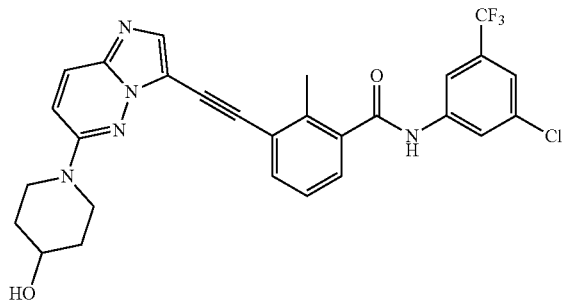 [SMILES: Cc1c(C#Cc2cnc3ccc(N4CCC(O)CC4)nn23)cccc1C(=O)Nc1cc(Cl)cc(C(F)(F)F)c1]

The synthetic method is according to Example 6.

$^1$H NMR (400 MHz, DMSO-d$_6$) δ 10.93 (s, 1H), 8.14 (d, J=1.8 Hz, 2H), 7.94-7.88 (m, 2H), 7.69 (dd, J=7.7, 1.4 Hz, 1H), 7.61 (s, 1H), 7.56 (dd, J=7.7, 1.4 Hz, 1H), 7.42 (t, J=7.7 Hz, 1H), 7.32 (d, J=10.0 Hz, 1H), 4.71 (d, J=4.2 Hz, 1H), 4.00-3.93 (m, 2H), 3.74 (m, 1H), 3.25 (t, J=13.1 Hz, 2H), 2.64 (s, 3H), 1.82 (d, J=12.8 Hz, 2H), 1.49-1.40 (m, 2H). LC-MS (ESI) m/z 552.1 [M−H]$^-$.

EXAMPLE 23: PREPARATION OF 3-((6-(4-ACETYLPIPERAZIN-1-YL)IMIDAZO[1,2-B]PYRIDAZIN-3-YL)ETHYNYL)-N-(3-CHLORO-5-(TRIFLUORO) METHYL)PHENYL)-2-METHYLBENZAMIDE (DESIGNATED AS XS3-54)

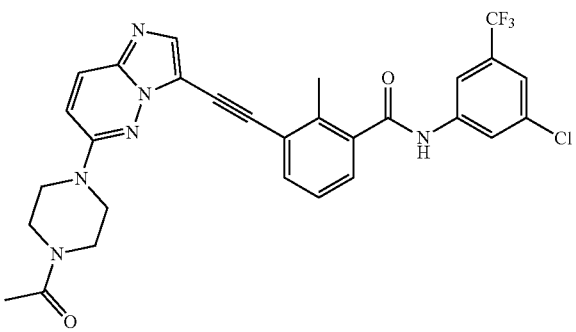 [SMILES: CC(=O)N1CCN(c2ccc3ncc(C#Cc4cccc(C(=O)Nc5cc(Cl)cc(C(F)(F)F)c5)c4C)n3n2)CC1]

The synthetic method is according to Example 6.

$^1$H NMR (400 MHz, DMSO-d$_6$) δ 10.93 (s, 1H), 8.14 (d, J=1.7 Hz, 2H), 7.98 (d, J=9.9 Hz, 1H), 7.93 (s, 1H), 7.71 (dd, J=7.7, 1.3 Hz, 1H), 7.61 (d, J=2.0 Hz, 1H), 7.57 (dd, J=7.7, 1.4 Hz, 1H), 7.43 (t, J=7.7 Hz, 1H), 7.34 (d, J=10.0 Hz, 1H), 3.66-3.53 (m, 8H), 2.65 (s, 3H), 2.04 (s, 3H). LC-MS (ESI) m/z 581.5 [M+H]$^+$.

EXAMPLE 24: PREPARATION OF N-(3-CHLORO-5-(TRIFLUOROMETHYL)PHENYL)-2-METHYL-3-((6-((2-MORPHOLINOETHYL)AMINO)IMIDAZO[1,2-B]PYRIDAZIN-3-YL)ETHYNYL)BENZAMIDE (DESIGNATED AS XS3-53)

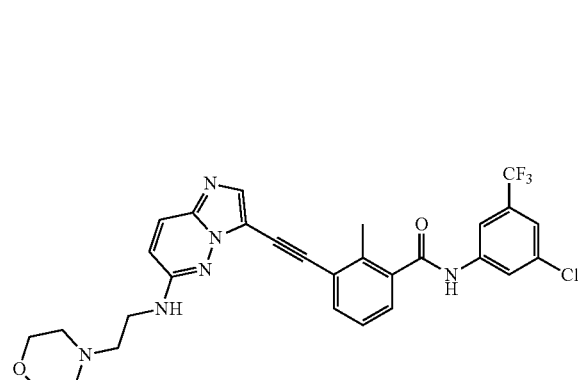

The synthetic method is according to Example 6.

$^1$H NMR (400 MHz, Chloroform-d) δ 8.28 (s, 1H), 8.08 (s, 1H), 7.87 (s, 1H), 7.66 (d, J=7.7 Hz, 2H), 7.47 (d, J=7.5 Hz, 1H), 7.44 (s, 1H), 7.34 (d, J=7.9 Hz, 1H), 7.31 (s, 1H), 6.73 (s, 2H), 4.01 (s, 4H), 3.78 (s, 2H), 3.19 (s, 2H), 3.05 (s, 4H), 2.71 (s, 3H). LC-MS (ESI) m/z 583.2 [M+H]$^+$.

EXAMPLE 25: PREPARATION OF 3-((6-(4-HYDROXYPIPERIDIN-1-YL)IMIDAZO[1,2-B]PYRIDAZIN-3-YL)ETHYNYL)-2-METHYL-N-(3-(((4-METHYLPIPERAZIN-1-YL)METHYL)-5-(TRIFLUOROMETHYL)PHENYL)BENZAMIDE (DESIGNATED AS XS3-81)

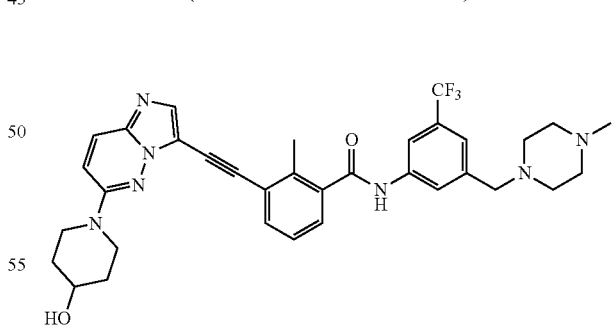

The synthetic method is according to Example 6.

$^1$H NMR (400 MHz, Chloroform-d) δ 8.36 (s, 1H), 8.01 (s, 1H), 7.80 (s, 1H), 7.73 (s, 1H), 7.62 (d, J=9.9 Hz, 1H), 7.59 (dd, J=7.8, 1.4 Hz, 1H), 7.43-7.38 (m, 2H), 7.24 (t, J=7.7 Hz, 1H), 6.88 (d, J=9.9 Hz, 1H), 4.0-3.91 (m, 3H), 3.59 (s, 2H), 3.28 (t, J=13.1 Hz, 2H), 2.70 (s, 3H), 2.51 (s, 8H), 2.31 (s, 3H), 1.99-1.95 (m, 2H), 1.69-1.61 (m, 2H). LC-MS (ESI) m/z 632.3 [M+H]$^+$.

EXAMPLE 26: PREPARATION OF N-(3-CHLORO-5-(TRIFLUOROMETHYL)PHENYL)-2-METHYL-3-((6-(4-MORPHOLINPIPERIDIN-1-YL)IMIDAZO[1,2-B]PYRIDAZIN-3-YL)ETHYNYL)BENZAMIDE (DESIGNATED AS XS3-130)

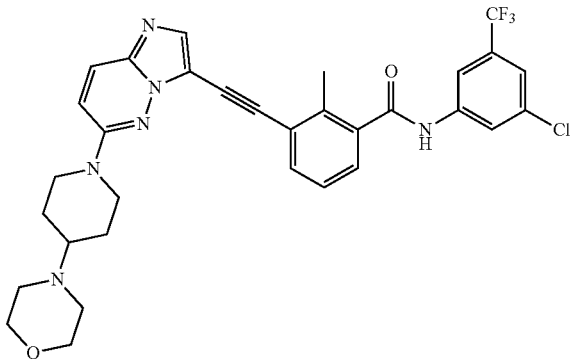 [SMILES: Cc1c(C#Cc2cnc3ccc(N4CCC(N5CCOCC5)CC4)nn23)cccc1C(=O)Nc1cc(Cl)cc(C(F)(F)F)c1]

The synthetic method is according to Example 6.

$^1$H NMR (400 MHz, DMSO-d$_6$) δ 10.93 (s, 1H), 8.13 (s, 2H), 7.92 (d, J=9.8 Hz, 2H), 7.69 (d, J=7.3 Hz, 1H), 7.61 (s, 1H), 7.56 (d, J=7.4 Hz, 1H), 7.42 (t, J=7.7 Hz, 1H), 7.33 (d, J=9.8 Hz, 1H), 4.26 (d, J=13.0 Hz, 2H), 3.54 (s, 4H), 2.97 (t, J=12.3 Hz, 2H), 2.64 (s, 3H), 2.45 (s, 5H), 1.86 (d, J=12.8 Hz, 2H), 1.45 (d, J=12.2 Hz, 2H). HRMS (ESI) for C$_{32}$H$_{30}$ClF$_3$N$_6$O$_2$ [M+H]$^+$: calcd 623.2144, found 623.2126.

EXAMPLE 27: PREPARATION OF N-(3-CHLORO-5-(TRIFLUOROMETHYL)PHENYL)-2-METHYL-3-((6-(4-(OXETAN-3-YL)PIPERAZINE)-1-YL)IMIDAZO[1,2-B]PYRIDAZIN-3-YL)ETHYNYL)BENZAMIDE (DESIGNATED AS XS3-138)

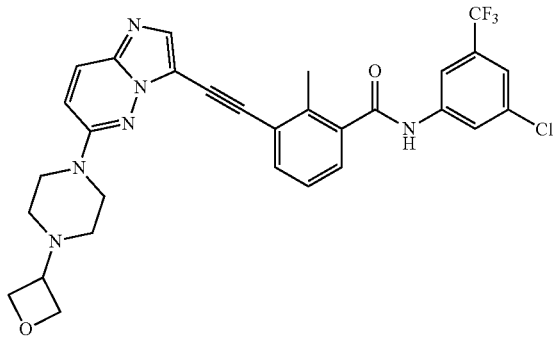 [SMILES: Cc1c(C#Cc2cnc3ccc(N4CCN(C5COC5)CC4)nn23)cccc1C(=O)Nc1cc(Cl)cc(C(F)(F)F)c1]

The synthetic method is according to Example 6.

$^1$H NMR (400 MHz, DMSO-d$_6$) δ 10.92 (s, 1H), 8.13 (s, 2H), 7.98-7.87 (m, 2H), 7.69 (d, J=8.2 Hz, 1H), 7.61 (s, 1H), 7.56 (d, J=6.9 Hz, 1H), 7.42 (t, J=7.7 Hz, 1H), 7.34 (d, J=9.9 Hz, 1H), 4.55 (t, J=6.5 Hz, 2H), 4.47 (t, J=6.1 Hz, 2H), 3.60 (t, J=5.1 Hz, 4H), 3.45 (m, 1H), 2.63 (s, 3H), 2.40 (t, J=5.0 Hz, 4H). HRMS (ESI) for C$_{30}$H$_{26}$ClF$_3$N$_6$O$_2$ [M+H]$^+$: calcd 595.1831, found 595.1811.

EXAMPLE 28: PREPARATION OF N-(3-CHLORO-5-(TRIFLUOROMETHYL)PHENYL)-3-((6-((2-(DIMETHYLAMINO)ETHYL)(METHYL)AMINO)IMIDAZO[1,2-B]PYRIDAZIN-3-YL)ETHYNYL)-2-METHYLBENZAMIDE (DESIGNATED AS XS3-134)

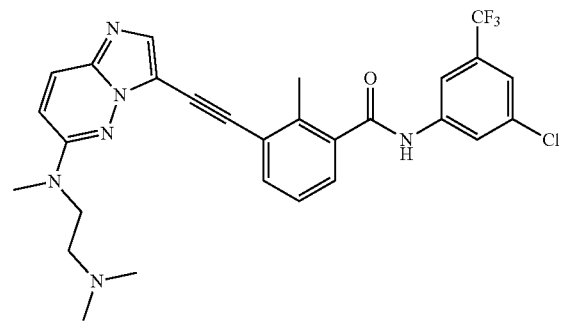 [SMILES: Cc1c(C#Cc2cnc3ccc(N(C)CCN(C)C)nn23)cccc1C(=O)Nc1cc(Cl)cc(C(F)(F)F)c1]

The synthetic method is according to Example 6.

$^1$H NMR (400 MHz, DMSO-d$_6$) δ 10.92 (s, 1H), 8.13 (d, J=1.8 Hz, 2H), 7.90-7.82 (m, 2H), 7.68 (dd, J=7.7, 1.4 Hz, 1H), 7.60 (d, J=1.8 Hz, 1H), 7.55 (dd, J=7.8, 1.3 Hz, 1H), 7.41 (t, J=7.7 Hz, 1H), 7.14 (d, J=10.0 Hz, 1H), 3.64 (t, J=6.7 Hz, 2H), 3.09 (s, 3H), 2.63 (s, 3H), 2.45 (t, J=6.7 Hz, 2H), 2.16 (s, 6H). HRMS (ESI) for C$_{28}$H$_{26}$ClF$_3$N$_6$O [M+H]$^+$: calcd 555.1881, found 555.1862.

EXAMPLE 29: PREPARATION OF N-(3-CHLORO-5-(TRIFLUOROMETHYL)PHENYL)-3-((6-((2-METHOXYETHYL)AMINO)IMIDAZO[1,2-B] PYRIDAZIN-3-YL)ETHYNYL)-2-METHYLBENZAMIDE (DESIGNATED AS XS3-135)

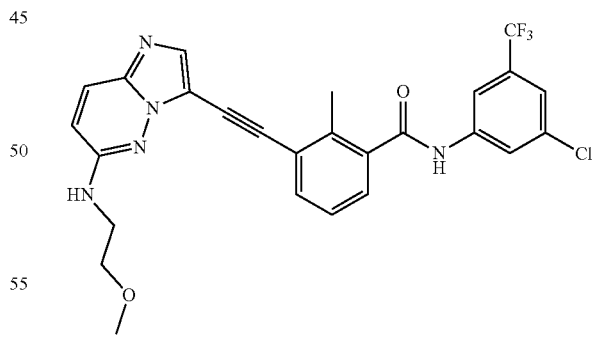

The synthetic method is according to Example 6.

$^1$H NMR (600 MHz, DMSO-d$_6$) δ 10.93 (s, 1H), 8.14-8.09 (m, 2H), 7.81-7.73 (m, 2H), 7.67 (dd, J=7.7, 1.3 Hz, 1H), 7.59 (d, J=1.9 Hz, 1H), 7.54 (dd, J=7.7, 1.3 Hz, 1H), 7.41 (t, J=7.7 Hz, 1H), 7.27 (t, J=5.5 Hz, 1H), 6.82 (d, J=9.6 Hz, 1H), 3.54 (t, J=5.5 Hz, 2H), 3.47-3.45 (m, 2H), 3.26 (s, 3H), 2.63 (s, 3H). HRMS (ESI) for C$_{26}$H$_{21}$ClF$_3$N$_5$O$_2$ [M+H]$^+$: calcd 528.1409, found 528.1394.

EXAMPLE 30: PREPARATION OF N-(3-CHLORO-5-(TRIFLUOROMETHYL)PHENYL)-3-((6-((4-HYDROXYBUTYL)AMINO)IMIDAZO[1,2-B]PYRIDAZINE-3-YL)ETHYNYL)-2-METHYLBENZAMIDE (DESIGNATED AS XS3-139)

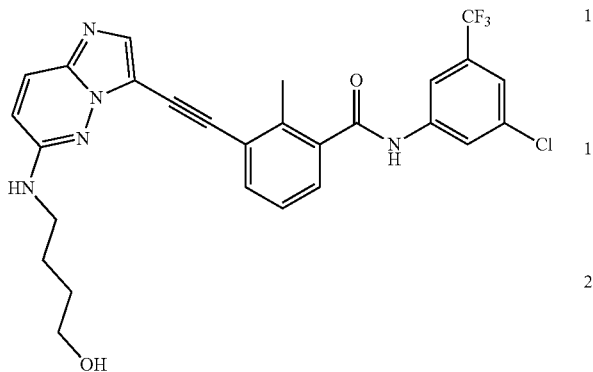

The synthetic method is according to Example 6.

$^1$H NMR (400 MHz, DMSO-$d_6$) δ 10.92 (s, 1H), 8.12 (s, 2H), 7.76 (d, J=9.6 Hz, 2H), 7.68 (dd, J=7.7, 1.4 Hz, 1H), 7.61 (s, 1H), 7.55 (dd, J=7.7, 1.4 Hz, 1H), 7.41 (t, J=7.7 Hz, 1H), 7.16 (t, J=5.3 Hz, 1H), 6.77 (d, J=8.9 Hz, 1H), 4.38 (t, J=5.1 Hz, 1H), 3.43-3.37 (m, 2H), 3.30-3.25 (m, 2H), 2.65 (s, 3H), 1.70-1.59 (m, 2H), 1.53-1.46 (m, 2H). HRMS (ESI) for $C_{27}H_{23}ClF_3N_5O_2$ [M+H]$^+$: calcd 542.1565, found 542.1552.

EXAMPLE 31: PREPARATION OF 3-((6-(4-AMINOPIPERIDIN-1-YL)IMIDAZO[1,2-B]PYRIDAZIN-3-YL)ETHYNYL)-N-(3-CHLORO-5-(TRIFLUOROMETHYL)PHENYL)-2-METHYLBENZAMIDE (DESIGNATED AS XS3-131)

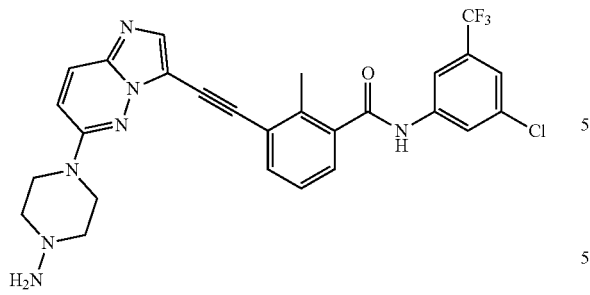

The synthetic method is according to Example 6.

$^1$H NMR (400 MHz, DMSO-$d_6$) δ 10.96 (s, 1H), 8.15 (s, 2H), 7.96 (d, J=9.9 Hz, 1H), 7.92 (s, 1H), 7.70 (dd, J=7.8, 1.3 Hz, 1H), 7.61 (d, J=2.3 Hz, 1H), 7.57 (dd, J=7.7, 1.3 Hz, 1H), 7.43 (t, J=7.7 Hz, 1H), 7.34 (d, J=10.0 Hz, 1H), 4.23 (d, J=13.4 Hz, 2H), 3.17 (s, 2H), 3.12-3.02 (m, 2H), 2.65 (s, 3H), 2.63 (m, 1H), 1.89 (d, J=11.2 Hz, 2H), 1.48 (q, J=11.7, 10.8 Hz, 2H). HRMS (ESI) for $C_{28}H_{24}ClF_3N_6O$ [M+H]$^+$: calcd 553.1725, found 553.1708.

EXAMPLE 32: PREPARATION OF (R)-3-((6-(3-AMINOPIPERIDIN-1-YL)IMIDAZO[1,2-B]PYRIDAZIN-3-YL)ETHYNYL)-N-(3-CHLORO-5-(TRIFLUOROMETHYL)PHENYL)-2-METHYLBENZAMIDE (DESIGNATED AS XS3-137)

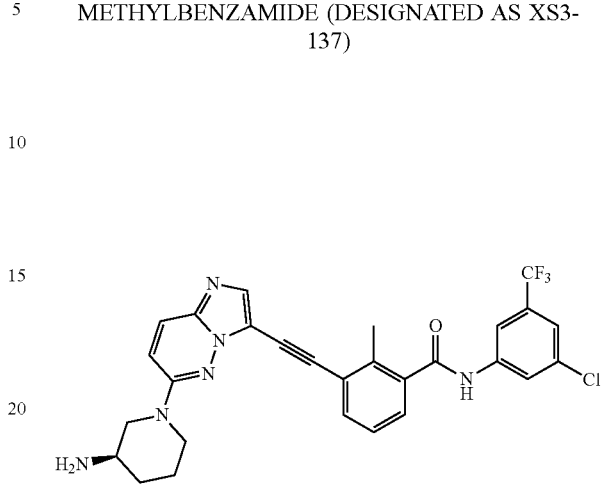

The synthetic method is according to Example 6.

$^1$H NMR (400 MHz, DMSO-$d_6$) δ 10.93 (s, 1H), 8.13 (s, 2H), 7.92-7.85 (m, 2H), 7.69 (d, J=7.6 Hz, 1H), 7.60 (s, 1H), 7.55 (d, J=7.6 Hz, 1H), 7.42 (t, J=7.7 Hz, 1H), 7.28 (d, J=10.0 Hz, 1H), 4.04 (dd, J=10.6, 6.5 Hz, 2H), 2.98 (m, 1H), 2.78-2.69 (m, 2H), 2.65 (s, 3H), 1.86 (m, 1H), 1.74 (m, 1H), 1.61-1.43 (m, 2H). HRMS (ESI) for $C_{28}H_{24}ClF_3N_6O$ [M+H]$^+$: calcd 553.1725, found 553.1706.

EXAMPLE 33: PREPARATION OF (S)-3-((6-(3-AMINOPIPERIDIN-1-YL)IMIDAZO[1,2-B]PYRIDAZIN-3-YL)ETHYNYL)-N-(3-CHLORO-5-(TRIFLUOROMETHYL)PHENYL)-2-METHYLBENZAMIDE (DESIGNATED AS XS3-136)

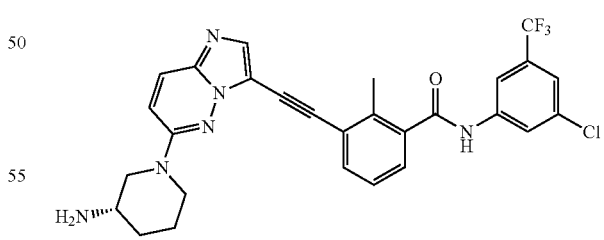

The synthetic method is according to Example 6.

$^1$H NMR (400 MHz, DMSO-$d_6$) δ 10.93 (s, 1H), 8.13 (s, 2H), 7.95-7.84 (m, 2H), 7.69 (d, J=7.6 Hz, 1H), 7.60 (s, 1H), 7.55 (d, J=7.6 Hz, 1H), 7.42 (t, J=7.7 Hz, 1H), 7.28 (d, J=10.0 Hz, 1H), 4.04 (dd, J=11.5, 5.9 Hz, 2H), 3.04-2.93 (m, 2H), 2.80-2.70 (m, 2H), 2.65 (s, 3H), 1.86 (d, J=12.0 Hz, 1H), 1.74 (m, 1H), 1.53 (q, J=11.8 Hz, 1H). HRMS (ESI) for $C_{28}H_{24}ClF_3N_6O$ [M+H]$^+$: calcd 553.1725, found 553.1703.

EXAMPLE 34: PREPARATION OF N-(3-CHLORO-5-(TRIFLUOROMETHYL)PHENYL)-3-(6-(4-HYDROXY-4-METHYLPIPERIDIN-1-YL)IMIDAZO[1,2-B]PYRIDAZIN-3-YL)ETHYNYL)-2-METHYLBENZAMIDE (DESIGNATED AS XS3-153)

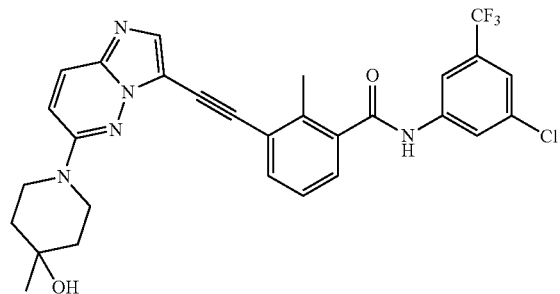 [SMILES: Cc1c(C#Cc2cnc3ccc(N4CCC(C)(O)CC4)nn23)cccc1C(=O)Nc1cc(Cl)cc(C(F)(F)F)c1]

The synthetic method is according to Example 6.

$^1$H NMR (400 MHz, DMSO-$d_6$) δ 10.93 (s, 1H), 8.13 (t, J=2.1 Hz, 2H), 7.90 (d, J=10.2 Hz, 2H), 7.69 (dd, J=7.7, 1.4 Hz, 1H), 7.61 (d, J=1.8 Hz, 1H), 7.56 (dd, J=7.7, 1.4 Hz, 1H), 7.42 (t, J=7.7 Hz, 1H), 7.32 (d, J=10.0 Hz, 1H), 4.39 (s, 1H), 3.92-3.83 (m, 2H), 3.44-3.37 (m, 2H), 2.64 (s, 3H), 1.55 (t, J=5.6 Hz, 4H), 1.15 (s, 3H). HRMS (ESI) for $C_{29}H_{25}ClF_3N_5O_2$ [M+H]$^+$: calcd 568.1722, found 568.1699.

EXAMPLE 35: PREPARATION OF 2-METHYL-N-(3-(4-METHYL-1H-IMIDAZOL-1-YL)-5-(TRIFLUOROMETHYL)PHENYL)-3-((6-MORPHOLINO-IMIDAZO[1,2-B]PYRIDO-3-YLETHYNYL)BENZAMIDE (DESIGNATED AS XS3-91)

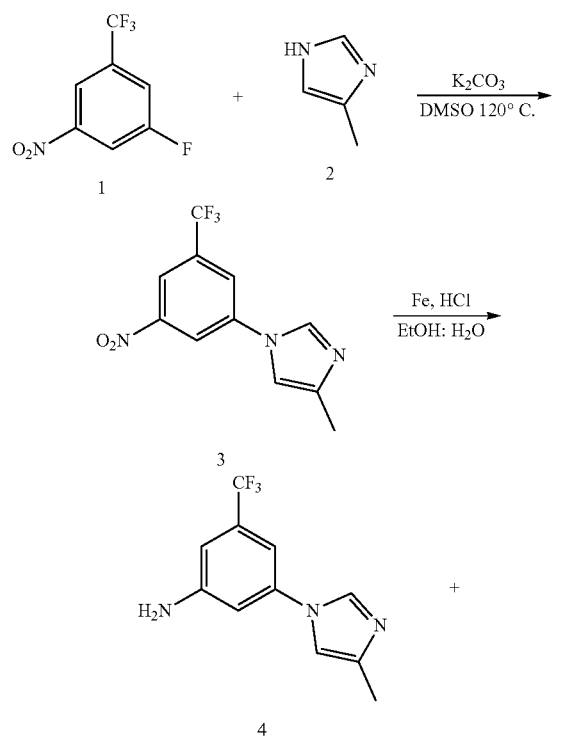

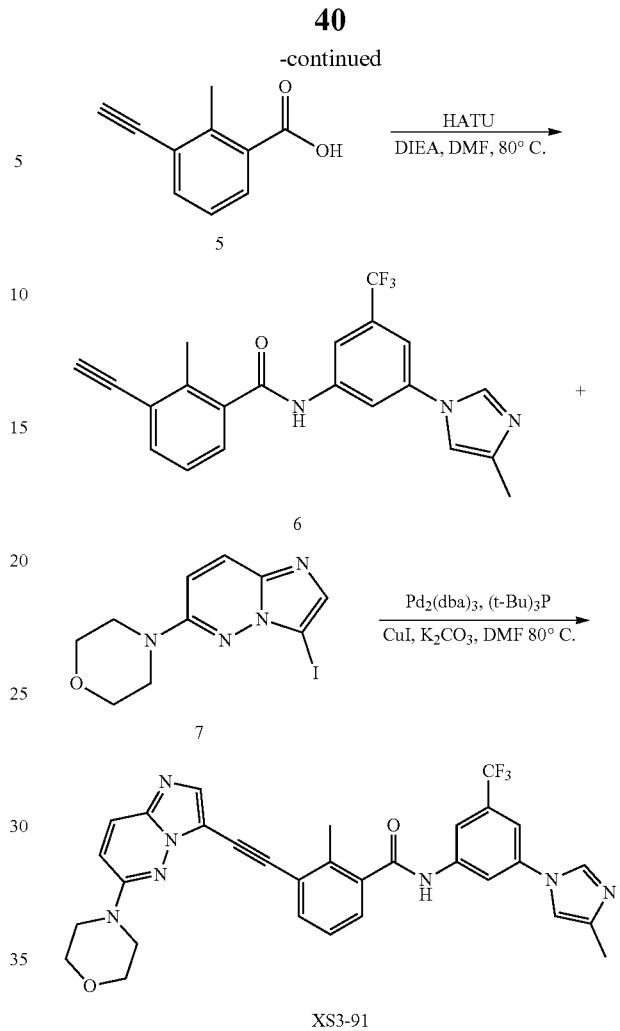

Step 1: Preparation of 4-Methyl-1-(3-nitro-5-(trifluoromethyl)phenyl)-1H-imidazole (Compound 3)

1 g (4.5 mmol) of Compound 1 and 800 mg (9.5 mmol) of Compound 2 were dissolved in 20 mL of dimethyl sulfoxide (DMSO), and then added with 850 mg (7 mmol) of potassium carbonate. The mixture was heated and stirred at 120° C., and reacted overnight. The reaction system was spin-dried, and 430 mg of yellow-white solid was obtained by column chromatography (yield: 36%).

$^1$H NMR (400 MHz, Chloroform-d) δ 8.46 (q, J=1.9 Hz, 2H), 8.02-7.97 (m, 2H), 7.17 (s, 1H), 2.36 (d, J=1.0 Hz, 3H). LC-MS (ESI) m/z 272.1 [M+H]$^+$.

Step 2: Preparation of 3-(4-Methyl-1H-imidazol-1-yl)-5-(trifluoromethyl)aniline (Compound 4)

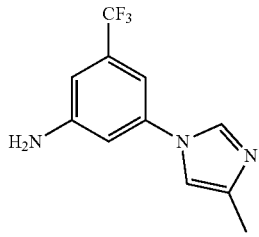 [SMILES: Cc1cn(-c2cc([N+](=O)[O-])cc(C(F)(F)F)c2)cn1]

430 mg (1.59 mmol) of Compound 3 was dissolved in a mixed solvent of ethanol: water with a volume ratio of 7:3, added with hydrochloric acid solution to make the reaction system weakly acidic, and then added with 444 mg (7.93 mmol) of iron powder. The mixture was heated and stirred at 70° C. for 2 hours. The reaction solution was filtered through celite, the reaction system was spin-dried, and the crude product was directly used in the next reaction.

Step 3: Preparation of 3-Ethynyl-2-methyl-N-(3-(4-methyl-1H-imidazol-1-yl)-5-(trifluoromethyl)phenyl)benzamide (Compound 6)

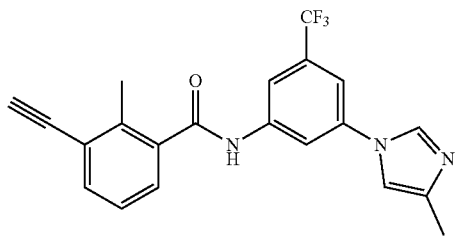 [SMILES: C#Cc1cccc(C(=O)Nc2cc(-n3cnc(C)c3)cc(C(F)(F)F)c2)c1C]

270 mg (1.12 mmol) of Compound 4 and 215 mg (1.3 mmol) of Compound 5 were dissolved in 15 mL of N,N-dimethylformamide (DMF), and then added with 638 mg (1.68 mmol) of 2-(7-azabenzone) Triazole)-N,N,N',N'-tetramethylurea hexafluorophosphate (HATU) and 216 mg (1.68 mmol) of N,N-diisopropylethylamine (DIPEA). The mixture was heated and stirred at 80° C. and reacted overnight. The reaction system was spin-dried, and added with water, and then extracted with ethyl acetate, rinsed with water, dried with anhydrous sodium sulfate. The solvent was spin-dried, and 220 mg of yellow oil was obtained by column chromatography (yield: 51%).

$^1$H NMR (400 MHz, Chloroform-d) δ 9.41 (s, 1H), 8.22 (s, 1H), 7.91 (s, 1H), 7.73 (s, 1H), 7.55 (d, J=7.6 Hz, 1H), 7.43 (d, J=7.2 Hz, 1H), 7.34 (s, 1H), 7.19 (t, J=7.7 Hz, 1H), 7.09 (s, 1H), 3.34 (s, 1H), 2.58 (s, 3H), 2.25 (s, 3H). LC-MS (ESI) m/z 384.1 [M+H]$^+$.

Step 4: Preparation of 2-Methyl-N-(3-(4-methyl-1H-imidazol-1-yl)-5-(trifluoromethyl) phenyl)-3-((6-morpholinimidazole) [1,2-b]pyrido-3-ylethynyl) benzamide (Designated as XS3-91)

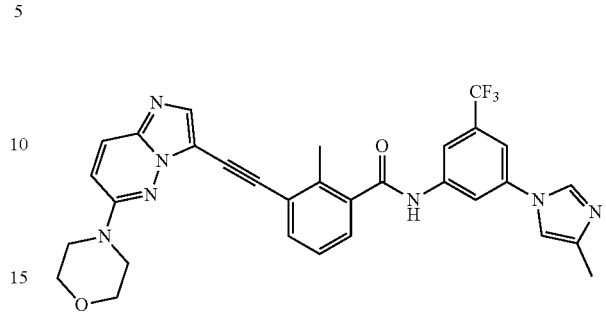

150 mg (0.39 mmol) of Compound 6 and 130 mg (0.47 mmol) of Compound 7 were dissolved in 10 mL of anhydrous N,N-dimethylformamide (DMF), and then added with 6 mg (0.03 mmol) of cuprous iodide, 17 mg (0.019 mmol) of tris(dibenzylideneacetone) dipalladium, 8 mg (0.039 mmol) of tri-tert-butylphosphorus, and 107 mg (0.78 mmol) of potassium carbonate, and then reacted under Ar in a closed system. The mixture was heated and stirred at 80° C. and reacted overnight. The reaction solution was filtered through celite, and the solvent was spin-dried, and 40 mg of yellow-white solid was obtained by column chromatography (yield: 18%).

$^1$H NMR (400 MHz, DMSO-d$_6$) δ 10.92 (s, 1H), 8.20 (d, J=1.6 Hz, 2H), 8.10 (s, 1H), 7.98 (d, J=9.9 Hz, 1H), 7.93 (s, 1H), 7.76 (s, 1H), 7.72-7.69 (m, 1H), 7.57 (d, J=7.4 Hz, 1H), 7.48 (s, 1H), 7.44 (d, J=7.7 Hz, 1H), 7.32 (d, J=10.0 Hz, 1H), 3.77-3.72 (m, 4H), 3.54 (t, J=4.9 Hz, 4H), 2.65 (s, 3H), 2.19 (d, J=1.0 Hz, 3H). LC-MS (ESI) m/z 586.6 [M+H]$^+$.

EXAMPLE 36: PREPARATION OF 3-((6-(4-HYDROXYPIPERIDIN-1-YL)IMIDAZO[1,2-B]PYRIDAZIN-3-YL)ETHYNYL)-2-METHYL-N-(3-(4-METHYL-1H-IMIDAZOL-1-YL)-5-(TRIFLUOROMETHYL)PHENYL)BENZAMIDE (DESIGNATED AS XS3-87)

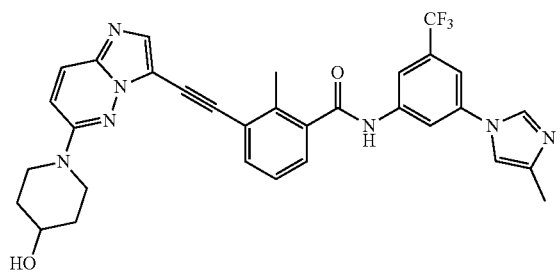 [SMILES: Cc1cn(-c2cc(NC(=O)c3cccc(C#Cc4cnc5ccc(N6CCC(O)CC6)nn45)c3C)cc(C(F)(F)F)c2)cn1]

The synthetic method is according to Example 35.

$^1$H NMR (400 MHz, Chloroform-d) δ 8.25 (s, 1H), 7.97 (s, 1H), 7.88 (s, 1H), 7.83 (s, 1H), 7.75-7.70 (m, 2H), 7.68 (d, J=7.7 Hz, 1H), 7.47 (d, J=7.5 Hz, 1H), 7.42 (s, 1H), 7.33 (t, J=7.7 Hz, 1H), 7.13 (s, 1H), 6.93 (d, J=9.9 Hz, 1H), 4.05-3.97 (m, 3H), 3.37-3.29 (m, 2H), 2.78 (s, 3H), 2.33 (d, J=1.0 Hz, 3H), 2.03 (d, J=9.6 Hz, 2H), 1.69 (d, J=9.5 Hz, 3H). LC-MS (ESI) m/z 600.0 [M+H]$^+$.

EXAMPLE 37: IC$_{50}$ DETERMINATION OF COMPOUNDS AGAINST TRKS KINASES

Kinase activity detection: Applying Z'-LYTE™ technology (detection by fluorescence, enzyme-coupled format, based on the difference in sensitivity of phosphorylated and non-phosphorylated peptides to proteolytic cleavage), based on the principle of fluorescence resonance energy transfer (FRET), using Z'-LYTE™ FRET peptide substrates, and the inhibitory activity of compounds on TRKs (TRK1, TRK2, TRK3) kinases (American Life Technologies, PV3144, PV3616, PV3617) was detected through secondary reaction.

Enzymatic reaction: In a 384-well plate, added 54 μL of enzyme-substrate system [50 mM of 4-hydroxyethylpiperazineethanesulfonic acid (HEPES) pH 7.5, 0.01% BRIJ-35, 10 mM of magnesium chloride (MgCl2), 1 mM of ethylene glycol bis(2-aminoethyl ether)tetraacetic acid (EGTA), 2 μM of Tyr 01 peptide substrate], and transferred 5 nL of compound (concentration gradient) using an Echo520 ultra-micro liquid pipetting system. After shaking at room temperature for 10-20 minutes, transferred 200 nL, 12.5 nL, 25 nL ATP using the echo520 ultra-micro liquid pipetting system (final concentrations were 400 uM, 25 uM, 50 uM respectively). Shaked and mixed, then centrifuged, and reacted at 30° C. in the dark for 1.5 hours.

Detection reaction: Added 2.5 μL of Development Solution (1:128 dilution) to each well and incubated at 37° C. for 1 hour in the dark, then added 5 μL of Stop Reagent.

Plate reading: detected the fluorescence signal (excitation wavelength was 400 nm, emission wavelength were 460 nm, 535 nm) through a Perkin Elmer EnVision Multimode Plate Reader.

Calculation: Calculated the inhibition rate of each well through the full active well and the control signal well. The data analysis method was as follows:

Phosphorylation ratio=1−{(Emission ratio×F100%−C100%)/[C0%−C100%+Emission ratio×(F100%−F0%)]}×100;

Inhibition ratio=100×(1−Compound phosphorylation ratio/Negative control phosphorylation ratio).

The IC$_{50}$ value was calculated by medical drawing software (GraphPad Prism5.0).

The results of the kinase activity test are shown in Table 1.

TABLE 1

Test results of compounds effect on kinase activity (IC$_{50}$: nM)

| Compound No. | TRKA | TRKB | TRKC |
|---|---|---|---|
| XS116 | ** | ** | ** |
| XS2-161 | *** | **** | *** |
| XS2-106 | *** | **** | |
| XS2-109 | *** | **** | *** |
| XS2-112 | *** | *** | *** |
| XS3-23 | ** | ** | ** |
| XS3-61 | ** | ** | ** |
| XS4-80 | ** | | ** |
| XS4-81 | ** | | ** |
| XS4-72 | ** | ** | ** |
| XS4-76 | ** | ** | ** |
| XS4-77 | ** | ** | ** |
| XS3-68 | * | * | * |
| XS3-35 | * | ** | * |
| XS3-58 | ** | ** | ** |
| XS3-36 | ** | ** | * |
| XS3-57 | * | * | * |
| XS3-56 | ** | ** | ** |
| XS3-67 | * | ** | * |
| XS3-51 | ** | ** | * |
| XS3-52 | ** | ** | ** |
| XS3-55 | * | ** | ** |
| XS3-54 | * | ** | * |
| XS3-53 | * | ** | * |
| XS3-81 | * | * | * |
| XS3-130 | ** | ** | * |
| XS3-138 | ** | * | * |
| XS3-134 | ** | ** | ** |
| XS3-135 | ** | ** | ** |
| XS3-139 | ** | ** | ** |
| XS3-131 | ** | ** | ** |
| XS3-137 | ** | ** | ** |
| XS3-136 | ** | ** | ** |
| XS3-153 | ** | ** | ** |
| XS3-91 | * | * | * |
| XS3-87 | * | * | * |

IC$_{50}$: <10 nM = *; 10-100 nM = ; 100-1000 nM = *; >1 uM = ****.

It can be seen from the data in Table 1 that the Alkynylphenylbenzamide compounds of the present disclosure have strong inhibitory activity on TRKs kinase.

EXAMPLE 38: STUDY ON CELL PROLIFERATION INHIBITORY ACTIVITY BASED ON BA/F3-TRKS STABLE STRAIN

The BaF3 cells (mouse pre-B cells) used in this experiment were purchased from the Japanese Cell Bank. All of the monoclonal stable strains, BaF3-CD74-NTRK1, BaF3-ETV6-NTRK2 and BaF3-ETV6-NTRK3 were constructed by our laboratory, and were identified by experiments such as positive control, protein expression and gene sequencing.

The brief steps of stable strain construction were as follows: constructed pCDNA3.1(+) plasmid vector carrying genes such as CD74-NTRK1, ETV6-NTRK2, ETV6-NTRK3; the plasmid was electroporated into Ba/F3 cells using Amaxa® Cell Line Nucleofector® Kit V; 48 hours after electroporation, geneticin (G418) with a final concentration of 1000 μg/mL was added to screen for two weeks, and the interleukin 3 (IL3) was removed to continue screening to obtain polyclonal stable strains; and then single clones were selected by limiting dilution method; the stable strains were then identified by the positive drugs, Western Blot (WB), and gene sequencing; the correct monoclonal through identification can be used to study the cell proliferation inhibitory activity of the inhibitors.

Cell proliferation inhibitory activity study: The cells in logarithmic growth phase were seeded into 96-well plates at 8000-12000 cells/well, and the inhibitors at different concentrations of (0-10 μM) were added the next day, and the culture was continued for 72 hours; then 10 μL of Cell Counting Kit-8 Cell Counting Reagent (CCK-8 Reagent) was added to each well, and continued to incubate for 1-3 hours; then its absorbance at 450 nm and 650 nm were measured with a super microplate reader. The median inhibitory concentration (IC$_{50}$) was calculated using medical graphing software (GraphPad Prism 8.0.0).

The test results are shown in Table 2.

TABLE 2

Test results of compounds effect on cell viability (IC$_{50}$: nM)

| Compound No. | CD74-NTRK1 | ETV6-NTRK2 | ETV6-NTRK3 |
|---|---|---|---|
| XS116 | *** | *** | *** |
| XS2-161 | **** | **** | **** |
| XS2-106 | *** | *** | |
| XS2-112 | *** | *** | *** |
| XS3-23 | ** | ** | ** |
| XS3-61 | ** | | ** |
| XS4-80 | ** | ** | ** |
| XS4-81 | ** | ** | * |
| XS4-72 | ** | ** | * |
| XS4-76 | ** | ** | ** |
| XS4-77 | ** | ** | * |
| XS3-68 | * | ** | * |
| XS3-35 | ** | *** | ** |
| XS3-58 | *** | *** | ** |
| XS3-36 | ** | ** | ** |
| XS3-57 | ** | *** | ** |
| XS3-56 | *** | *** | ** |
| XS3-67 | *** | *** | ** |
| XS3-51 | *** | *** | ** |
| XS3-52 | ** | *** | ** |
| XS3-55 | ** | ** | ** |
| XS3-54 | ** | ** | ** |
| XS3-53 | ** | *** | ** |
| XS3-81 | ** | * | * |
| XS3-130 | ** | ** | ** |
| XS3-138 | ** | ** | * |
| XS3-134 | *** | *** | ** |
| XS3-135 | *** | *** | ** |
| XS3-139 | ** | ** | ** |
| XS3-131 | *** | *** | ** |
| XS3-137 | *** | *** | ** |
| XS3-136 | *** | *** | ** |
| XS3-153 | ** | ** | ** |
| XS3-87 | * | ** | * |
| XS3-91 | ** | ** | * |

IC$_{50}$: <10 nM = *; 10-100 nM = ; 100-1000 nM = *; >1 uM = ****.

It can be seen from the data in Table 2 that the Alkynylphenylbenzamide compounds of the present disclosure have strong inhibitory activity on the cell proliferation of the Ba/F3-TRKs stable strains.

EXAMPLE 39: STUDY ON THE INHIBITORY ACTIVITY OF DRUG-RESISTANT CELL PROLIFERATION BASED ON BA/F3-TRKS STABLE STRAIN

BaF3 cells (mouse pre-B cells) used in this experiment were purchased from Japan Cell Bank, all of the monoclonal stable strains, BaF3-CD74-NTRK1-G667C, BaF3-CD74-NTRK1-F589L, BaF3-CD74-NTRK1-G595R, BaF3-CD74-NTRK1-G667A, BaF3-CD74-NTRK1-V573M, BaF3-ETV6-NTRK2-G639R, BaF3-ETV6-NTRK2-G709C, BaF3-ETV6-NTRK2-V617M, BaF3-ETV6-NTRK2-F633L, BaF3-ETV6-NTRK3-G696C, BaF3-ETV6-NTRK3-G696A, BaF3-ETV6-NTRK3-G623R, BaF3-ETV6-NTRK3-G623E, BaF3-ETV6-NTRK3-F617L and BaF3-ETV6-NTRK3-V601M were constructed by our laboratory, and were identified by experiments such as positive control, protein expression and gene sequencing.

The brief steps for stable strains construction were as follows: constructed pCDNA3.1(+) plasmid vector carrying genes such as BaF3-CD74-NTRK1-G667C, BaF3-CD74-NTRK1-F589L, BaF3-CD74-NTRK1-G595R, BaF3-CD74-NTRK1-G667A, BaF3-CD74-NTRK1-V573M, BaF3-ETV6-NTRK2-G639R, BaF3-ETV6-NTRK2-G709C, BaF3-ETV6-NTRK2-V617M, BaF3-ETV6-NTRK2-F633L, BaF3-ETV6-NTRK3-G696C, BaF3-ETV6-NTRK3-G696A, BaF3-ETV6-NTRK3-G623R, BaF3-ETV6-NTRK3-G623E, BaF3-ETV6-NTRK3-F617L and BaF3-ETV6-NTRK3-V601M; the plasmid was electroporated into Ba/F3 cells using Amaxa® Cell Line Nucleofector® Kit V; 48 hours after of electroporation, geneticin (G418) with a final concentration of 1000 μg/mL was added to screen for two weeks, and the interleukin 3 (IL3) was removed to continue screening to obtain polyclonal stable strains; and then single clones were selected by limiting dilution method; the stable strains were then identified by the positive drugs, Western Blot (WB), and gene sequencing; the correct monoclonal through identification can be used to study the cell proliferation inhibitory activity of the inhibitors.

Cell proliferation inhibitory activity study: The cells in logarithmic growth phase were seeded into 96-well plates at 8000-12000 cells/well, and the inhibitors at different concentrations of (0-10 μM) were added the next day, and the culture was continued for 72 hours; then 10 μL of Cell Counting Kit-8 Cell Counting Reagent (CCK-8 Reagent) was added to each well, and continued to incubate for 1-3 hours; then its absorbance at 450 nm and 650 nm were measured with a super microplate reader. The median inhibitory concentration (IC$_{50}$) was calculated using medical graphing software (GraphPad Prism 8.0.0).

The test results are shown in Table 3.

TABLE 3

Test results of compounds effect on drug-resistant cell viability (IC$_{50}$: nM)

| Compound No. | XS3-55 | XS3-68 | XS3-81 | XS3-87 |
|---|---|---|---|---|
| BaF3-CD74-NTRK1-G667C | * | * | * | * |
| BaF3-CD74-NTRK1-G667A | * | * | * | * |
| BaF3-CD74-NTRK1-G595R | **** | *** | *** | *** |
| BaF3-CD74-NTRK1-F589L | *** | *** | *** | ** |
| BaF3-CD74-NTRK1-V573M | ** | ** | * | * |
| BaF3-ETV6-NTRK2-G639R | *** | ** | ** | ** |
| BaF3-ETV6-NTRK2-F633L | *** | *** | *** | ** |
| BaF3-ETV6-NTRK2-V617M | * | * | * | * |
| BaF3-ETV6-NTRK2-G709C | * | * | ** | * |
| BaF3-ETV6-NTRK3-G696C | * | * | * | * |
| BaF3-ETV6-NTRK3-G696A | * | * | * | * |
| BaF3-ETV6-NTRK3-G623R | *** | ** | ** | ** |
| BaF3-ETV6-NTRK3-G623E | * | * | * | * |
| BaF3-ETV6-NTRK3-F617L | ** | ** | ** | * |
| BaF3-ETV6-NTRK3-V601M | * | * | * | * |

IC$_{50}$: <10 nM = *; 10-100 nM = ; 100-1000 nM = *; >1 uM = ****.

It can be seen from the data in Table 3 that the Alkynylphenylbenzamide compounds of the present disclosure have strong inhibitory activity on the proliferation of drug-resistant cells of the Ba/F3-TRKs stable strains.

EXAMPLE 40: IC$_{50}$ DETERMINATION OF COMPOUND XS3-55 KINASE SELECTIVITY

Kinase activity detection: Applying Z'-LYTE™ technology (detection by fluorescence, enzyme-coupled format, based on the difference in sensitivity of phosphorylated and non-phosphorylated peptides to proteolytic cleavage), based on the principle of fluorescence resonance energy transfer (FRET), using Z'-LYTE™ FRET peptide substrates, and the inhibitory activity of Compound XS3-55 and control molecules XS4-128 and Ponatinib against Bcr-Abl, SRC, RET, PDGFRA, PDGFRB, VEGFR2 and KIT kinases was detected through secondary reaction.

Wherein, the structural formula of Compound XS4-128 is as follows:

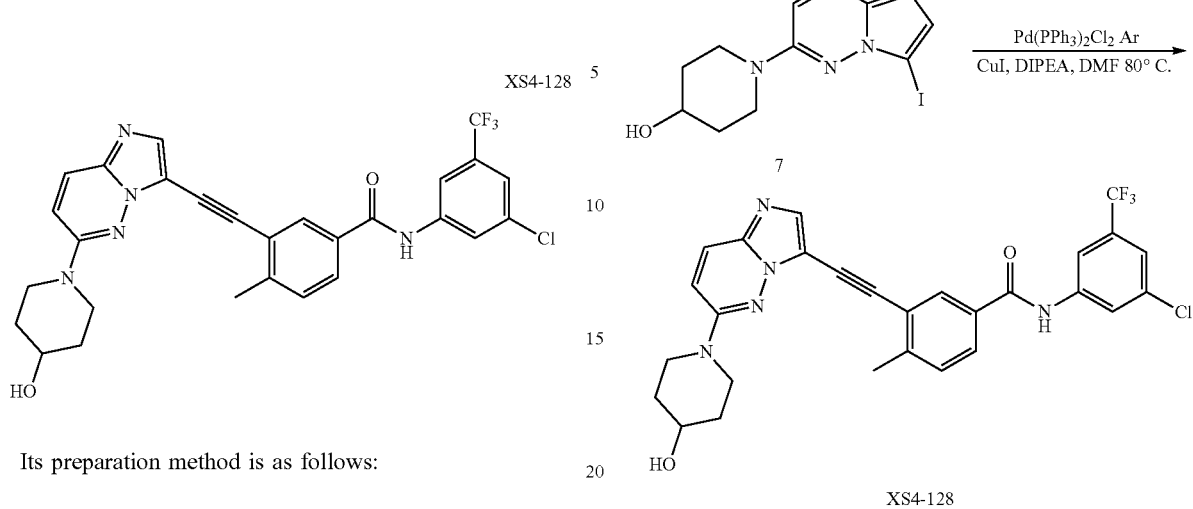

Its preparation method is as follows:

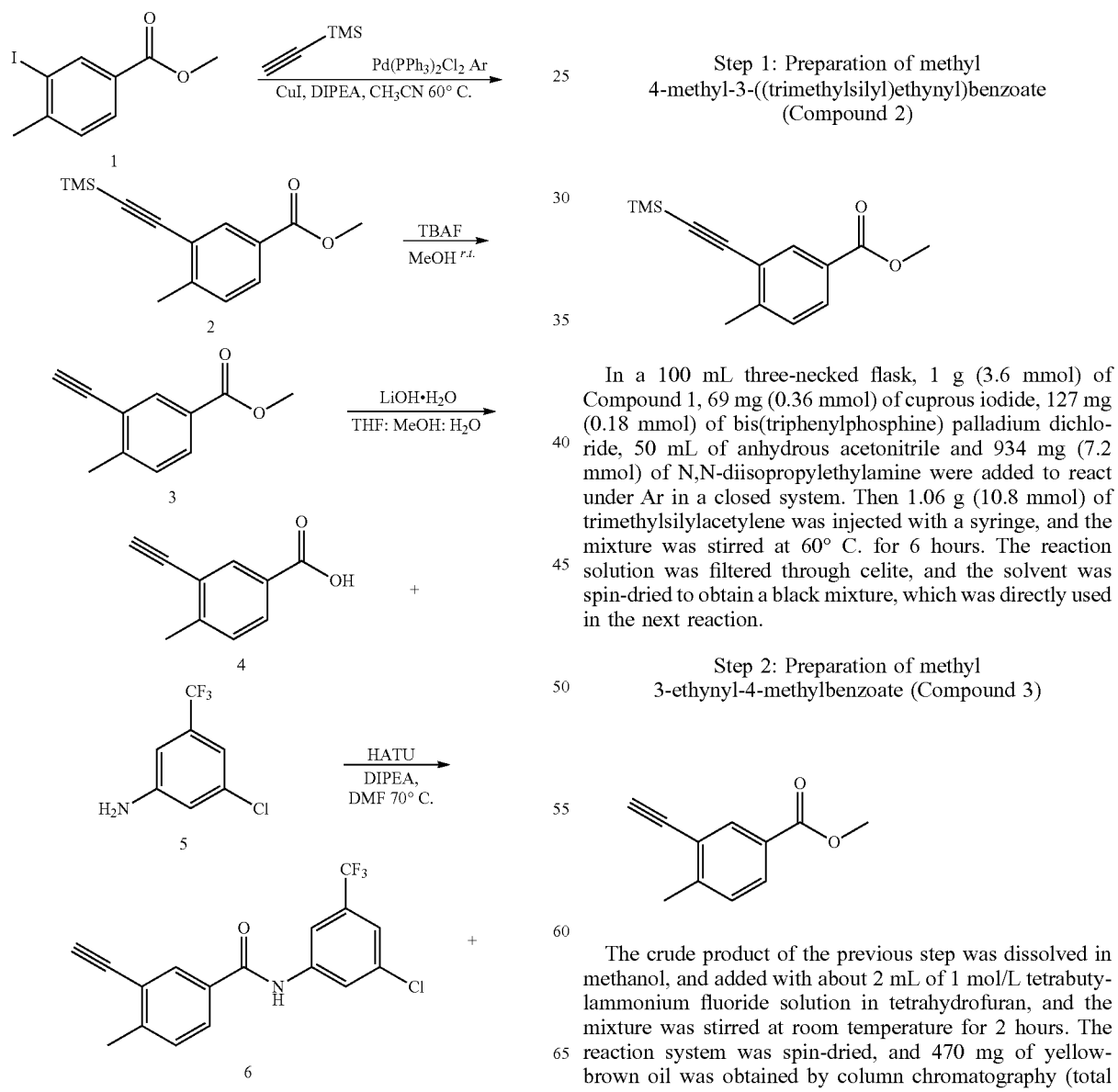

Step 1: Preparation of methyl 4-methyl-3-((trimethylsilyl)ethynyl)benzoate (Compound 2)

In a 100 mL three-necked flask, 1 g (3.6 mmol) of Compound 1, 69 mg (0.36 mmol) of cuprous iodide, 127 mg (0.18 mmol) of bis(triphenylphosphine) palladium dichloride, 50 mL of anhydrous acetonitrile and 934 mg (7.2 mmol) of N,N-diisopropylethylamine were added to react under Ar in a closed system. Then 1.06 g (10.8 mmol) of trimethylsilylacetylene was injected with a syringe, and the mixture was stirred at 60° C. for 6 hours. The reaction solution was filtered through celite, and the solvent was spin-dried to obtain a black mixture, which was directly used in the next reaction.

Step 2: Preparation of methyl 3-ethynyl-4-methylbenzoate (Compound 3)

The crude product of the previous step was dissolved in methanol, and added with about 2 mL of 1 mol/L tetrabutylammonium fluoride solution in tetrahydrofuran, and the mixture was stirred at room temperature for 2 hours. The reaction system was spin-dried, and 470 mg of yellow-brown oil was obtained by column chromatography (total yield of two steps was 75%).

$^1$H NMR (400 MHz, DMSO-d$_6$) δ 8.06 (d, J=1.5 Hz, 1H), 7.76 (dd, J=7.5, 1.5 Hz, 1H), 7.25 (dd, J=7.5, 1.0 Hz, 1H), 4.25 (s, 1H), 3.86 (s, 3H), 2.39 (s, 3H). LC-MS (ESI) m/z 175.5 [M+H]$^+$.

Step 3: Preparation of 3-ethynyl-4-methylbenzoic acid (Compound 4)

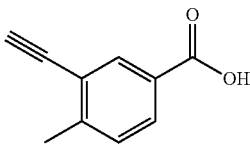

400 mg (2.29 mmol) of Compound 3 was dissolved in a mixed solvent of tetrahydrofuran, methanol and water with a volume ratio of 10:1:5, then 482 mg (11.4 mmol) of lithium hydroxide hydrate was added, and the mixture was stirred at 60° C. for 1 hour. The reaction system was filtered and spin-dried, and then added with 4M hydrochloric acid solution until the system became acidic. At this time a white solid is precipitated, which was collected by filtration, and dried to obtain 350 mg of white solid (yield: 96%).

$^1$H NMR (400 MHz, DMSO-d$_6$) δ 13.02 (s, 1H), 7.93 (d, J=1.8 Hz, 1H), 7.85 (dd, J=7.9, 1.9 Hz, 1H), 7.43 (d, J=8.0 Hz, 1H), 4.48 (s, 1H), 2.45 (s, 3H). LC-MS (ESI) m/z 160.9 [M+H]$^+$.

Step 4: Preparation of N-(3-chloro-5-(trifluoromethyl)phenyl)-3-ethynyl-4-methylbenzamide (Compound 6)

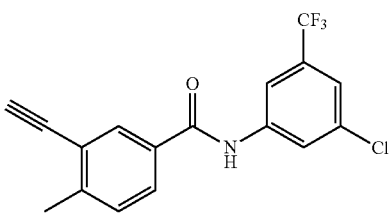 [SMILES: C#Cc1cc(C(=O)Nc2cc(Cl)cc(C(F)(F)F)c2)ccc1C]

300 mg (1.9 mmol) of Compound 4 and 305 mg (1.6 mmol) of Compound 5 were dissolved in 20 mL of N,N-dimethylformamide (DMF), added with 912 mg (2.4 mmol) of 2-(7-Azabenzotriazole)-N,N,N',N'-tetramethylurea hexafluorophosphate (HATU) and 413 mg (3.2 mmol) of N,N-diisopropylethyl acetate amine, and the mixture was heated and stirred at 70° C. for 2 hours. The reaction system was spin-dried, and added with water, extracted with ethyl acetate, rinsed with water, dried over anhydrous sodium sulfate. The solvent was spin-dried, and 340 mg of yellow oil was obtained by column chromatography (yield: 63%).

$^1$H NMR (400 MHz, DMSO-d$_6$) δ 10.88 (s, 1H), 8.11 (d, J=1.8 Hz, 2H), 7.64-7.57 (m, 2H), 7.54 (dd, J=7.7, 1.4 Hz, 1H), 7.36 (t, J=7.7 Hz, 1H), 4.51 (s, 1H), 2.47 (s, 3H). MS (ESI) m/z 335.8 [M−H]$^−$.

Step 5: Preparation of N-(3-Chloro-5-(trifluoromethyl)phenyl)-3-((6-(4-hydroxypiperidin-1-yl)imidazo[1,2-B]pyridazine-3-yl)ethynyl)-4-methylbenzamide (XS4-128)

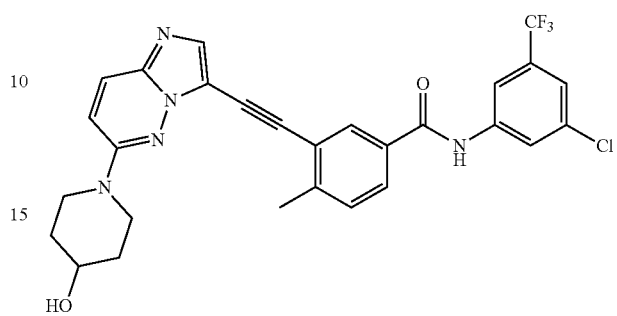

70 mg (0.2 mmol) of Compound 6 and 83 mg (1.2 mmol) of Compound 7 were dissolved in 10 mL of anhydrous N,N-dimethylformamide (DMF), and then added with 8 mg (0.016 mmol) of cuprous iodide, 19 mg (0.01 mmol) of bis(triphenylphosphine)palladium dichloride and 145 mg (0.4 mmol) of N,N-diisopropylethylamine, and reacted under Ar in a closed system. The mixture was heated and stirred at 80° C. and reacted overnight. The reaction solution was filtered through celite, the solvent was spin-dried, and 80 mg of yellow-white solid was obtained by column chromatography (yield: 73%).

$^1$H NMR (400 MHz, DMSO-d$_6$) δ 10.66 (s, 1H), 8.25 (s, 2H), 8.16 (d, J=9.2 Hz, 2H), 7.96 (s, 1H), 7.90 (dd, J=8.0, 1.9 Hz, 1H), 7.55 (s, 1H), 7.52 (d, J=8.1 Hz, 1H), 7.34 (s, 1H), 4.75 (d, J=4.2 Hz, 1H), 3.98 (d, J=14.5 Hz, 2H), 3.80-3.71 (m, 1H), 3.26 (t, J=11.5 Hz, 2H), 2.61 (s, 3H), 1.89-1.78 (m, 2H), 1.54-1.40 (m, 2H). HRMS (ESI) for C$_{28}$H$_{23}$ClF$_3$N$_5$O$_2$ [M+H]$^+$: calcd 554.1565, found 554.1562.

Enzymatic reaction: In a 384-well plate, added 5 μL of enzyme-substrate system [50 mM 4-hydroxyethylpiperazineethanesulfonic acid (HEPES) pH 7.5, 0.01% BRIJ-35, 10 mM of magnesium chloride (MgCl2), 1 mM of ethylene glycol bis(2-aminoethyl ether)tetraacetic acid (EGTA), 2 μM of Tyr 01 peptide substrate], transferred 5 nL of compound (concentration gradient) using an Echo520 Ultra-Micro Liquid Pipetting System. After shaking at room temperature for 10-20 minutes, transferred 200 nL, 12.5 nL, 25 nL ATP using the Echo520 Ultra-Micro Liquid Pipetting System (final concentrations are 400 uM, 25 uM, 50 uM respectively). Shaked and mixed, then centrifuged, and reacted at 30° C. in the dark for 1.5 hours.

Detection reaction: Added 2.5 μL of Development Solution (1:128 dilution) to each well and incubated at 37° C. for 1 hour in the dark, then added 5 μL of Stop Reagent.

Plate reading: detected the fluorescence signal (excitation wavelength was 400 nm, emission wavelength was 460 nm, 535 nm) through a Perkin Elmer EnVision Multimode Plate Reader.

Calculation: Calculated the inhibition rate of each well through the full active well and the control signal well. The data analysis method was as follows:

Phosphorylation ratio=1−{(Emission ratio×F100%−C100%)/[C0%−C100%+Emission ratio×(F100%−F0%)]}×100;

Inhibition ratio=100×(1−Compound phosphorylation ratio/Negative control phosphorylation ratio).

The IC$_{50}$ value was calculated by medical drawing software (GraphPad Prism5.0).

The results of the kinase activity test are shown in Table 4.

TABLE 4

Test Results of compounds kinase selective activity detection (IC$_{50}$: nM)

| Kinase | XS3-55 | XS4-128 | Ponatinib |
|---|---|---|---|
| Bcr-Abl | >10000 | 128.8 | 3.9 |
| SRC | 526.3 | 20.3 | 2.0 |
| RET | >10000 | 10.7 | 3.3 |
| VEGFR2 | 832.7 | 18.9 | 3.3 |

TABLE 4-continued

Test Results of compounds kinase selective activity detection (IC$_{50}$: nM)

| Kinase | XS3-55 | XS4-128 | Ponatinib |
|---|---|---|---|
| Kit | 1669 | 93.5 | 25.1 |
| PDGFRA | 5887 | 19.9 | 3.9 |
| PDGFRB | >10000 | 118.9 | 18.0 |

It can be seen from the data in Table 4 that the representative compound XS3-55 of the Alkynylphenylbenzamide compounds of the present disclosure has weak inhibitory activity on a variety of representative tyrosine kinases other than TRKA, TRKB and TRKC. It has good kinase selectivity, and its kinase selectivity is much better than that of compounds XS4-128 and Ponatinib. Therefore, the Alkynylphenylbenzamide compounds of the present disclosure have good selectivity and low toxic and side effects.

EXAMPLE 41: PHARMACOKINETIC EVALUATION

Pharmacokinetic and oral bioavailability tests were performed in SD rats. According to the drug's solubility, the drug was administered orally and intravenously as a single dose. Animal blood samples were collected at different time points (0, 0.5, 1, 2, 4, 6, 8, 24 hours), and added with heparin for anticoagulation, then centrifuged to obtain the supernatant. Blood samples were analyzed by HPLC-MS, and DAS2.1 was used for data analysis to detect half-life (T½), maximum blood concentration (Cmax), peak time (Tmax), area under the curve (AUC), and bioavailability (BA) and other pharmacokinetic data. The pharmacokinetic data results of compound XS3-55 and compound 9o (European Journal of Medicinal Chemistry 179(2019) 470-482.) are shown in Table 5:

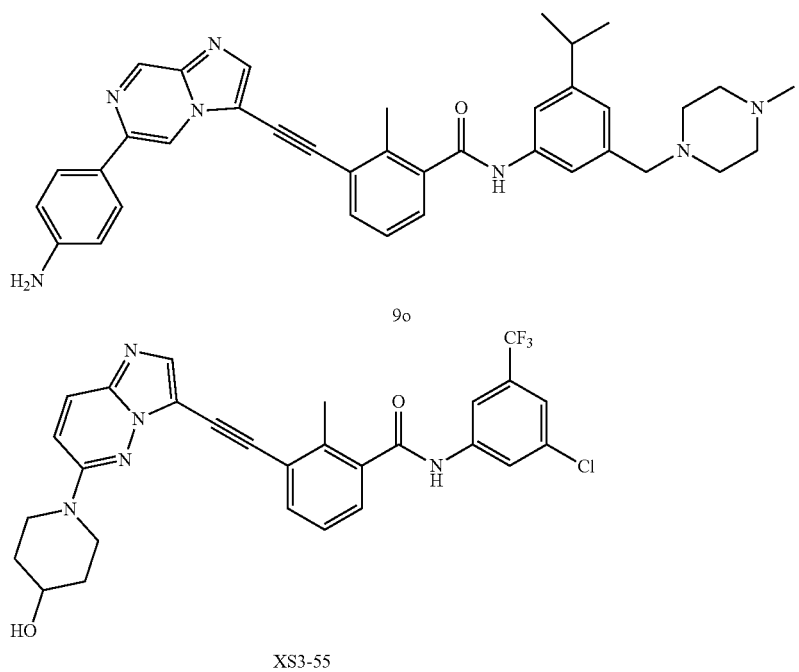

9o

XS3-55

TABLE 5

| | Compound | | | |
|---|---|---|---|---|
| | Compound 9o | | Compound XS3-55 | |
| | Administration way | | | |
| | Intravenous injection | Oral | Intravenous injection | Oral |
| Dose (mg/kg) | 5 | 25 | 2.0 | 10.0 |
| half-life (h) | 2.03 | 4.77 | 16.07 | 15.19 |
| Tmax (h) | 0.083 | 2 | 0.08 | 4.00 |
| Cmax (ng/mL) | 1968.37 | 63.3 | 46123.74 | 44066.54 |
| AUC (0-t)(h*ng/mL) | 804.65 | 431.49 | 358128.95 | 560764.28 |
| AUC (0-∞) (h*ng/mL) | 810.45 | 445.18 | 548798.57 | 878346.33 |
| Clearance rate (mL/h/kg) | 1260.51 | Nd | 3.65 | nd |
| BA (%) | | 10.72 | | 31.32 |

Compound XS3-55 had strong inhibitory activity on TRKs kinase, and had strong inhibitory activity on the proliferation of wild-type and drug-resistant cells of Ba/F3-TRKs stable strain as well. It also had good oral absorption properties. Under the oral dose of 10 mg/kg in rats, the half-life of compound XS3-55 was 15.19 hours, the Cmax was as high as 44066.54 ng/mL, and the AUC was as high as 878346.33 h*ng/mL, the pharmacokinetic properties were significantly higher than that of the control compound 9o.

EXAMPLE 42: IN VIVO ANTITUMOR ACTIVITY OF COMPOUND XS3-55

The in vivo antitumor efficacy of compound XS3-55 was evaluated in a Ba/F3-CD74-TRKAG$^{667C}$ allograft mouse model by oral administration. The cultured BaF3-CD74-TRKAG$^{667C}$ cells were collected and centrifuged. After washed twice with normal saline, the cells were adjusted to a density of $1\times10^7$ cells/mL and placed on ice, and injected subcutaneously into the right axilla of CB17-SCID female mice (purchased from Viton Lever, Beijing, 6-8 weeks old) as soon as possible, with 200 μL each injection. After 9 days of modeling, when the tumor volume grew to about 200 mm$^3$, the mice were randomly divided into groups and started to be administered, including a control group with 8 mice and 4 groups of compound XS3-55 doses (50, 25, 12.5, 6.25 mg/kg) with 6 mice in each group.

The administration method was as follows: according to the dosage, an appropriate amount of Compound XS3-55 powder was weighed and dissolved in a mixed solvent of 2% dimethyl sulfoxide (DMSO)+20% hydrogenated castor oil+ 8% absolute ethanol+70% normal saline, to obtain light yellow to yellow transparent liquid, orally administered once a day. The control group was given the same volume of mixed solvent orally. Body weight and tumor volume were recorded every two days.

Figure 2:
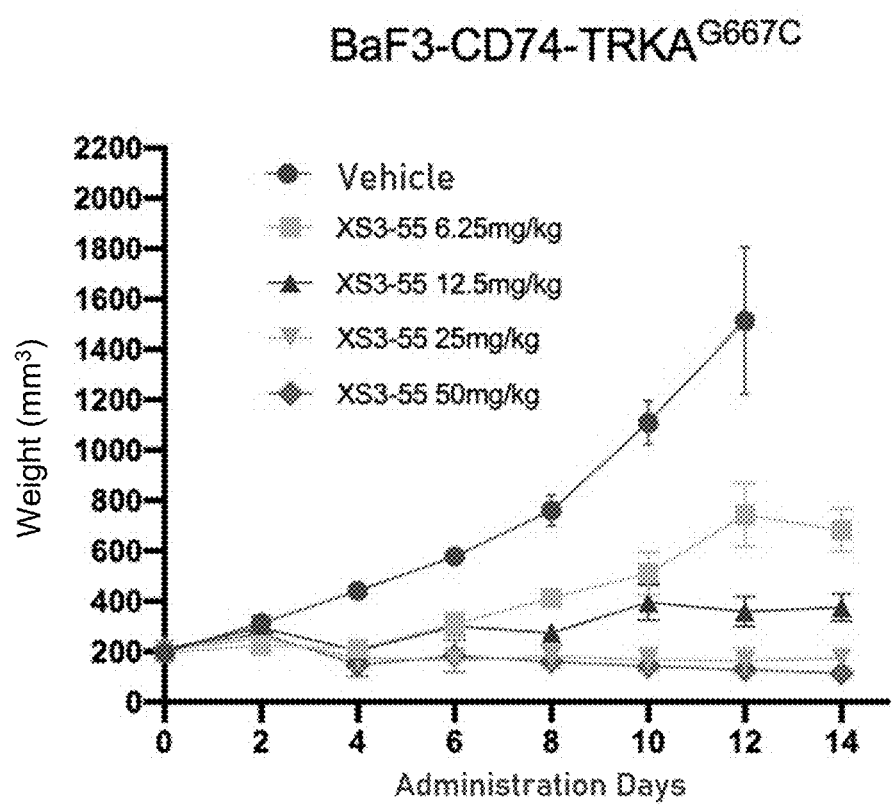
FIG. 2 shows the effect of compound XS3-55 on the body weight of mice.

The results are shown in FIG. 1 and FIG. 2: Compound XS3-55 was administered once daily for two weeks, inhibited the growth of the CD74 TRKAG$^{667C}$ mutation-bearing allograft mouse model in a dose-dependent manner. Significant reductions in tumor size were observed after 2 days of treatment at the lowest dose of 6.25 mg/kg. After treatment for 12 days, Compound XS3-55 exhibited excellent in vivo antitumor efficacy at doses of 6.25 mg/kg/day, 12.5 mg/kg/day, 25 mg/kg/day and 50 mg/kg/day, with TGIs being 50.9%, 76.3%, 89.2 and 91.6%, respectively; while the control mice died on day 14. Meanwhile, the in vivo studies showed that four different doses of compound XS3-55 had no obvious adverse effect on mouse body weight (FIG. 1), which indicated that Compound XS3-55 had a good safety profile.

The technical features of the above embodiments can be combined arbitrarily. To simplify the description, all possible combinations of the technical features of the above embodiments are not described. However, as long as there is no contradiction in the combination of these technical features, they should be considered to be the scope recorded in the description.

The above embodiments express several implementations of the present disclosure only. The description of the embodiments is relatively specific and detailed, but may not therefore be construed as the limitation on the patent scope of the present disclosure. It should be noted that a person of ordinary skill in the art may further make several variations and improvements without departing from the concept of the present disclosure. these variations and improvements all fall within the protection scope of the present disclosure. Therefore, the patent protection scope of the present disclosure shall be defined by the appended claims.

What is claimed is:

1. Alkynylphenylbenzamide compounds with the structure shown in Formula (I) or their pharmaceutically acceptable salts, or stereoisomer or prodrug molecules,

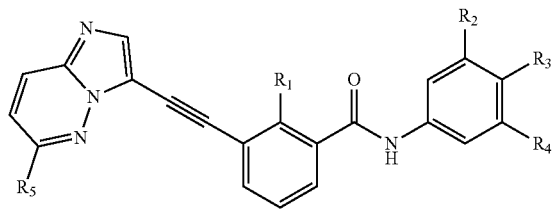

(I)

wherein, $R_1$ is selected from: $C_1$~$C_{20}$ alkyl;
$R_2$ is selected from: H, halogen, $C_1$~$C_{20}$ alkyl, $C_1$~$C_{20}$ alkoxy and halogen-substituted $C_1$~$C_{20}$ alkyl;
$R_3$ is selected from: H, fluorine-substituted $C_1$-$C_4$ alkyl, and substituted or unsubstituted 5-6 membered heterocyclic group containing 1-3 N ring atoms;
$R_4$ is selected from: H, halogen, nitro, substituted or unsubstituted $C_1$~$C_{20}$ alkyl, substituted or unsubstituted $C_1$~$C_{20}$ alkoxy, substituted or unsubstituted 5-10 membered heterocyclyl containing 1-3 N ring atoms, and substituted or unsubstituted 5-10 membered heteroaryl containing 1-3 N ring atoms;
$R_5$ is —$NR_6R_7$;
wherein, $R_6$ and $R_7$ are independently selected from: —$(CH_2)_m NR_8R_9$, —$(CH_2)_n CR_{10}R_{11}R_{12}$, and —$(CH_2)_p OR_{12}$; or $R_6$ and $R_7$ together with the attached nitrogen atom form a substituted or unsubstituted monocyclic ring, fused ring, spiro ring or bridged ring containing heteroatom;
$R_8$ and $R_9$ are independently selected from: H, and $C_1$~$C_{20}$ alkyl; or $R_8$ and $R_9$ together with the attached nitrogen atom form a substituted or unsubstituted monocyclic ring, fused ring, spiro ring or bridged ring containing 1-3 heteroatoms;
$R_{10}$ and $R_{11}$ together with the attached carbon atom form a substituted or unsubstituted monocyclic ring, fused ring, spiro ring or bridged ring containing 1-3 heteroatoms;
$R_{12}$ is selected from: H, and $C_1$~$C_{20}$ alkyl;
m, n, and p are each independently selected from: an integer from 0 to 10.

2. The Alkynylphenylbenzamide compounds or their pharmaceutically acceptable salts or stereoisomers or prodrug molecules according to claim 1, wherein
$R_4$ is selected from: H, halogen, nitro, $C_1$~$C_8$ alkyl, halogen-substituted $C_1$~$C_8$ alkyl, $C_1$~$C_8$ alkoxy, halogen-substituted $C_1$~$C_8$ alkoxy, —$(CH_2)_x NR_{17}R_{18}$, 5-6 membered heterocyclyl group containing 1-3 N ring atoms and substituted or unsubstituted by 1-5 $R_{19}$, and 5-6-membered heteroaryl containing 1-3 N ring atoms and substituted or unsubstituted by 1-5 $R_{19}$; wherein, x is an integer from 1 to 5;
$R_{17}$ and $R_{18}$ together with the attached nitrogen atom form a 1-5 $R_{19}$ substituted or unsubstituted morpholinyl, pyrrolidinyl, piperidinyl or piperazinyl;
each $R_{19}$ is independently selected from: $C_1$-$C_5$ alkyl.

3. The Alkynylphenylbenzamide compounds or their pharmaceutically acceptable salts or stereoisomers or prodrug molecules according to claim 2, wherein
$R_4$ is selected from: H, halogen, nitro, $C_1$~$C_4$ alkyl, halogen-substituted $C_1$~$C_4$ alkyl, $C_1$~$C_4$ alkoxy, halogen-substituted $C_1$~$C_4$ alkoxy, —$(CH_2)_x NR_{17}R_{18}$, and 1-3 $R_{19}$ substituted or unsubstituted imidazolyl;
wherein, x is 1, 2 or 3;

$R_{17}$ and $R_{18}$ together with the attached nitrogen atom form a piperazinyl substituted or unsubstituted by 1-3 $R_{19}$;
each $R_{19}$ is independently selected from: $C_1$-$C_5$ alkyl.

4. The Alkynylphenylbenzamide compounds or their pharmaceutically acceptable salts or stereoisomers or prodrug molecules according to claim 3, wherein
$R_4$ is selected from: H, halogen, nitro, methyl, ethyl, propyl, methoxy, ethoxy, propoxy, trifluoromethyl, trifluoroethyl,

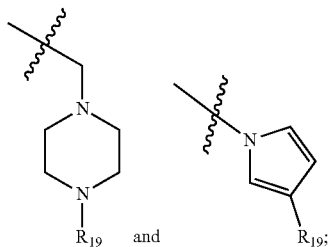

each $R_{19}$ is independently selected from: methyl, ethyl, and propyl.

5. The Alkynylphenylbenzamide compounds or their pharmaceutically acceptable salts or stereoisomers or prodrug molecules according to claim 1, wherein
$R_6$ and $R_7$ are independently selected from: —$(CH_2)_m NR_8R_9$, —$(CH_2)_n CR_{10}R_{11}R_{12}$, and —$(CH_2)_p OR_{12}$; or $R_6$ and $R_7$ together with the attached nitrogen atom form a 3-15 membered monocyclic ring, fused ring, spiro ring or bridged ring containing 1-3 heteroatoms and substituted or unsubstituted by 1-5 $R_{13}$; wherein, the heteroatoms are selected from: O, N, S;
$R_8$ and $R_9$ are independently selected from: H, and $C_1$-$C_5$ alkyl; or $R_8$ and $R_9$ together with the attached nitrogen atom form a 3-10 membered monocyclic ring, fused ring, spiro ring or bridged ring containing 1-3 heteroatoms and substituted or unsubstituted by 1-5 $R_{13}$, wherein, the heteroatoms are selected from: O, and N;
$R_{10}$ and $R_{11}$ together with the attached carbon atoms form a 3-10 membered monocyclic ring, fused ring, spiro ring or bridged ring containing 1-3 heteroatoms and substituted or unsubstituted by 1-5 $R_{13}$, wherein, the heteroatoms are selected from: O, and N;
$R_{12}$ is selected from: H, and $C_1$-$C_5$ alkyl;
each $R_{13}$ is independently selected from: H, $C_1$-$C_5$ alkyl, $C_1$-$C_5$ alkanoyl, hydroxy, hydroxy-substituted $C_1$-$C_5$ alkyl, amino-substituted $C_1$-$C_5$ alkyl, amino-substituted $C_1$-$C_5$ alkoxy, $C_3$-$C_7$ cycloalkyl-substituted $C_1$-$C_3$ alkyl, —$NR_{15}R_{16}$, and 3-10 membered monocyclic ring, fused ring, spiro ring or bridged ring containing 1-3 heteroatoms and substituted or unsubstituted by 1-5 $R_{14}$, wherein, the heteroatoms are selected from: O, and N;
$R_{14}$, $R_{15}$ and $R_{16}$ are independently selected from: H, and $C_1$-$C_5$ alkyl;
m, n and p are each independently selected from: an integer from 0 to 5.

6. The Alkynylphenylbenzamide compounds or their pharmaceutically acceptable salts or stereoisomers or prodrug molecules according to claim 5, wherein
$R_6$ and $R_7$ are independently selected from: —$(CH_2)_m NR_8R_9$, and —$(CH_2)_p OR_{12}$; or $R_6$ and $R_7$ together with the attached nitrogen atom form a 1-3 $R_{13}$ substituted or unsubstituted morpholinyl, pyrrolidinyl, piperidinyl or piperazinyl;

$R_8$ and $R_9$ are independently selected from: H, and $C_1$-$C_5$ alkyl; or $R_8$ and $R_9$ together with the attached nitrogen atom form a 1-5 $R_{13}$ substituted or unsubstituted morpholinyl, pyrrolidinyl, piperidinyl or piperazinyl;
$R_{12}$ is selected from: H, and $C_1$-$C_5$ alkyl;
each $R_{13}$ is independently selected from: H, $C_1$-$C_5$ alkyl, $C_1$-$C_5$ alkanoyl, hydroxy, —$NR_{15}R_{16}$, oxetanyl substituted or unsubstituted by 1-2 $R_{14}$, and morpholinyl substituted or unsubstituted by 1-4 $R_{14}$;
$R_{14}$, $R_{15}$ and $R_{16}$ are independently selected from: H, and $C_1$-$C_3$ alkyl;
m and p are each independently selected from: 1, 2, 3, 4 and 5.

7. The Alkynylphenylbenzamide compounds or their pharmaceutically acceptable salts or stereoisomers or prodrug molecules according to claim 5, wherein
$R_5$ is selected from any one of the following groups:

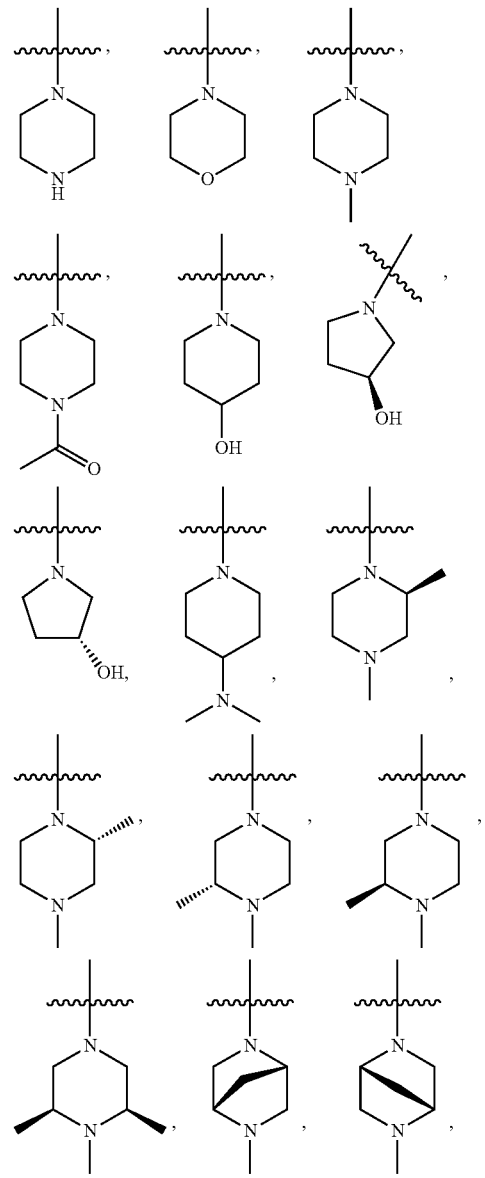

-continued
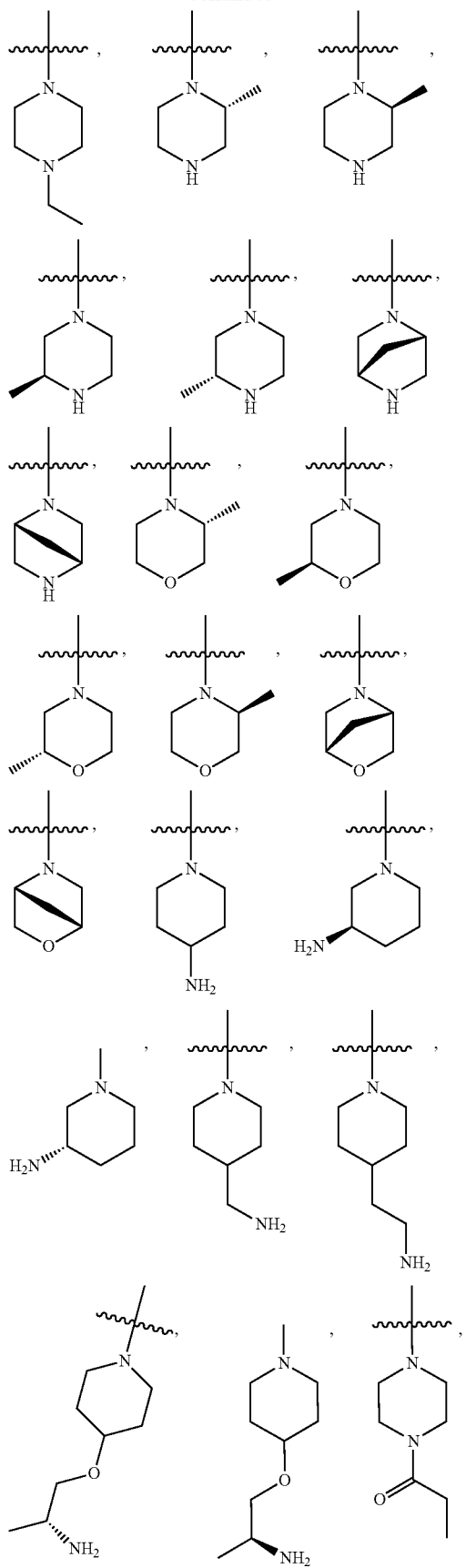
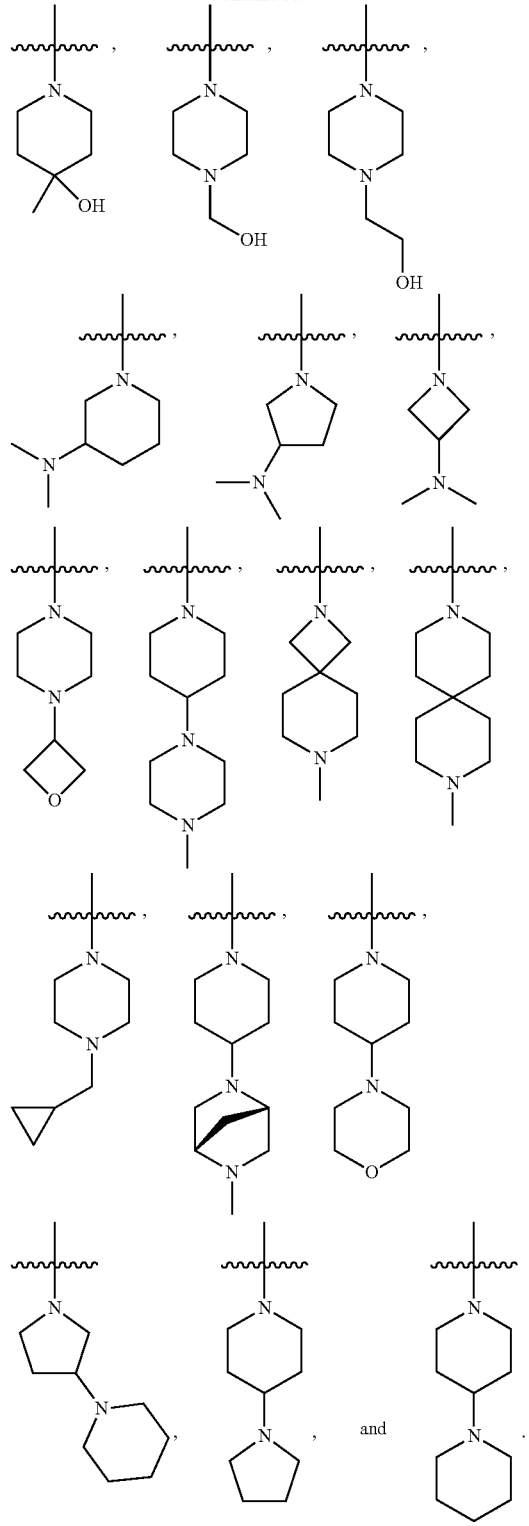
8. The Alkynylphenylbenzamide compounds or their pharmaceutically acceptable salts or stereoisomers or prodrug molecules according to claim 1, wherein
$R_4$ is halogen;
$R_5$ is —$NR_6R_7$;
$R_6$, $R_7$ are independently selected from: —$(CH_2)_mNR_8R_9$, and —$(CH_2)_pOR_{12}$; or $R_6$ and $R_7$ together with the attached nitrogen atom form a 1-3 $R_{13}$ substituted or unsubstituted morpholinyl, pyrrolidinyl, piperidinyl or piperazinyl;

$R_8$ and $R_9$ are independently selected from: H, and $C_1$-$C_3$ alkyl; or $R_8$ and $R_9$ together with the attached nitrogen atom form a 1-2 $R_{13}$ substituted or unsubstituted morpholinyl, pyrrolidinyl, piperidinyl or piperazinyl;

$R_{12}$ is selected from: H, and $C_1$-$C_3$ alkyl;

each $R_{13}$ is independently selected from: H, $C_1$-$C_3$ alkyl, acetyl, hydroxyl, —$NR_{15}R_{16}$, oxetanyl, and morpholinyl;

$R_{15}$ and $R_{16}$ are independently selected from: H, and $C_1$-$C_3$ alkyl;

m and p are each independently selected from: 2, 3 and 4.

9. The Alkynylphenylbenzamide compounds or their pharmaceutically acceptable salts or stereoisomers or prodrug molecules according to claim 8, wherein $R_4$ is Cl, $R_5$ is selected from:

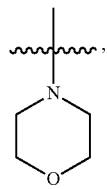 ,  , 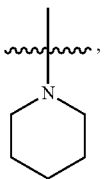 , 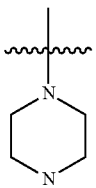 ,

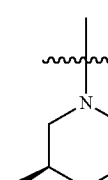 , 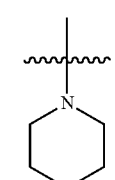 , 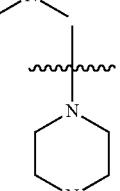 ,

 ,  , and  .

10. The Alkynylphenylbenzamide compounds or their pharmaceutically acceptable salts or prodrug molecules according to claim 1, wherein $R_4$ is selected from: H, halogen, methyl, methoxy, trifluoromethyl, nitro, and

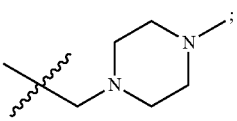 [SMILES: *CN1CCN(C)CC1] ;

$R_5$ is

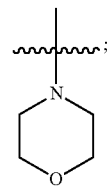 [SMILES: *N1CCOCC1] ;

or $R_4$ is selected from H, and

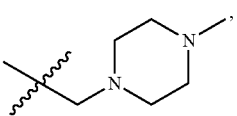 [SMILES: *CN1CCN(C)CC1] , $R_5$ is selected from

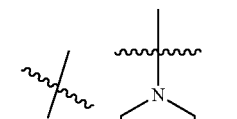 , 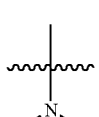 , and 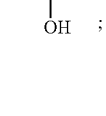 ;

or $R_4$ is

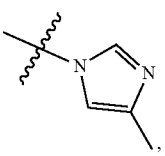 , $R_5$ is selected from

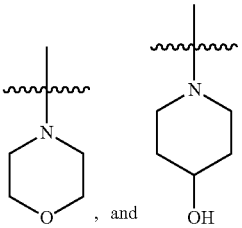 , and  .

11. The Alkynylphenylbenzamide compounds or their pharmaceutically acceptable salts or stereoisomers or prodrug molecules according to claim 1, wherein
  $R_1$ is selected from: $C_1$~$C_4$ alkyl; and/or,
  $R_2$ is selected from: H, halogen, $C_1$-$C_4$ alkyl, halogen-substituted $C_1$-$C_4$ alkyl, and $C_1$-$C_4$ alkoxy.

12. The Alkynylphenylbenzamide compounds or their pharmaceutically acceptable salts or stereoisomers or prodrug molecules according to claim 11, wherein
  $R_1$ is selected from: methyl, ethyl, isopropyl, and tert-butyl; and/or,
  $R_2$ is selected from: hydrogen, fluorine, methyl, ethyl, isopropyl, tert-butyl, difluoromethyl, difluoroethyl, trifluoromethyl and trifluoroethyl.

13. The Alkynylphenylbenzamide compounds or their pharmaceutically acceptable salts or stereoisomers or prodrug molecules according to claim 1, wherein
  $R_3$ is selected from: H, difluoromethyl, difluoroethyl, trifluoromethyl and trifluoroethyl.

14. The Alkynylphenylbenzamide compounds or their pharmaceutically acceptable salts or stereoisomers or prodrug molecules according to claim 1, wherein the Alkynylphenylbenzamide compounds have the structure shown in Formula (II):

15. The Alkynylphenylbenzamide compounds or their pharmaceutically acceptable salts or stereoisomers or prodrug molecules according to claim 1, wherein the Alkynylphenylbenzamide compounds are selected from the following compounds:

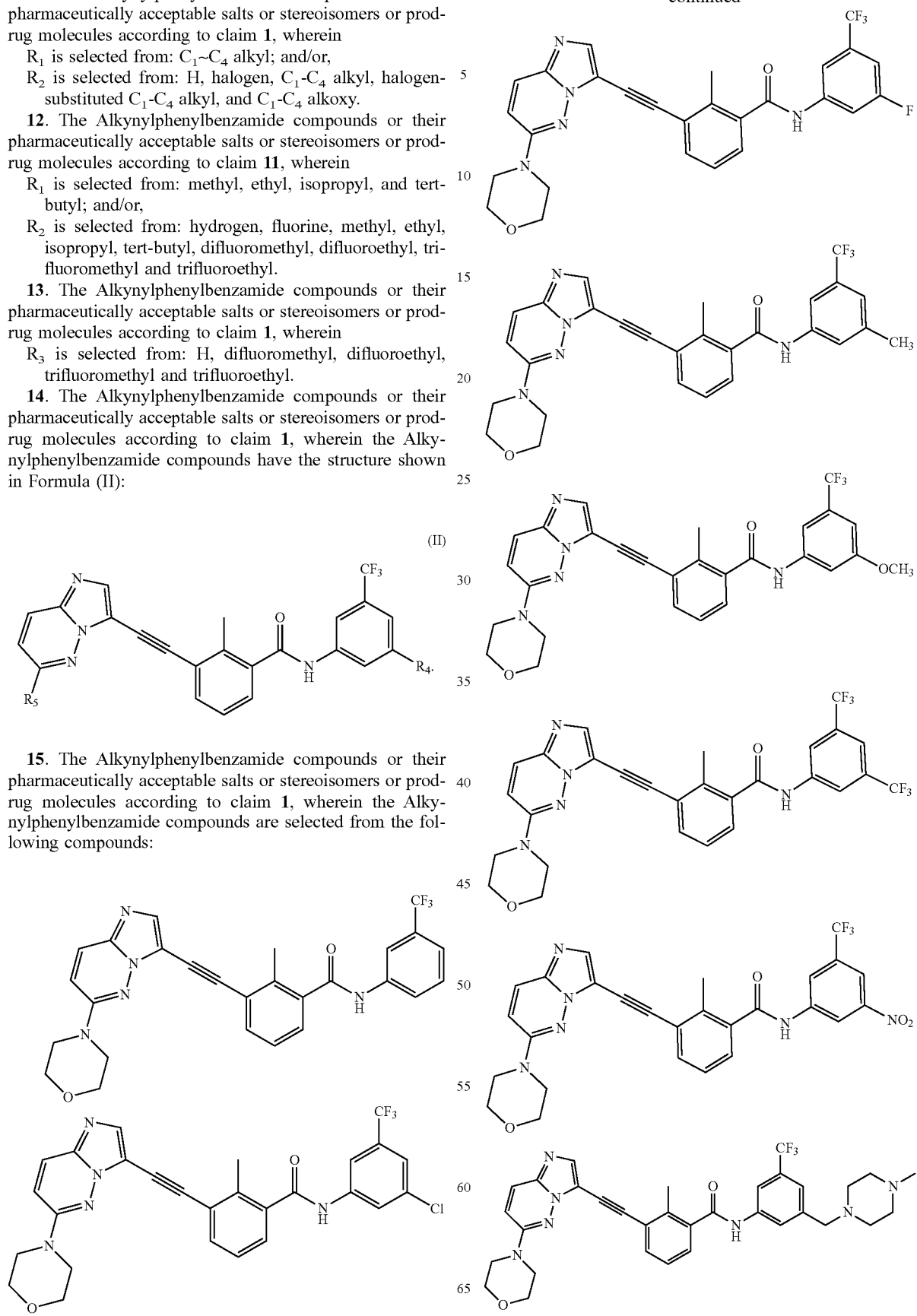

-continued

63
-continued
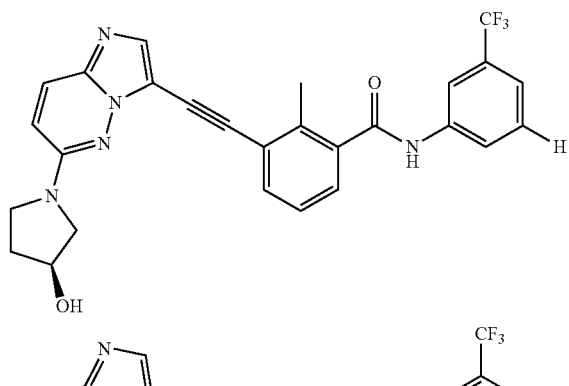
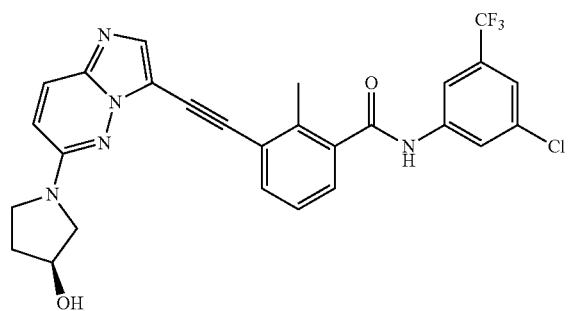
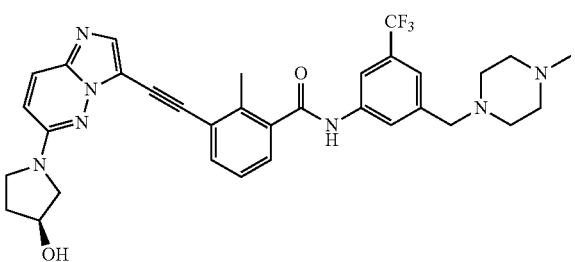
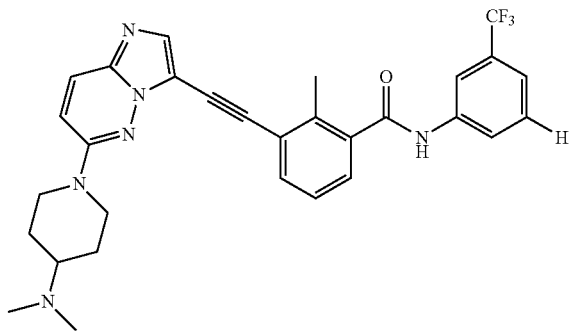
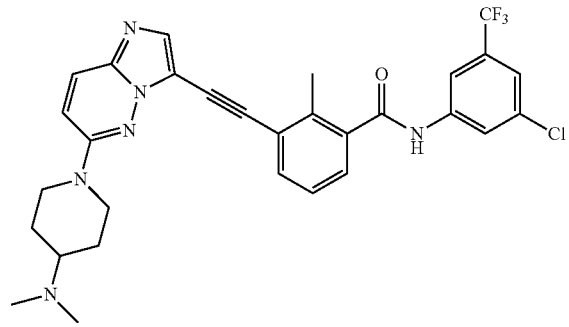
64
-continued
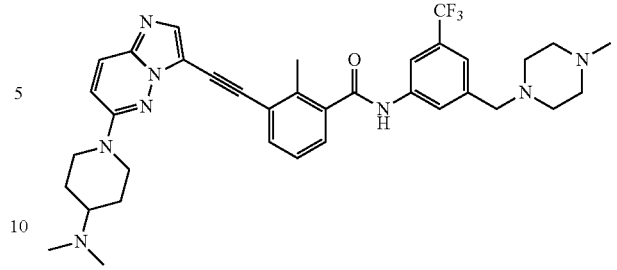
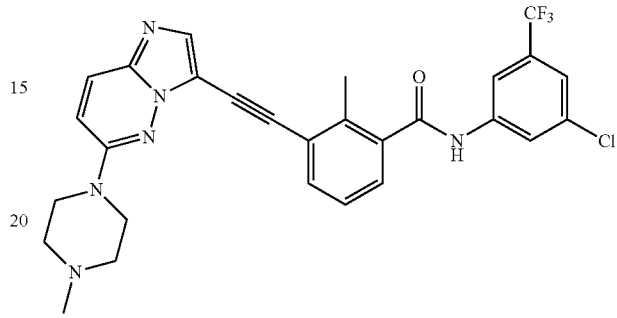
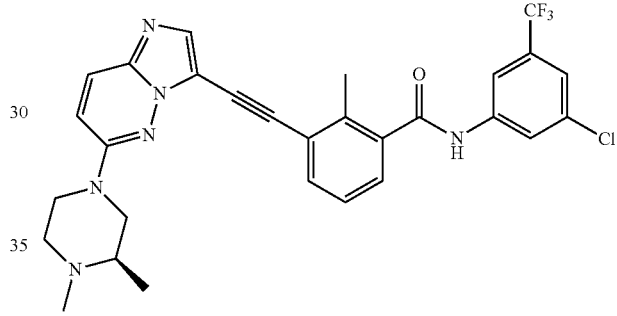
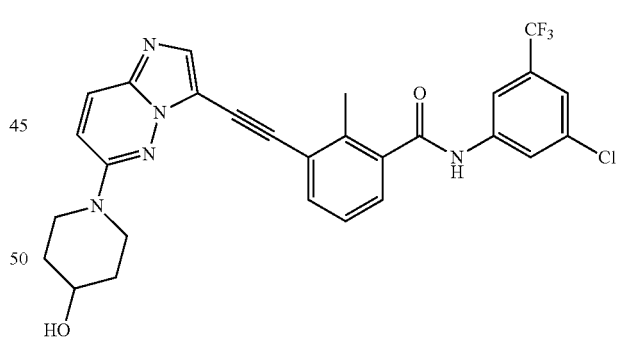
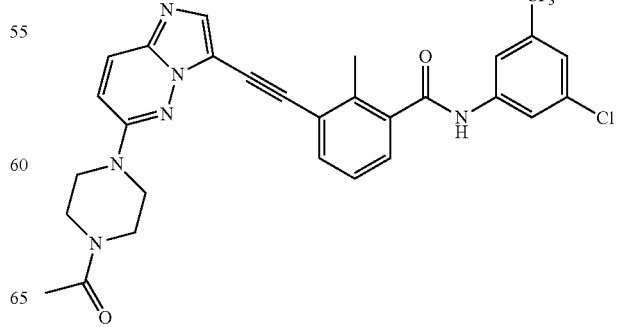

65
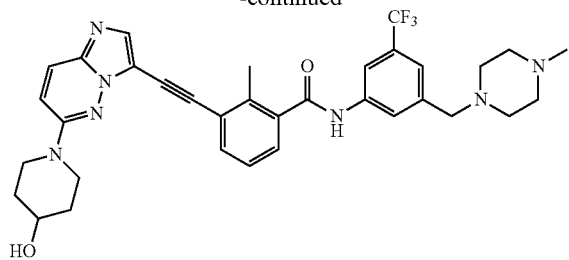
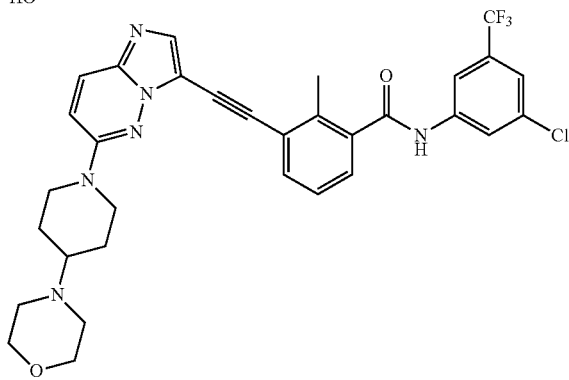
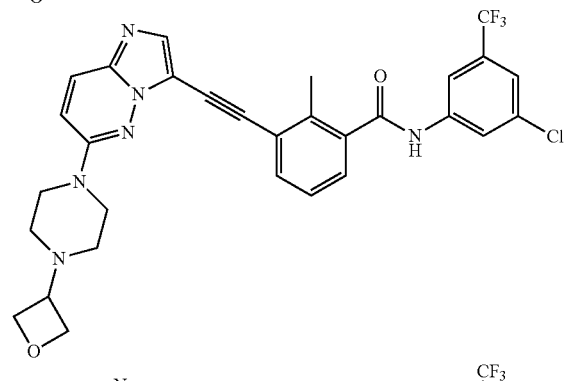
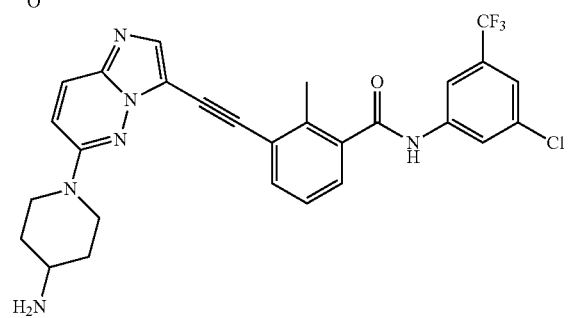
66
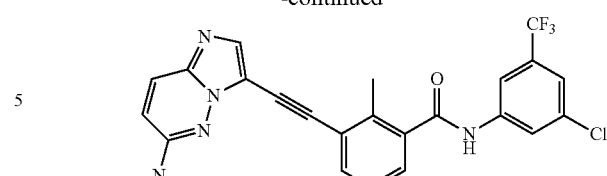
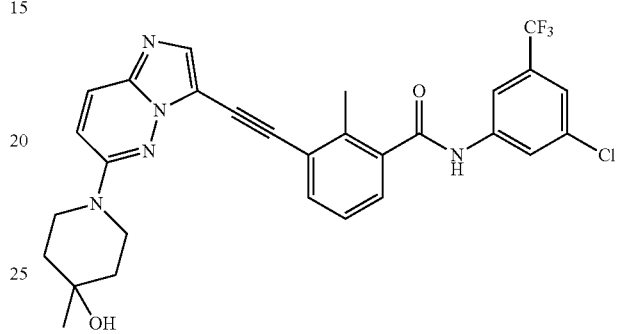
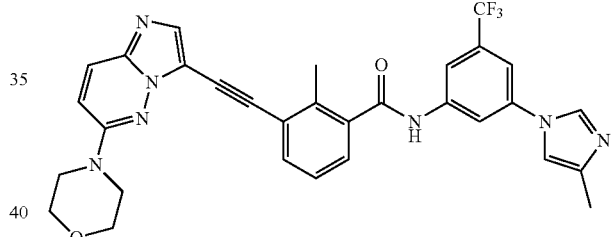
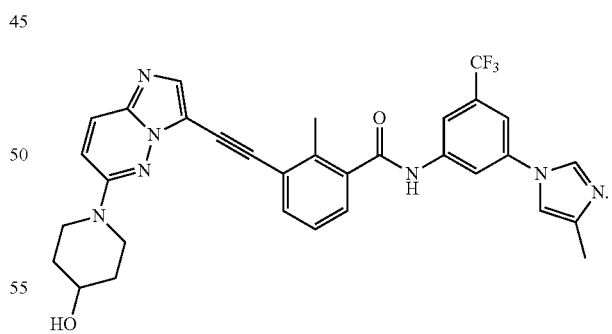
* * * * *